United States Patent
Bell et al.

(10) Patent No.: US 12,331,022 B2
(45) Date of Patent: Jun. 17, 2025

(54) SPIROPIPERIDINE ALLOSTERIC MODULATORS OF NICOTINIC ACETYLCHOLINE RECEPTORS

(71) Applicant: Merck Sharp & Dohme LLC, Rahway, NJ (US)

(72) Inventors: Ian M. Bell, Harleysville, PA (US); Brian T. Campbell, Doylestown, PA (US); Brendan M. Crowley, Collegeville, PA (US); James Fells, Hillsborough, NJ (US); Kenneth J. Leavitt, Garnet Valley, PA (US); Anthony J. Roecker, Harleysville, PA (US); Andrew John Harvey, Paddington Spring Hill (AU); Belinda C. Huff, Thebarton (AU); Dharam Paul, Thebarton (AU); Christophe Morice, Illkirch (FR); Christophe Joseph, Illkirch (FR); Patrick Bazzini, Illkirch (FR); Jean-Marie Contreras, Illkirch (FR); Fabrice Garrido, Illkirch (FR); Aurelie Witzel, Illkirch (FR)

(73) Assignee: Merck Sharp & Dohme LLC, Rahway, NJ (US)

( * ) Notice: Subject to any disclaimer, the term of this patent is extended or adjusted under 35 U.S.C. 154(b) by 841 days.

(21) Appl. No.: 17/606,154

(22) PCT Filed: Apr. 27, 2020

(86) PCT No.: PCT/US2020/030019
§ 371 (c)(1),
(2) Date: Oct. 25, 2021

(87) PCT Pub. No.: WO2020/223136
PCT Pub. Date: Nov. 5, 2020

(65) Prior Publication Data
US 2022/0119351 A1    Apr. 21, 2022

Related U.S. Application Data

(60) Provisional application No. 62/842,099, filed on May 2, 2019.

(51) Int. Cl.
| | | |
|---|---|---|
| C07D 221/20 | (2006.01) |
| A61K 31/438 | (2006.01) |
| A61K 31/444 | (2006.01) |
| A61K 45/06 | (2006.01) |
| C07D 401/12 | (2006.01) |
| C07D 401/14 | (2006.01) |
| C07D 413/12 | (2006.01) |

(52) U.S. Cl.
CPC ......... *C07D 221/20* (2013.01); *A61K 31/438* (2013.01); *A61K 31/444* (2013.01); *A61K 45/06* (2013.01); *C07D 401/12* (2013.01); *C07D 401/14* (2013.01); *C07D 413/12* (2013.01)

(58) Field of Classification Search
CPC .. C07D 221/20; C07D 401/12; C07D 401/14; C07D 413/12; A61K 31/438; A61K 31/444; A61K 45/06
See application file for complete search history.

(56) References Cited

U.S. PATENT DOCUMENTS

| | | | |
|---|---|---|---|
| 11,332,463 B2 * | 5/2022 | Crowley | C07D 513/04 |
| 2017/0275260 A1 | 9/2017 | Crowley et al. | |

FOREIGN PATENT DOCUMENTS

| | | |
|---|---|---|
| WO | 2008147314 A1 | 12/2008 |
| WO | 2015095963 A1 | 7/2015 |
| WO | 2017083867 A1 | 5/2017 |
| WO | 2019079410 A1 | 4/2019 |
| WO | 2019212927 A1 | 11/2019 |

OTHER PUBLICATIONS

Kier et al, Bioisosterism: Quantitation of Structure and Property Effects, Chemistry & Biodiversity, 1, 2004 (Year: 2004).*
Patani et al, Bioisosterism: A Rational Approach in Drug Design, Chem. Rev., 1996, 96, 3147-3176 (Year: 1996).*

(Continued)

*Primary Examiner* — Andrew D Kosar
*Assistant Examiner* — Phillip Matthew Rzeczycki
(74) *Attorney, Agent, or Firm* — John C. Todaro; Patricia A. Shatynski

(57) ABSTRACT

The present disclosure relates to compounds of formula I that are useful as modulators of α7 nAChR, compositions comprising such compounds, and the use of such compounds for preventing, treating, or ameliorating disease, particularly disorders of the central nervous system such as cognitive impairments in Alzheimer's disease, Parkinson's disease, and schizophrenia, as well as for L-DOPA induced-dyskinesia and inflammation

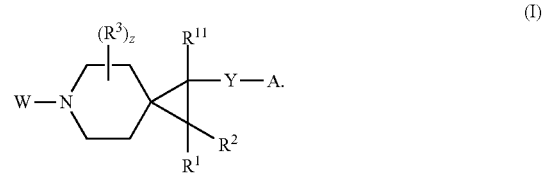

5 Claims, No Drawings

(56) References Cited

OTHER PUBLICATIONS

Gaikwad et al, The Use of Bioisosterism in Drug Design and Molecular Modification, Am. J. Pharm Tech Res., 2012, 2 (4) (Year: 2012).*

Pubchem, Substance Record for SID 376159867, Available Date: Oct. 31, 2018 [retrieved on Aug. 12, 2020]. Retrieved from the Internet:URL: https://pubchem.ncbi.nlm.nih.gov/substanceI376I 59867 entire document.

Substance Record for PubOhem SID 77025099 to PubOhem teaches a compound having the core structure of formula I(p. 2, see shown structure), https://pubchem.ncbi.nlm.nih.gov/substance/77025099 (6 pages).

\* cited by examiner

SPIROPIPERIDINE ALLOSTERIC MODULATORS OF NICOTINIC ACETYLCHOLINE RECEPTORS

CROSS-REFERENCE TO RELATED APPLICATIONS

This application is a U.S. National Stage application of International Patent Application No. PCT/US20/030019, filed Apr. 27, 2020, which claims priority to U.S. Provisional Patent Application No. 62/842,099, filed May 2, 2019.

FIELD OF THE INVENTION

The present disclosure relates to compounds that are useful as modulators of α7 nAChR, compositions comprising such compounds, and the use of such compounds for preventing, treating, or ameliorating disease, particularly disorders of the central nervous system such as cognitive impairments in Alzheimer's disease, Parkinson's disease, and schizophrenia.

BACKGROUND OF THE INVENTION

The α7 nAChR is a fast desensitizing ligand-gated ion channel that has high permeability to $Ca^{2+}$. In human brain, α7 nAChRs are highly expressed in the cortex and hippocampus, regions associated with cognition, see for example, Breese et al. *J. Comp. Neurol.* (1997) 387:385-398. In neurons, α7 nAChRs are localized in both pre-synaptic and post-synaptic structures, where activation of the receptor can modulate neurotransmitter release, neuronal excitability, and intracellular signalling, see for example, Frazier et al. *J. Neurosci.* (1998) 18:1187-1195.

Cognitive impairments are prevalent in many neurological and psychiatric diseases, including Alzheimer's disease (AD), schizophrenia, and Parkinson's disease, and dysfunction in cholinergic signalling contributes to the cognitive impairments of these diseases, see for example, Francis et al. *J. Neurol. Neurosurg. Psychiatry* (1999) 66:137-147. For example, a principal feature of the pathogenesis in AD is the loss of cholinergic neurons in the basal forebrain nuclei, whereas increasing cholinergic transmission via inhibition of acetylcholine esterase is the standard of care for the cognitive symptoms of AD. More specific to the α7 nAChR, it was recently demonstrated that encenicline, a partial agonist of the α7 nAChR, improves cognition in Alzheimer's disease, see for example, Moebius H et al., *67th Annual Meeting. Am. Acad. Neurol.* (AAN) 2015, Abst P7.100. Evidence implicating α7 nAChRs in the etiology of schizophrenia comes from studies demonstrating reduced expression of neuronal α7 nAChRs in the brain of schizophrenic patients and the observation that schizophrenics frequently smoke, which is believed to be a form of self-medication. In addition, variants in the promotor region of the gene coding for the α7 nAChR, CHRNA7, which impacts expression of the α7 nAChR protein, are associated with symptoms of schizophrenia, see for example, Sinkus et al. *Neuropharmacology* (2015) 96:274-288. Moreover, accumulating evidence from clinical trials has indicated that activating α7 nAChR with agonists may have beneficial effects on cognition, see for example, Keefe et al. *Neuropsychopharmacology* (2015) 40:3053-3060 and Bertrand et al. *Pharmacology Reviews* (2015) 67:1025-1073. Therefore, targeting the α7 nAChR represents a therapeutic strategy for the treatment of cognitive impairments associated with various cognitive disorders.

Parkinson's disease (PD) is a neurodegenerative disease characterized by progressive deficits in motor function, such as tremor, bradykinesia, rigidity and impaired postural reflex. The main pathological finding associated with the disease is degeneration of dopaminergic neurons in the substantia nigra, resulting in loss of dopaminergic tone in the striatum. L-DOPA is the current standard treatment for the motor symptoms in PD. However, chronic treatment with L-DOPA in PD patients also induces dyskinesia, a side effect of L-DOPA therapy. New lines of evidence indicate that activating α7 nAChRs acutely alleviates dyskinesia in several animal models, see for example, Zhang et al. *J. Pharmacol. Exp. Ther.* (2014) 351:25-32. In addition, accumulating evidence shows that pretreatment with α7 nAChR agonists may protect against neurodegeneration in nigrostriatal neurons, suggesting α7 activation may have disease modifying properties too, see for example, Suzuki et al. *J. Neurosci. Res.* (2013) 91:462-471. Overall, α7 nAChR is an attractive target for both ameliorating disease progression and managing dyskinesia.

In addition to its expression in the central nervous system, the α7 nAChR is widely expressed in peripheral immune cells including macrophage, monocytes, dendritic cells, and B and T cells, see for example, Rosas-Ballina et al. *Science* (2011) 334:98-101. Activation of peripheral α7 nAChRs is critical for inhibiting the release of proinflammatory cytokines via the cholinergic anti-inflammatory pathway, see for example, Wang et al. *Nature* (2003) 421:384-388. Therefore, α7 nAChR is a potential target for several inflammatory diseases such as rheumatoid arthritis, and atherosclerosis, see for example, W J de Jonge et al. *British J. Pharmacol.* (2007) 151:915-929.

Cough is one of the most common symptoms for which patients seek medical attention. Chronic cough, defined as a cough of greater than 8 weeks of duration, is a clinical syndrome with distinct intrinsic pathophysiology characterized by neuronal hypersensitivity. Current treatment for chronic cough consists of antitussive therapy to decrease cough frequency or severity. However, the available antitussives have limited efficacy and their utility is further restricted by safety and abuse liabilities. Recent studies performed in healthy human volunteers indicate that activation of nAChR may represent a novel, safe, and effective antitussive strategy, see for example, Davenport et al. *Pulm. Pharmacol. Ther.* (2009) 22:82-89; Dicpinigaitis. *Pulm. Pharmacol. Ther.* (2017) 47:45-48. Furthermore, pre-clinical studies suggest that α7 nAChR is likely the target for antitussive nAChR ligands, see for example, Canning et al. *Am. J. Respir. Crit. Care. Med.* (2017) 195:A4498. Therefore, targeting α7 nAChR represents an attractive antitussive strategy in patients with cough.

In recent years, α7-selective positive allosteric modulators (PAMs) have been proposed as a therapeutic approach to treating cognitive impairments in AD, PD, and schizophrenia, as well as L-DOPA induced-dyskinesia, inflammation, and cough. In contrast to α7 agonists that activate the channel irrespective of endogenous agonist, PAMs increase the potency of the endogenous agonist without perturbing the temporal and spatial integrity of neurotransmission. There are two classes of α7 PAMs, type I and type II, which differ based on the functional properties of modulation. The type I PAMs (e.g. NS 1738, see for example, Timmermann et al. *J. Pharmacol. Exp. Ther.* (2007) 323:294-307) predominantly affect the peak current with little or no effect on receptor desensitization, while the type II PAMs (e.g. PNU120596, see for example, Hurst et al. *J. Neurosci.* (2005) 25:4396-4405) markedly delay desensitization of the receptor. Additionally, α7 nAChR PAMs may have improved selectivity over related channel targets, presumably through binding to non-conserved regions of the receptor.

The present invention is directed to a new class of compounds that exhibit positive allosteric modulation of the α7 nAChR.

SUMMARY OF THE INVENTION

The present disclosure relates to novel compounds of formula I pharmaceutically acceptable salts thereof. These compounds may be useful, either as compounds or their pharmaceutically acceptable salts (when appropriate), in the modulation of the α7 nAChR, the prevention, treatment, or amelioration of disease, particularly disorders of the central nervous system such as cognitive impairments in Alzheimer's disease, Parkinson's disease, and schizophrenia and/or as pharmaceutical composition ingredients. As pharmaceutical composition ingredients, these compounds and their salts may be the primary active therapeutic agent, and, when appropriate, may be combined with other therapeutic agents including but not limited to acetylcholinesterase inhibitors, NMDA receptor antagonists, beta-secretase inhibitors, M4 mAChR agonists or PAMs, mGluR2 antagonists or NAMs or PAMs, 5-HT6 antagonists, histamine H3 receptor antagonists, PDE4 inhibitors, PDE9 inhibitors, HDAC6 inhibitors, antipsychotics, MAO-B inhibitors, and levodopa.

In one aspect, the present invention relates to a compound of formula I:

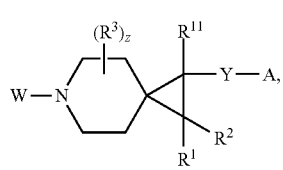

or a pharmaceutically acceptable salt thereof, wherein:
W is

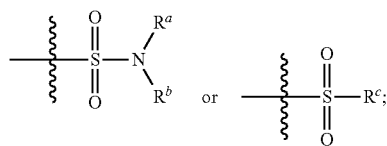

$R^a$ is selected from hydrogen, $(C_1-C_4)$alkyl, $(C_3-C_6)$cycloalkyl, aryl, heteroaryl, and heterocyclyl, wherein said alkyl, cycloalkyl, aryl, heteroaryl and heterocyclyl are optionally substituted with one or more substituents independently selected from $R^8$;
$R^b$ is hydrogen or $(C_1-C_4)$alkyl;
$R^c$ is $(C_1-C_4)$alkyl or heteroaryl, wherein said alkyl is optionally substituted with $R^9$ and said heteroaryl is optionally substituted with one or more $R^{10}$;
A is aryl or heteroaryl, wherein said aryl or heteroaryl is substituted with 0, 1, 2, or 3 $R^4$ groups each $R^4$ independently selected from:
hydroxy,
oxo,
halogen,
cyan,
—S(O)$_n$ C$_{1-6}$ alkyl,
C$_{1-8}$ alkyl,
(C$_1$-C$_8$)haloalkyl,
C$_{1-6}$ alkoxy,
C$_{1-6}$ alkoxyC$_{1-6}$ alkyl,
C$_{1-6}$ alkylamino,
aminoC$_{1-6}$ alkyl,
hydroxyC$_{1-6}$ alkyl,
C$_{3-8}$ cycloalkyl,
C$_{3-8}$ cycloalkylC$_{1-6}$ alkoxy,
heterocyclyl,
aryl, and
heteroaryl;
wherein said alkoxy, alkylamino, aminoalkyl, hydroxyalkyl, alkyl, haloalkyl, cycloalkyl, aryl, heteroaryl and heterocyclyl are optionally substituted with one or more $R^7$ substituents, each $R^7$ substituent independently selected from F, Cl, Br, OH, oxo, CF$_3$, OCF$_3$, CN, $(C_1-C_6)$alkyl, O$(C_1-C_4)$alkyl, —S$(C_1-C_4)$alkyl, —C=O$(C_1-C_4)$alkyl, —(C=O)NR$^5$R$^6$, —(C=O)OR$^5$, $(C_1-C_4)$alkynyl, $(C_3-C_6)$cycloalkyl, —O$(C_3-C_6)$cycloalkyl, —C=O$(C_3-C_6)$cycloalkyl, aryl, heteroaryl and heterocyclyl, wherein said alkyl, cycloalkyl, alkynyl, aryl, heteroaryl and heterocyclyl are optionally independently substituted with one or more $R^{12}$ selected from halogen, $(C_1-C_4)$alkyl, —O$(C_1-C_4)$alkyl, CF$_3$, cyclopropyl, cyano, OH and oxo;
$R^5$ is H or $(C_1-C_4)$alkyl;
$R^6$ is H or $(C_1-C_4)$alkyl;
z is 0, 1, 2, or 3;
Each $R^3$ is independently hydrogen, halogen, cyano, $(C_1-C_4)$alkyl, OH, $(C_1-C_4)$haloalkyl, or —O$(C_1-C_4)$alkyl, wherein, two $R^3$ that are attached to the same carbon atom of the piperidinyl ring may join together to form a $(C_3-C_6)$cycloalkyl ring; or
two $R^3$ that are each attached to different carbon atoms of the piperidinyl ring may join together to form a bridged ring,
wherein said $(C_3-C_6)$cycloalkyl ring or said bridged ring may be optionally substituted with one or more substituents independently selected from OH, halogen, or $(C_1-C_4)$alkyl;
$R^1$ and $R^2$ are each independently selected from hydrogen, halogen, $(C_1-C_4)$alkyl and $(C_1-C_4)$haloalkyl; or
$R^1$ and $R^2$ can come to together to form a $(C_3-C_6)$ cycloalkyl ring wherein said ring may be substituted with 0, 1, 2, 3, or 4, substituents independently selected from OH, halogen, or $(C_1-C_4)$alkyl;
Y is selected from —C(R$^d$R$^e$)—X—, —C(R$^d$R$^e$)—X—C(R$^f$R$^g$), —(C=O)—NR$^h$, or —C(R$^d$)=C(R$^e$);
X is selected from O, NR$^h$, S(O)$_m$, or C(R$^f$R$^g$);
$R^d$ and $R^e$ are each independently selected from hydrogen, halogen, $(C_1-C_4)$alkyl and $(C_1-C_4)$haloalkyl;
$R^f$ and $R^g$ are each independently selected from hydrogen, halogen, $(C_1-C_4)$alkyl and $(C_1-C_4)$haloalkyl;
$R^h$ is selected from hydrogen, $(C_1-C_4)$alkyl and $(C_1-C_4)$haloalkyl;
$R^8$ is OH, $(C_1-C_4)$alkyl, —O$(C_1-C_4)$alkyl, halogen, aryl, heteroaryl, or heterocyclyl;
$R^9$ is halogen, aryl, heteroaryl, or heterocyclyl;
$R^{10}$ is $(C_1-C_4)$alkyl, —O$(C_1-C_4)$alkyl, CF$_3$, or hydroxy;
$R^{11}$ is $(C_1-C_4)$alkyl, —O$(C_1-C_4)$alkyl, $(C_1-C_4)$haloalkyl, or hydroxy;
m is 0, 1, or 2; and
n is 0, 1, or 2.

The present invention also includes pharmaceutical compositions containing a compound of the present invention and methods of preparing such pharmaceutical compositions. The present invention further includes methods of preventing, treating, or ameliorating the cognitive impairments associated with Alzheimer's disease, Parkinson's disease, and schizophrenia.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts thereof. The compounds of formula I are positive allosteric modulators of α7 nAChR.

In a first embodiment of the invention, W is

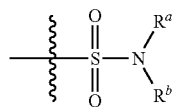

and the other groups are as provided in the general formula above.

In a second embodiment of the invention, W is

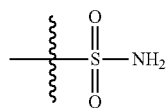 [SMILES: *S(N)(=O)=O]

and the other groups are as provided in the general formula above.

In a third embodiment of the invention, W is

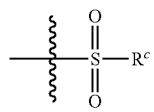

and the other groups are as provided in the general formula above.

In a fourth embodiment of the invention, A is phenyl or a 5-6 membered heteroaryl ring which is substituted with 0, 1, or 2 $R^4$ groups, and the other groups are provided in the general formula above, or as in the first through third embodiments.

In a fifth embodiment of the invention, A is phenyl or a 5-6 membered heteroaryl ring selected from pyridinyl, pyrazolyl, tetrazolyl, and oxadiazolyl, wherein A is substituted with 0, 1, or 2 $R^4$ groups, and the other groups are provided in the general formula above, or as in the first through third embodiments.

In a sixth embodiment of the invention, each $R^4$ is independently selected from: hydroxy, oxo, halogen, cyano, —S(O)$_2$C$_{1-6}$ alkyl, C$_{1-8}$ alkyl, (C$_{1-8}$)haloalkyl, C$_{1-6}$ alkoxy, C$_{1-6}$ alkoxyC$_{1-6}$ alkyl, C$_{1-6}$ alkylamino, hydroxyC$_{1-6}$ alkyl, C$_{3-8}$ cycloalkyl, C$_{3-8}$ cycloalkylC$_{1-6}$ alkoxy heterocyclyl, aryl, and heteroaryl; wherein said alkoxy, alkylamino, hydroxyalkyl, alkyl, haloalkyl, cycloalkyl, aryl, heteroaryl and heterocyclyl are optionally substituted with one or more $R^7$ substituents, and the other groups are provided in the general formula above, or as in the first through fifth embodiments.

In a seventh embodiment of the invention, each $R^4$ is independently selected from: hydroxy, oxo, fluoro, chloro, bromo, cyano, —S(O)$_2$C$_{1-3}$ alkyl, C$_{1-4}$ alkyl, (C$_1$-C$_4$)haloalkyl, C$_{1-6}$ alkoxy, C$_{1-4}$ alkylamino, hydroxyC$_{1-6}$ alkyl, C$_{3-6}$ cycloalkyl, cyclopropylmethoxy, piperazinyl, morpholinyl, phenyl, pyrazolyl, and pyridinyl; wherein said $R^4$ is optionally substituted with one or more $R^7$ substituents, and the other groups are provided in the general formula above, or as in the first through fifth embodiments.

In an eighth embodiment of the invention, each $R^4$ is independently selected from: fluoro, chloro, cyano, —S(O)$_2$C$_{1-3}$ alkyl, C$_{1-4}$ alkyl, (C$_1$-C$_4$)haloalkyl, C$_{1-6}$ alkoxy, C$_{1-4}$ alkylamino, hydroxyC$_{1-6}$ alkyl, C$_{3-6}$ cycloalkyl, cyclopropylmethoxy, piperazinyl, morpholinyl, phenyl, pyrazolyl, and pyridinyl; wherein said $R^4$ is optionally substituted with one or more $R^7$ substituents, and the other groups are provided in the general formula above, or as in the first through fifth embodiments.

In an ninth embodiment of the invention each $R^7$ substituent is independently selected from F, Cl, Br, CF$_3$, OH, OCF$_3$, (C$_1$-C$_6$)alkyl, and O(C$_1$-C$_4$)alkyl and said (C$_1$-C$_6$) alkyl, and —O(C$_1$-C$_5$)alkyl is independently substituted with one or more $R^{12}$, the other groups are provided in the general formula above, or as in the first through eighth embodiments.

In a tenth embodiment of the invention each $R^7$ substituent is independently selected from F, Cl, CF$_3$, OCF$_3$, (C$_1$-C$_6$)alkyl, and O(C$_1$-C$_4$)alkyl and said (C$_1$-C$_6$)alkyl, and —O(C$_1$-C$_5$)alkyl is independently substituted with one or more $R^{12}$, the other groups are provided in the general formula above, or as in the first through eighth embodiments.

In a eleventh embodiment of the invention each $R^{12}$ is independently selected from halogen, hydroxy, (C$_1$-C$_5$)alkyl, and CF$_3$, the other groups are provided in the general formula above, or as in the first through tenth embodiments.

In a twelfth embodiment of the invention each $R^{12}$ is independently selected from halogen, (C$_1$-C$_5$)alkyl, and CF$_3$, the other groups are provided in the general formula above, or as in the first through tenth embodiments.

In a thirteenth embodiment, $R^5$ and $R^6$ are each independently H or methyl, the other groups are provided in the general formula above, or as in the first through twelfth embodiments.

In a fourteenth embodiment, $R^5$ and $R^6$ are each H, the other groups are provided in the general formula above, or as in the first through twelfth embodiments.

In an fifteenth embodiment, each $R^3$ is independently hydrogen or halogen, the other groups are provided in the general formula above, or as in the first through fourteenth embodiments.

In a sixteenth embodiment of the invention, two $R^3$ are each attached to the same carbon atom of the piperidinyl ring and join together to form a (C$_3$-C$_5$)cycloalkyl ring, the other groups are provided in the general formula above, or as in the first through fifteenth embodiments.

In a seventeenth embodiment of the invention, two $R^3$ are each attached to different carbon atoms of the piperidinyl ring and join together to form a bridged ring, the other groups are provided in the general formula above, or as in the first through fourteenth embodiments.

In an eighteenth embodiment of the invention, $R^1$ and $R^2$ are each independently selected from hydrogen, methyl, and halogen, the other groups are provided in the general formula above, or as in the first through seventeenth embodiments.

In a nineteenth embodiment of the invention, $R^1$ and $R^2$ are each independently selected from hydrogen and halogen, the other groups are provided in the general formula above, or as in the first through seventeenth embodiments.

In a twentieth embodiment of the invention, $R^1$ and $R^2$ come together to form a $(C_3-C_6)$cycloalkyl ring wherein said ring may be substituted with 0, 1, 2, 3, or 4, substituents independently selected from OH, halogen, or $(C_1-C_4)$alkyl, the other groups are provided in the general formula above, or as in the first through eighteenth embodiments.

In a twenty-first embodiment of the invention, $R^d$ and $R^e$ are each independently selected from hydrogen, halogen, and $(C_1-C_4)$alkyl, the other groups are provided in the general formula above, or as in the first through twentieth embodiments.

In a twenty-second embodiment of the invention, $R^f$ and $R^g$ are each independently selected from hydrogen, halogen, and $(C_1-C_4)$alkyl, the other groups are provided in the general formula above, or as in the first through twenty-first embodiments.

In a twenty-third embodiment of the invention, $R^h$ is hydrogen, the other groups are provided in the general formula above, or as in the first through twenty-second embodiments.

Representative compounds of the present invention are as follows, where each named compound is intended to encompass its individual isomers, mixtures thereof (including racemates and diastereomeric mixtures):

The invention is also directed to a compound, or a pharmaceutically acceptable salt thereof, selected from the following exemplified compounds:

1-({[2-(difluoromethoxy)pyridin-4-yl]oxy}methyl)-6-azaspiro[2.5]octane-6-sulfonamide;
2-({[2-(difluoromethoxy)pyridin-4-yl]oxy}methyl)-1,1-difluoro-6-azaspiro[2.5]octane-6-sulfonamide;
(1R)-1-{[(5-phenyl-1,2,4-oxadiazol-3-yl)oxy]methyl}-6-azaspiro[2.5]octane-6-sulfonamide;
1-({[2-(trifluoromethyl)pyridin-4-yl]oxy}methyl)-6-azaspiro[2.5]octane-6-sulfonamide;
1,1-difluoro-2-{[(5-phenyl-1,2,4-oxadiazol-3-yl)oxy]methyl}-6-azaspiro[2.5]octane-6-sulfonamide;
1-{[3-(2,2,2-trifluoroethoxy)phenoxy]methyl}-6-azaspiro[2.5]octane-6-sulfonamide;
(1R)-1-({[2-(2,2,2-trifluoroethoxy)pyridin-3-yl]oxy}methyl)-6-azaspiro[2.5]octane-6-sulfonamide;
(1R)-1-({[6-(2,2,2-trifluoroethoxy)pyridin-2-yl]methoxy}methyl)-6-azaspiro[2.5]octane-6-sulfonamide;
(1R)-1-[({6-[(2,2,2-trifluoroethyl)amino]pyridin-2-yl}oxy)methyl]-6-azaspiro[2.5]octane-6-sulfonamide;
(1R)-1-{[(5-chloro-2-methoxyphenyl)sulfanyl]methyl}-6-azaspiro[2.5]octane-6-sulfonamide;
(1R)-1-{[(5-chloro-2-methoxyphenyl)sulfonyl]methyl}-6-azaspiro[2.5]octane-6-sulfonamide;
(1R)—N-(5-chloro-2-methoxyphenyl)-6-sulfamoyl-6-azaspiro[2.5]octane-1-carboxamide;
(1R)-1-{[(5-chloro-2-methoxyphenyl)amino]methyl}-6-azaspiro[2.5]octane-6-sulfonamide;
(1R)—N-(5-chloro-2-methoxyphenyl)-2,2-difluoro-6-sulfamoyl-6-azaspiro[2.5]octane-1-carboxamide;
(1R)-1-({[6-(morpholin-4-yl)pyridin-2-yl]oxy}methyl)-6-azaspiro[2.5]octane-6-sulfonamide;
1,1-difluoro-2-({[4-fluoro-2-(trifluoromethyl)phenyl]sulfanyl}methyl)-6-azaspiro[2.5]octane-6-sulfonamide;
1,1-difluoro-2-{2-[4-fluoro-2-(trifluoromethyl)phenyl]ethyl}-6-azaspiro[2.5]octane-6-sulfonamide;
1,1-difluoro-2-{(E)-2-[4-fluoro-2-(trifluoromethyl)phenyl]ethenyl}-6-azaspiro[2.5]octane-6-sulfonamide;
(1R)-1-{[(2,6-dimethoxypyridin-3-yl)oxy]methyl}-6-azaspiro[2.5]octane-6-sulfonamide;
2-[(5-chloro-2-methoxyphenoxy)methyl]-1,1-difluoro-6-azaspiro[2.5]octane-6-sulfonamide;
(1R)-1-[(4-fluoro-3-methoxyphenoxy)methyl]-6-azaspiro[2.5]octane-6-sulfonamide;
(1S)-1-[(4-fluoro-3-methoxyphenoxy)methyl]-6-azaspiro[2.5]octane-6-sulfonamide;
(1R)-1-[(4-fluoro-2-methoxyphenoxy)methyl]-6-azaspiro[2.5]octane-6-sulfonamide;
1-{[4-fluoro-2-(trifluoromethyl)phenoxy]methyl}-6-azaspiro[2.5]octane-6-sulfonamide;
1,1-difluoro-2-{[5-fluoro-2-(trifluoromethyl)phenoxy]methyl}-6-azaspiro[2.5]octane-6-sulfonamide;
1-{[2-(difluoromethoxy)phenoxy]methyl}-6-azaspiro[2.5]octane-6-sulfonamide;
1,1-difluoro-2-{[4-fluoro-2-(trifluoromethyl)phenoxy]methyl}-6-azaspiro[2.5]octane-6-sulfonamide;
1,1-difluoro-2-({[1-methyl-3-(trifluoromethyl)-1H-pyrazol-5-yl]oxy}methyl)-6-azaspiro[2.5]octane-6-sulfonamide;
(1S)-1-{[(5-phenyl-1,2,4-oxadiazol-3-yl)oxy]methyl}-6-azaspiro[2.5]octane-6-sulfonamide;
1-{[(3-methyl-1-phenyl-1H-pyrazol-5-yl)oxy]methyl}-6-azaspiro[2.5]octane-6-sulfonamide;
1-{[5-fluoro-2-(trifluoromethyl)phenoxy]methyl}-6-azaspiro[2.5]octane-6-sulfonamide;
(1S)-1-({[4-methoxy-6-(2,2,2-trifluoroethoxy)pyridin-2-yl]oxy}methyl)-6-azaspiro[2.5]octane-6-sulfonamide;
(1R)-1-({[6-(cyclopropylmethoxy)pyridin-2-yl]oxy}methyl)-6-azaspiro[2.5]octane-6-sulfonamide;
(1S)-1-({[6-(cyclopropylmethoxy)pyridin-2-yl]oxy}methyl)-6-azaspiro[2.5]octane-6-sulfonamide;
(1R)-1-({[6-(3,5-dimethyl-1H-pyrazol-1-yl)pyridin-2-yl]oxy}methyl)-6-azaspiro[2.5]octane-6-sulfonamide;
(1S)-1-({[6-(3,5-dimethyl-1H-pyrazol-1-yl)pyridin-2-yl]oxy}methyl)-6-azaspiro[2.5]octane-6-sulfonamide;
4,4-difluoro-1-{[(5-phenyl-1,2,4-oxadiazol-3-yl)oxy]methyl}-6-azaspiro[2.5]octane-6-sulfonamide;
1-{[3-(difluoromethoxy)phenoxy]methyl}-6-azaspiro[2.5]octane-6-sulfonamide;
(1R)-1-{[3-(trifluoromethoxy)phenoxy]methyl}-6-azaspiro[2.5]octane-6-sulfonamide;
(1S)-1-{[3-(trifluoromethoxy)phenoxy]methyl}-6-azaspiro[2.5]octane-6-sulfonamide;
1-[(2-fluoro-5-methoxyphenoxy)methyl]-6-azaspiro[2.5]octane-6-sulfonamide;
1-{[(6-methoxypyridin-2-yl)oxy]methyl}-6-azaspiro[2.5]octane-6-sulfonamide;
2-{[3-(difluoromethoxy)phenoxy]methyl}-1,1-difluoro-6-azaspiro[2.5]octane-6-sulfonamide;
1,1-difluoro-2-{[3-(2,2,2-trifluoroethoxy)phenoxy]methyl}-6-azaspiro[2.5]octane-6-sulfonamide;
1,1-difluoro-2-[(2-fluoro-5-methoxyphenoxy)methyl]-6-azaspiro[2.5]octane-6-sulfonamide;
1-({[2-(2,2,2-trifluoroethoxy)pyridin-4-yl]oxy}methyl)-6-azaspiro[2.5]octane-6-sulfonamide;
1,1-difluoro-2-({[2-(2,2,2-trifluoroethoxy)pyridin-4-yl]oxy}methyl)-6-azaspiro[2.5]octane-6-sulfonamide;
1,1-difluoro-2-({[2-(2,2,2-trifluoroethoxy)pyridin-3-yl]oxy}methyl)-6-azaspiro[2.5]octane-6-sulfonamide;
(1R)-1-({[6-(2,2,2-trifluoroethoxy)pyridin-2-yl]oxy}methyl)-6-azaspiro[2.5]octane-6-sulfonamide;

(1S)-1-({[6-(2,2,2-trifluoroethoxy)pyridin-2-yl]oxy}methyl)-6-azaspiro[2.5]octane-6-sulfonamide;
4,4-difluoro-1-({[6-(2,2,2-trifluoroethoxy)pyridin-2-yl]oxy}methyl)-6-azaspiro[2.5]octane-6-sulfonamide;
1,1-difluoro-2-({[6-(2,2,2-trifluoroethoxy)pyridin-2-yl]oxy}methyl)-6-azaspiro[2.5]octane-6-sulfonamide;
1-[(5-chloro-2-methoxyphenoxy)methyl]-6-azaspiro[2.5]octane-6-sulfonamide;
1-({[4-(trifluoromethyl)phenyl]sulfanyl}methyl)-6-azaspiro[2.5]octane-6-sulfonamide;
1,1-difluoro-2-({[4-(trifluoromethyl)phenyl]sulfanyl}methyl)-6-azaspiro[2.5]octane-6-sulfonamide;
(1R)-1-({[6-(methylsulfonyl)pyridin-2-yl]oxy}methyl)-6-azaspiro[2.5]octane-6-sulfonamide;
(1R)-1-({[6-(4-methylpiperazin-1-yl)pyridin-2-yl]oxy}methyl)-6-azaspiro[2.5]octane-6-sulfonamide;
(1R)-1-{[(6-cyanopyridin-2-yl)oxy]methyl}-6-azaspiro[2.5]octane-6-sulfonamide;
(1R)-1-{[(6-methylpyridin-2-yl)oxy]methyl}-6-azaspiro[2.5]octane-6-sulfonamide;
(1R)-1-{([(6-cyclopropylpyridin-2-yl)oxy]methyl}-6-azaspiro[2.5]octane-6-sulfonamide;
(1R)-1-({[6-(3-methyl-1H-pyrazol-1-yl)pyridin-2-yl]oxy}methyl)-6-azaspiro[2.5]octane-6-sulfonamide;
(1R)-1-{[(6-methoxypyridin-2-yl)oxy]methyl}-6-azaspiro[2.5]octane-6-sulfonamide;
(1R)-1-({[6-(2-hydroxypropan-2-yl)pyridin-2-yl]oxy}methyl)-6-azaspiro[2.5]octane-6-sulfonamide;
(1R)-1-({[6-(propan-2-yl)pyridin-2-yl]oxy}methyl)-6-azaspiro[2.5]octane-6-sulfonamide;
(1R)-1-{[(6-ethoxypyridin-2-yl)oxy]methyl}-6-azaspiro[2.5]octane-6-sulfonamide;
(1R)-1-{[(6-tert-butylpyridin-2-yl)oxy]methyl}-6-azaspiro[2.5]octane-6-sulfonamide;
(1R)-1-({[6-(1,1-difluoroethyl)pyridin-2-yl]oxy}methyl)-6-azaspiro[2.5]octane-6-sulfonamide;
(1R)-1-{[(6-phenylpyridin-2-yl)oxy]methyl}-6-azaspiro[2.5]octane-6-sulfonamide;
(1R)-1-[(2,4'-bipyridin-6-yloxy)methyl]-6-azaspiro[2.5]octane-6-sulfonamide;
(2R)-2-{[(5-chloro-2-methoxyphenyl)amino]methyl}-1,1-difluoro-6-azaspiro[2.5]octane-6-sulfonamide;
(2R)-2-{[(2,5-dimethylphenyl)amino]methyl}-1,1-difluoro-6-azaspiro[2.5]octane-6-sulfonamide;
1,1-difluoro-2-{[(1-phenyl-1H-tetrazol-5-yl)sulfanyl]methyl}-6-azaspiro[2.5]octane-6-sulfonamide; (1R)—N-(2-methoxyphenyl)-6-sulfamoyl-6-azaspiro[2.5]octane-1-carboxamide;
(1R)—N-(3-chlorophenyl)-6-sulfamoyl-6-azaspiro[2.5]octane-1-carboxamide; and
(1S)—N-(5-chloro-2-methoxyphenyl)-2,2-difluoro-6-sulfamoyl-6-azaspiro[2.5]octane-1-carboxamide.

The present invention encompasses for each of the various embodiments of the compounds of the invention described herein, including those of Formula I and the various embodiments thereof and the compounds of the examples, all forms of the compounds such as, for example, any solvates, hydrates, stereoisomers, and tautomers of said compounds and of any pharmaceutically acceptable salts thereof. Additionally, in the examples described herein, the compounds of the invention may be depicted in the salt form. In such cases, it is to be understood that the compounds of the invention include the free acid or free base forms of such salts, and any pharmaceutically acceptable salt of said free acid or free base forms.

In addition, when a compound of the invention contains both a basic moiety, such as, but not limited to an aliphatic primary, secondary, tertiary or cyclic amine, an aromatic or heteroaryl amine, pyridine or imidazole, and an acidic moiety, such as, but not limited to tetrazole or carboxylic acid, zwitterions ("inner salts") may be formed and are included within the term "salt(s)" as used herein. It is understood that certain compounds of the invention may exist in zwitterionic form, having both anionic and cationic centers within the same compound and a net neutral charge. Such zwitterions are included within the invention.

Other embodiments of the present invention include the following:

(a) A pharmaceutical composition comprising a compound of formula I and a pharmaceutically acceptable carrier.

(b) The pharmaceutical composition of (a), further comprising a second therapeutic agent selected from the group consisting of acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa.

(c) The pharmaceutical composition of (b), wherein the second therapeutic agent is an antipsychotic selected from the group consisting of clozapine, olanzapine, risperidone, aripiprazole, quetiapine, haloperidol, loxapine, thioridazine, molindone, thiothixene, fluphenazine, mesoridazine, trifluoperazine, chlorpromazine, and perphenazine.

(d) A pharmaceutical combination that is (i) a compound of formula I and (ii) a second therapeutic agent selected from the group consisting of acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa wherein the compound of formula I and the second therapeutic agent are each employed in an amount that renders the combination effective for treating cognitive impairments associated with Alzheimer's disease, Parkinson's disease, or schizophrenia.

(e) The combination of (d), wherein the second therapeutic agent is an antipsychotic selected from the group consisting of clozapine, olanzapine, risperidone, aripiprazole, quetiapine, haloperidol, loxapine, thioridazine, molindone, thiothixene, fluphenazine, mesoridazine, trifluoperazine, chlorpromazine, and perphenazine.

(f) A use of a compound of formula I in the preparation of a medicament for modulating α7 nAChR activity in a subject in need thereof.

(g) A use of a compound of formula I in the preparation of a medicament for treating cognitive impairments associated with Alzheimer's disease, Parkinson's disease, and schizophrenia in a subject in need thereof.

(h) A method of treating cognitive impairments associated with Alzheimer's disease, Parkinson's disease, and schizophrenia and/or reducing the likelihood or severity of symptoms of cognitive impairments associated with Alzheimer's disease, Parkinson's disease, and schizophrenia in a subject in need thereof, which comprises administering to the subject an effective amount of a compound of formula I.

(i) The method of (h), wherein the compound of formula I is administered in combination with an effective amount of at least one second therapeutic agent selected from the group consisting of acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa.

(j) The method of (i), wherein the second therapeutic agent is an antipsychotic selected from the group consisting of clozapine, olanzapine, risperidone, aripiprazole, quetiapine, haloperidol, loxapine, thioridazine, molindone, thiothixene, fluphenazine, mesoridazine, trifluoperazine, chlorpromazine, and perphenazine.

(k) A method of modulating α7 nAChR activity in a subject in need thereof, which comprises administering to the subject the pharmaceutical composition of (a), (b), or (c) or the combination of (d) or (e).

(l) A method of treating cognitive impairments associated with Alzheimer's disease, Parkinson's disease, and schizophrenia and/or reducing the likelihood or severity of symptoms of cognitive impairments associated with Alzheimer's disease, Parkinson's disease, and schizophrenia in a subject in need thereof, which comprises administering to the subject the pharmaceutical composition of (a), (b), or (c) or the combination of (d) or (e).

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (l) above are understood to include all embodiments of the compounds and/or salts, including such embodiments as result from combinations of embodiments.

Additional embodiments of the invention include the pharmaceutical compositions, combinations, uses and methods set forth in (a) through (l) above, wherein the compound of the present invention employed therein is a compound of one of the embodiments, aspects, classes, sub-classes, or features of the compounds described above. In all of these embodiments, the compound may optionally be used in the form of a pharmaceutically acceptable salt as appropriate.

The present invention also includes a compound of the present invention for use (i) in, (ii) as a medicament for, or (iii) in the preparation of a medicament for: (a) preventing or treating cognitive impairments associated with Alzheimer's disease, Parkinson's disease, schizophrenia, and L-DOPA induced-dyskinesia, or (b) treating cognitive impairments associated with Alzheimer's disease, Parkinson's disease, schizophrenia, and L-DOPA induced-dyskinesia and/or reducing the likelihood or severity of symptoms of cognitive impairments associated with Alzheimer's disease, Parkinson's disease, schizophrenia, and L-DOPA induced-dyskinesia, or (c) use in medicine. In these uses, the compounds of the present invention can optionally be employed in combination with one or more second therapeutic agents selected from acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa.

Chemical names, common names, and chemical structures may be used interchangeably to describe the same structure.

As used herein, the term "administration" and variants thereof (e.g., "administering" a compound) in reference to a compound of the invention means providing the compound to the individual in need of treatment. When a compound of the invention is provided in combination with one or more other active agents (e.g., cholinesterase inhibitors such as donepezil, rivastigmine, and galantamine), "administration" and its variants are each understood to include concurrent and sequential administration of the compound or salt and other agents.

The term "alkyl" refers to an aliphatic hydrocarbon group having one of its hydrogen atoms replaced with a bond. An alkyl group may be straight or branched. An alkyl group contains from 1 to 8 carbon atoms [$(C_1-C_8)$alkyl] or from 1 to 6 carbon atoms [$(C_1-C_6)$alkyl] or from 1 to 4 carbon atoms [$(C_1-C_4)$alkyl]. Non-limiting examples of alkyl groups include methyl (Me), ethyl, n-propyl, isopropyl, n-butyl, sec-butyl, isobutyl, and tert-butyl. In one embodiment, an alkyl group is linear. In another embodiment, an alkyl group is branched.

When "alkyl" is substituted, said "alkyl" includes alkyl, O-alkyl, S-alkyl and (C=O)-alkyl.

The term "alkynyl" refers to a hydrocarbon radical straight or branched containing from 2 to 12 carbon atoms and at least one carbon to carbon triple bond. Up to three carbon-carbon triple bonds may be present. Thus, "$C_2-C_6$ alkynyl" means an alkynyl radical having from 2 to 6 carbon atoms. Thus, "$C_2-C_4$ alkynyl" means an alkynyl radical having from 2 to 4 carbon atoms. Alkynyl groups include ethynyl, propynyl, butynyl, 3-methylbutynyl and so on. In one embodiment, an alkynyl group is linear. In another embodiment, an alkynyl group is branched.

The term "alkoxy" refers to an alkyl (carbon and hydrogen chain) group singularly bonded to oxygen (R—O). Non-limiting examples of alkoxy are methoxy ($CH_3$ O—), ethoxy ($CH_3$ $CH_2$ O—) and butoxy ($CH_3$ $CH_2$ $CH_2$ O—).

The term "aryl" refers to any mono- and poly-carbocyclic ring systems wherein the individual carbocyclic rings in the polyring systems are fused or attached to each other via a single bond and wherein at least one ring is aromatic. Suitable aryl groups include phenyl, indanyl, naphthyl, tetrahydronaphthyl, and biphenyl. Aryl ring systems may include, where appropriate, an indication of the variable to which a particular ring atom is attached. Unless otherwise indicated, substituents to the aryl ring systems can be attached to any ring atom, provided that such attachment results in formation of a stable ring system.

In an embodiment, "aryl" is phenyl.

When "aryl" is substituted, said "aryl" includes aryl and O-aryl.

"Celite®" (Fluka) diatomite is diatomaceous earth, and can be referred to as "celite".

The term "composition" is intended to encompass a product comprising the specified ingredients, as well as any product which results from combining the specified ingredients.

The term "cycloalkyl" as used herein, refers to any non-aromatic mono- and poly-carbocyclic ring systems comprising from 3 to 10 ring carbon atoms [($C_3$-$C_{10}$) cycloalkyl], or from 3 to 6 ring carbon atoms [($C_3$-$C_6$) cycloalkyl] wherein the individual carbocyclic rings in the polyring systems are fused, including spiro ring fusions, or attached to each other via a single bond. Non-limiting examples of monocyclic cycloalkyls include cyclopropyl, cyclobutyl, cyclopentyl, cyclohexyl, bicyclo[4.1.0]heptyl, spiro[2.4]heptyl, spiro[3.3]heptyl, spiro[2.5]octyl, and cycloheptyl. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

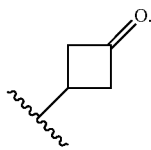

When "cycloalkyl" is substituted, said "cycloalkyl" includes cycloalkyl, O-cycloalkyl and (C=O)-cycloalkyl.

In an embodiment, "cycloalkyl" is cyclopropyl, cyclobutyl, cyclopentyl or cyclohexyl.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. The term also includes herein the amount of active compound sufficient to modulate α7 nAChR activity and thereby elicit the response being sought (i.e., a "therapeutically effective amount"). When the active compound (i.e., active ingredient) is administered as the salt, references to the amount of active ingredient are to the free acid or free base form of the compound.

The term "halogen" (or "halo") refers to atoms of fluorine, chlorine, bromine and iodine (alternatively referred to as fluoro (F), chloro (Cl), bromo (Br), and iodo (I)).

"Haloalkyl" refers to an alkyl group as described above wherein one or more (in particular 1 to 5) hydrogen atoms have been replaced by halogen atoms, with up to complete substitution of all hydrogen atoms with halo groups. $C_{1-6}$ haloalkyl, for example, includes —$CF_3$, —$CF_2CF_3$, —$CHFCH_3$, and the like.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

The term "heteroaryl" as used herein, refers to any monocyclic or multicyclic ring system comprising 5 to 14 ring atoms, wherein from 1 to 4 of the ring atoms is independently 0, N, or S and the remaining ring atoms are carbon atoms, and wherein at least one ring is aromatic. In one embodiment, a heteroaryl group has 5 to 10 ring atoms. In another embodiment, a heteroaryl group is monocyclic and has 5 or 6 ring atoms. In another embodiment, a heteroaryl group is bicyclic and has 9 or 10 ring atoms. A heteroaryl group is usually joined via a ring carbon atom but may be joined via a non-carbon atom provided that this results in a stable compound, and any nitrogen atom of a heteroaryl can be optionally oxidized to the corresponding N-oxide. The term "heteroaryl" also encompasses a heteroaryl group, as defined above, which is fused to a benzene ring. The term "heteroaryl" also encompasses any fused polycyclic ring system containing at least one ring heteroatom selected from N, O, and S, wherein at least one ring of the fused polycyclic ring system is aromatic. For example, the term "9 to 10-membered bicyclic heteroaryl" encompasses a non-aromatic 5 membered heterocyclic ring that is fused to a benzene or pyridyl ring. Non-limiting examples of heteroaryls include benzimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzoyl and the like, and all isomeric forms thereof. The term "heteroaryl" also refers to partially saturated heteroaryl moieties such as, for example, tetrahydroisoquinolyl, tetrahydroquinolyl and the like, provided that they contain at least one aromatic ring. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring.

In an embodiment, "heteroaryl" is benzimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, tetrazolyl, or triazolyl.

In another embodiment, "heteroaryl" is carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, tetrazolyl, or triazolyl.

In another embodiment, "heteroaryl" is furanyl, imidazolyl, indolinyl, indolyl, indolazinyl, indazolyl, isoindolyl, isoquinolyl, isothiazolyl, isoxazolyl, oxadiazolyl, oxazolyl, pyrazinyl, pyrazolyl, pyridazinyl, pyridazinyl, pyridyl, pyrimidyl, pyrrolyl, thiadiazolyl, thiazolyl, thienyl, tetrazolyl, or triazolyl.

In one embodiment of the invention, a 5-membered heteroaryl ring is selected from furanyl, imidazolyl, isothiazolyl, isoxazolyl, oxadiazolyl, oxazolyl, pyrazolyl, pyrrolyl, tetrazolyl, thiadiazolyl, thiazolyl, thienyl, and triazolyl.

In another embodiment, "5-membered heteroaryl ring" is furanyl, imidazolyl, isothiazolyl, isoxazolyl, oxadiazolyl, oxazolyl, pyrazolyl, pyrrolyl, tetrazolyl, thiadiazolyl, thiazolyl, thienyl, and triazolyl.

In another embodiment of the invention a "6-membered heteroaryl ring" is selected from pyridazinyl, pyridinyl, pyrazinyl, and pyrimidinyl.

The term "heterocycle" or "heterocyclyl" as used herein is intended to mean a 3 to 10-membered non-aromatic heterocycle containing from 1 to 4 heteroatoms selected from the group consisting of O, N, and S, and includes monocyclic or bicyclic groups (fused, bridged or spirocyclic). Further examples of "heterocyclyl" include, but are not limited to the following: oxazoline, isoxazoline, oxetanyl, tetrahydropyranyl, azetidinyl, 1,4-dioxanyl, hexahydroazepinyl, piperazinyl, piperidinyl, pyrrolidinyl, morpholinyl, thiomorpholinyl, dihydrofuranyl, dihydroimidazolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydrotetrazolyl, dihydrothiadiazolyl, dihydrothiazolyl, dihydrothienyl, dihydrotriazolyl, tetrahydrofuranyl, and tetrahydrothienyl, and N-oxides thereof. Attachment of a heterocyclyl substituent can occur via a carbon atom or via a heteroatom.

In an embodiment, "heterocycle" or "heterocyclyl" is oxazoline, isoxazoline, oxetanyl, tetrahydropyranyl, azetidinyl, 1,4-dioxanyl, hexahydroazepinyl, piperazinyl, piperidinyl, pyrrolidinyl, morpholinyl, or thiomorpholinyl.

In an embodiment, "heterocycle" or heterocyclyl" is dihydrofuranyl, dihydroimidazolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydrotetrazolyl, dihydrothiadiazolyl, dihydrothiazolyl, dihydrothienyl, dihydrotriazolyl, tetrahydrofuranyl, or tetrahydrothienyl.

In an embodiment, "heterocycle" or heterocyclyl" is morpholinyl and piperidinyl.

By "pharmaceutically acceptable" is meant that the ingredients of the pharmaceutical composition must be compatible with each other and not deleterious to the recipient thereof.

As used herein, the term "optionally" means that the subsequently described event(s) may or may not occur, and includes both event(s), which occur, and events that do not occur.

The term "preventing" as used herein with respect to Alzheimer's disease or other neurological diseases, refers to reducing the likelihood of disease progression.

The term "subject" (alternatively referred to herein as "patient"), as used herein, refers to an animal, preferably a mammal, most preferably a human.

The term "substituted" means that one or more hydrogens on the designated atom is replaced with a selection from the indicated group, provided that the designated atom's normal valency under the existing circumstances is not exceeded, and that the substitution results in a stable compound. Unless expressly stated to the contrary, substitution by a named substituent is permitted on any atom provided such substitution is chemically allowed and results in a stable compound. Combinations of substituents and/or variables are permissible only if such combinations result in stable compounds.

The term "substituted with one or more" refers to substitution with the named substituent or substituents, multiple degrees of substitution, up to replacing all hydrogen atoms with the same or different substituents, being allowed unless the number of substituents is explicitly stated. Where the number of substituents is not explicitly stated, one or more is intended.

As used herein, "a compound of the invention" means a compound of formulae I or Ia, or a salt, solvate or physiologically functional derivative thereof.

The term "solvate" refers to a complex of variable stoichiometry formed by a solute (in this invention, a compound of formulae I or Ia, or a salt thereof) and a solvent. Such solvents for the purpose of the invention may not interfere with the biological activity of the solute. Examples of suitable solvents include, but are not limited to, water, acetone, methanol, ethanol and acetic acid. Preferably the solvent used is a pharmaceutically acceptable solvent. Examples of suitable pharmaceutically acceptable solvents included water, ethanol and acetic acid.

A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject).

In another embodiment of formula I, X is $S(O)_2$.
In another embodiment of formula I, X is C(O).
In another embodiment of formula I, X is S(O).
In another embodiment of formula I, X is S.
In another embodiment of formula I, X is O.
In another embodiment of formula I, X is $NR^h$.
In another embodiment of formula I, X is NH.
In another embodiment of formula I, X is $CR^fR^g$.
In another embodiment of formula I, Y is $C(R^dR^e)$—$NR^h$.
In another embodiment of formula I, Y is $C(R^dR^e)$—O.
In another embodiment of formula I, Y is (C=O)—$NR^h$.
In another embodiment of formula I, Y is $C(R^d)$=$C(R^e)$.
In another embodiment of formula I, Y is $C(R^dR^e)$—X.
In another embodiment of formula I, Y is $C(R^dR^e)$—X—$C(R^fR^g)$.

In another embodiment of formula I, $R^a$ is H, $(C_1-C_4)$alkyl, or $(C_3-C_6)$cycloalkyl, wherein said alkyl is optionally substituted with phenyl, pyridinyl, or isothiazolyl.

In another embodiment of formula I, $R^a$ is H or $(C_1-C_4)$ alkyl.

In another embodiment of formula I, $R^a$ is H or methyl.
In another embodiment of formula I, $R^a$ is H.
In another embodiment of formula I, $R^b$ is H or methyl.
In another embodiment of formula I, $R^b$ is H.

In another embodiment of formula I, $R^c$ is $(C_1-C_4)$alkyl, thienyl, pyrazolyl, benzoxadiazolyl, benzothiazolyl, or oxadiazolyl, wherein said thienyl, pyrozolyl, benzoxadiazolyl, and oxadiazolyl are optionally substituted with one or more methyl or hydroxyl, and wherein said alkyl is optionally substituted with pyridinyl, tetrahydropyranyl, isothiazolyl, or phenyl.

In another embodiment of formula I, $R^c$ is methyl.

In another embodiment of formula I, A (or Ring A) is phenyl, pyridinyl, pyrimidinyl, pyrazinyl, oxadiazolyl, thiazolyl, pyrazolyl, thiadiazolyl, oxazolyl, imidazolyl, isothiazolyl, isoxazolyl, furanyl, thienyl, triazolyl, tetrazolyl, or pyrrolyl.

In another embodiment of formula I, A (or Ring A) is phenyl, pyridinyl, oxadiazolyl, thiazolyl, pyrazolyl, thiadiazolyl, oxazolyl, isoxazolyl, tetrazolyl, or imidazolyl.

In another embodiment of formula I, A (or Ring A) is phenyl, pyridinyl, oxadiazolyl, thiazolyl, oxazolyl, pyrazolyl, isoxazolyl, tetrazolyl, or thiadiazolyl.

In another embodiment of formula I, A (or Ring A) is phenyl, pyridinyl, oxadiazolyl, oxazolyl, isoxazolyl, tetrazolyl, or thiazolyl.

In one embodiment of formula I, $R^4$ is selected from hydroxy, oxo, halogen, cyano, —$SC_{1-6}$ alkyl, —$S(O)C_{1-6}$ alkyl, —$S(O)_2C_{1-6}$ alkyl, $C_{1-8}$ alkyl, $(C_1-C_8)$haloalkyl, $C_{1-6}$ alkoxy, $C_{1-6}$ alkoxy$C_{1-6}$ alkyl, $C_{1-6}$ alkylamino, amino$C_{1-6}$ alkyl, hydroxy$C_{1-6}$ alkyl, cyclopropyl$C_{1-6}$ alkoxy, cyclobutyl$C_{1-6}$ alkoxy, cyclopentyl$C_{1-6}$ alkoxy, cyclohexyl$C_{1-6}$ alkoxy, cyclopropyl, cyclobutyl, cyclopentyl, cyclohexyl, phenyl, indanyl, tetrahydronaphthalenyl, pyrazolyl, pyridinyl, oxazolyl, oxadiazolyl, isoxazolyl, tetrahydrocyclopentapyrazolyl, imidazopyridinyl, indolyl, tetrahydropyrazolopyridinyl, dihydropyrrolopyrazolyl, pyridazinyl, pyrazolothiazolyl, piperazinyl, morpholinyl, and piperidinyl, wherein said $R^4$ is optionally substituted with one or more $R^7$ substituents, each $R^7$ substituent independently selected from F, Cl, Br, OH, oxo, $CF_3$, $OCF_3$, CN, $(C_1-C_6)$ alkyl, $O(C_1-C_4)$alkyl, $S(C_1-C_4)$alkyl, $C=O(C_1-C_4)$alkyl, $(C=O)NR^5R^6$, $(C=O)OR^5$, $(C_1-C_4)$alkynyl, $(C_3-C_6)$cycloalkyl, $O(C_3-C_6)$cycloalkyl, $C=O(C_3-C_6)$cycloalkyl, phenyl, indanyl, tetrahydronaphthalenyl, pyrazolyl, pyridinyl, oxazolyl, oxadiazolyl, isoxazolyl, tetrahydrocyclopentapyrazolyl, imidazopyridinyl, indolyl, tetrahydropyrazolopyridinyl, dihydropyrrolopyrazolyl, pyridazinyl, pyrazolothiazolyl, piperazinyl, morpholinyl, and piperidinyl, wherein $R^7$ is substituted with one or more $R^{12}$ selected from halogen, $(C_1-C_5)$alkyl, $CF_3$, OH and oxo.

In one embodiment of formula I, $R^{12}$ is selected from halogen, methyl and $CF_3$.

In one embodiment of formula I, $R^5$ and $R^6$ are each hydrogen.

In another embodiment of formula I, one of $R^5$ and $R^6$ is hydrogen and the other is $(C_1-C_4)$alkyl.

In another embodiment of formula I, z is 0, 1, or 2.

In another embodiment of formula I, z is 0 or 1.

In another embodiment of formula I, z is 0.

In another embodiment of formula I, $R^3$ is independently hydrogen, halogen. $(C_1-C_4)$haloalkyl, or $(C_1-C_4)$alkyl.

In another embodiment of formula I, two $R^3$ that are both attached to the same carbon atom of the piperidinyl ring join together to from a $(C_3-C_6)$cycloalkyl ring.

In another embodiment of formula I two $R^3$ that are attached to different carbon atoms of the piperidinyl ring join together to from a bridged ring.

In another embodiment of formula I, $R^1$ is H, F or methyl.

In another embodiment of formula I, $R^2$ is H, F or methyl.

In another embodiment of formula I, $R^1$ and $R^2$ optionally can come together to form a cyclopropyl, cyclobutyl, cyclopentyl or cyclohexyl ring wherein said ring may be optionally substituted with one or more substituents independently selected from OH, halogen, or $(C_1-C_4)$alkyl.

In another embodiment of formula I, $R^1$ and $R^2$ optionally can come together to form a cyclopropyl, cyclobutyl, cyclopentyl or cyclohexyl ring.

In another embodiment of formula I, $R^d$ and $R^e$ are each independently H or $(C_1-C_4)$alkyl.

In another embodiment of formula I, $R^f$ and $R^g$ are each independently H or $(C_1-C_4)$alkyl.

In another embodiment of formula I, $R^h$ is H or $(C_1-C_4)$ alkyl.

In another embodiment of formula I, $R^8$, is OH, $(C_1-C_4)$ alkyl, phenyl, pyridinyl, or isothiazolyl.

In another embodiment of formula I, $R^8$, is phenyl, pyridinyl, or isothiazolyl.

In another embodiment of formula I, $R^9$ is pyridinyl, tetrahydropyranyl, or phenyl.

In another embodiment of formula I, $R^{10}$ is methyl or hydroxy.

In another embodiment of formula I, m is 0, or 1.

In another embodiment of formula I, m is 1 or 2.

In another embodiment of formula I, m is 0 or 2.

In another embodiment of formula I, n is 0, or 1.

In another embodiment of formula I, n is 1 or 2.

In another embodiment of formula I, n is 0 or 2.

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of formula I. For example, different isotopic forms of hydrogen (H) include protium ($^1H$) and deuterium ($^2H$ or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within formula I can be prepared without undue experimentation by conventional techniques well known to those skilled in the art or by processes analogous to those described in the Schemes and Examples herein using appropriate isotopically-enriched reagents and/or intermediates.

Unless expressly stated to the contrary, all ranges cited herein are inclusive. For example, a heteroaryl ring described as containing from "1 to 3 heteroatoms" means the ring can contain 1, 2, or 3 heteroatoms. It is also to be understood that any range cited herein includes within its scope all of the sub-ranges within that range. The oxidized forms of the heteroatoms N and S are also included within the scope of the present invention.

It is understood by one skilled in the art that carbon atoms in organic molecules may often be replaced by silicon atoms to give analogous stable compounds. For example, carbon atoms in alkyl, cycloalkyl, aryl, heteroaryl, and heterocyclyl, groups may often be replaced by silicon atoms to provide stable compounds. All such compounds are within the scope of the present invention.

When any variable (for example, R) occurs more than one time in any constituent or in formula I or in any other formula depicting and describing compounds of the invention, its definition on each occurrence is independent of its definition at every other occurrence. Also, combinations of substituents and/or variables are permissible only if such combinations result in stable compounds.

The compounds of formula I may contain asymmetric or chiral centers, and, therefore, exist in different stereoisomeric forms. It is intended that all stereoisomeric forms of the compounds of formula I as well as mixtures thereof, including racemic mixtures, form part of the present invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by chromatography employing columns with a chiral stationary phase. Also, some of the compounds of formula I may be atropisomers (e.g., substituted biaryls) and are considered as part of this invention.

Certain of the compounds of the present invention can exist as tautomers. For the purposes of the present invention a reference to a compound of formula I is a reference to the compound per se, or to any one of its tautomers per se, or to mixtures of two or more tautomers.

The compounds of formula I may have the ability to crystallize in more than one form, a characteristic known as polymorphism, and it is understood that such polymorphic forms ("polymorphs") are within the scope of formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The invention includes within its scope all possible stoichiometric and non-stochiometric forms of the compounds of formula I.

The compounds of the present invention may have utility in preventing, treating, or ameliorating Alzheimer's disease. The compounds may also be useful in preventing, treating, or ameliorating other diseases mediated by the α7 nAChR, such as schizophrenia, sleep disorders, Parkinson's disease, autism, microdeletion syndrome, inflammatory diseases, cough, pain disorders (including acute pain, inflammatory pain and neuropathic pain) and cognitive disorders (including mild cognitive impairment). Other conditions that may be prevented, treated, or ameliorated by the compounds of the invention include pulmonary hypertension, chronic obstructive pulmonary disease (COPD), asthma, urinary incontinence, glaucoma, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, kidney diseases, cancer, and atherosclerosis.

In preferred embodiments, the compounds of the invention may be useful in preventing, treating, or ameliorating Alzheimer's disease, cognitive disorders, schizophrenia, cough, pain disorders and sleep disorders. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

Thus, in another specific embodiment, the present invention provides a method for preventing, treating, or ameliorating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington DC) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression; emotional/mood disorders; as well as sleep walking and enuresis; and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually anylesion at anylevel of the nervous system); postsurgical pain syndromes (eg, postmastectomy syndrome, postthoracotomy syndrome, stump pain); bone and joint pain (osteoarthritis); repetitive motion pain; dental pain; cancer pain; myofascial pain (muscular injury, fibromyalgia); perioperative pain (general surgery, gynecological); chronic pain; dysmennorhea, as well as pain associated with angina, and inflammatory pain of varied origins (e.g. osteoarthritis, rheumatoid arthritis, rheumatic disease, teno-synovitis and gout); headache; migraine and cluster headache; primary hyperalgesia; secondary hyperalgesia; primary allodynia; secondary allodynia; or other pain caused by central sensitization.

Potential conditions or disorders that have a strong inflammatory component for which the compounds of the invention may be useful include one or more of the following conditions or diseases: diabetes (systemic inflammation in diabetes marked by increases in blood cytokines e.g. IL-6 and TNFα which may lead to insulin resistance); asthma; arthritis; cystic fibrosis; sepsis; ulcerative colitis; inflammatory bowel disease; atherosclerosis; neuroinflammation associated with neurodegenerative diseases (e.g. Alzheimer's disease, Parkinson's disease, Creutzfeldt-Jacob disease, frontotemporal dementia, corticobasal degeneration, Pick's disease, progressive supranuclear palsy, traumatic brain injury, Huntington's disease, amyotrophic lateral sclerosis).

Cough disorders for which the compounds of the invention may be useful include: (a) acute cough associated with e.g. common cold, allergic rhinitis, acute bacterial sinusitis, exacerbation of chronic obstructive pulmonary disease, and *Bordetella pertussis* infection; (b) subacute cough associated with e.g. postinfection, *B. pertussis* infection, subacute bacterial sinusitis, and asthma; (c) chronic cough associated with e.g. postnasal-drip syndromes, nonallergic rhinitis, allergic rhinitis, vasomotor rhinitis, chronic bacterial sinusitis, asthma, gastroesophageal reflux disease, chronic bronchitis, angiotensin-converting enzyme inhibitors, and eosinophilic bronchitis.

Compounds of the invention may also be used to treat or prevent or ameliorate dyskinesia and protect against neurodegeneration in nigrostriatal neurons in Parkinson's disease. Furthermore, compounds of the invention may be used to decrease tolerance and/or dependence to opioid treatment of pain, and for treatment of withdrawal syndrome of e.g., alcohol, opioids, and cocaine.

The compounds of the present invention may be administered in the form of pharmaceutically acceptable salts. The term "pharmaceutically acceptable salt" refers to a salt that possesses the effectiveness of the parent compound and that is not biologically or otherwise undesirable (e.g., is neither toxic nor otherwise deleterious to the recipient thereof). Suitable salts include acid addition salts that may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1):1-19; P. Gould, *International J. of Pharmaceutics* (1986) 33:201-217; Anderson et al, *The Practice of Medicinal Chemistry* (1996), Academic Press, New York; and in *The Orange Book* (Food & Drug Administration, Washington, D.C. on their website).

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For the purposes of preventing, treating, or ameliorating the cognitive impairments in Alzheimer's disease, Parkinson's disease, schizophrenia, L-DOPA induced-dyskinesia, cough, and inflammation, the compounds of the present invention, optionally in the form of a salt, can be administered by any means that produces contact of the active agent with the agent's site of action. They can be administered by one or more conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following: orally, parenterally (including subcutaneous injections, intravenous, intramuscular, intrastemal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 18$^{th}$ edition (ed. A. It Gennaro, Mack Publishing Co., 1990).

The compounds of this invention can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, and 500 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, and the severity of the particular condition.

As noted above, the present invention also relates to a method of preventing, treating, or ameliorating the cognitive impairments in Alzheimer's disease, Parkinson's disease, schizophrenia, L-DOPA induced-dyskinesia, cough, and inflammation with a compound of the present invention in combination with one or more therapeutic agents and a pharmaceutical composition comprising a compound of the present invention and one or more therapeutic agents selected from the group consisting of anti-Alzheimer's Disease agents, for example beta-secretase inhibitors; MI mAChR agonist or PAMs; M4 mAChR agonists or PAMs; mGluR2 antagonists or NAMs or PAMs; ADAM 10 ligands or activators; gamma-secretase inhibitors, such as LY450139 and TAK 070; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; LRRK2 inhibitors; HMG-CoA reductase inhibitors; NSAIDs including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; N-methyl-D-aspartate (NMDA) receptor antagonists, such as memantine, neramexane and EVT101; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine H3 receptor antagonists such as ABT-834, ABT 829, GSK 189254 and CEP 16795; AMPA agonists or AMPA modulators, such as CX-717, LY 451395, LY404187 and S-18986; PDE IV inhibitors, including MEM1414, HT0712 and AVE8112; GABAA inverse agonists; GSK3D inhibitors, including AZD 1080, SAR502250 and CEP 16805; neuronal nicotinic agonists; selective MI agonists; HDAC inhibitors; and microtubule affinity regulating kinase (MARK) ligands; or other drugs that affect receptors or enzymes that either increase the efficacy, safety, convenience, or reduce unwanted side effects or toxicity of the compounds of the present invention.

Examples of combinations of the compounds of the instant invention include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the compounds of the instant invention may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride; COMT inhibitors such as entacapone, MAO-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the compound of the instant invention may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the compounds of the instant invention may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the compounds of the instant invention may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds of the instant invention include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED 160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGN XX/YY; neuronal nicotinic agonists, such as ABT894; NMDA receptor agonists or antagonists, such as AZD4282; NM antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

Compounds of the instant invention are useful for the treatment of moderate to severe dementia of the Alzheimer's type alone or in combination with an NMDA receptor antagonist, such as memantine, or in combination with an acetylcholinesterase inhibitor (AChEI) such as donepezil.

Compounds of the instant invention are useful for the treatment of mild to moderate dementia of the Alzheimer's type alone or in combination with either galantamine, rivastigmine, or donepezil.

Compounds of the instant invention are useful for the treatment of dementia associated with Parkinson's disease alone or in combination with rivastigmine.

Compounds of the instant invention are useful for the treatment of motor fluctuations in patients with advanced Parkinson's disease alone or in combination with carbidopa and levodopa.

Compounds of the instant invention are useful for the treatment of cough including acute, subacute, and chronic cough of various causes.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). A compound of the invention and an additional therapeutic agent may be present in fixed amounts (dosage amounts) in a single dosage unit (e.g., a capsule, a tablet and the like).

The α7 nAChR positive allosteric modulator (PAM) activity of the present compounds may be tested using assays known in the art. The α7 nAChR PAMs described herein have activities in an automated patch-clamp electrophysiology functional assay as described in the examples. The assay was performed using the IonFlux HT in a whole-cell, population patch configuration. See Golden et al. *Assay Drug Dev. Technol*. (2011) 9:608-619. The compounds were assessed for their ability to modulate the function of the human α7 nAChR stably expressed in a HEK cell line both in the presence, and in the absence of the natural α7 agonist acetylcholine. By performing a series of such measurements at different concentrations, the effective concentration of the α7 nAChR PAMs ($EC_{50}$) was determined. See Spencer et al. *Assay Drug Dev. Technol*. (2012) 10:313-324.

The present invention also includes processes for making compounds of formula I. The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice.

Reaction Schemes

The compounds of the present invention can be prepared readily according to the following schemes and specific examples, or modifications thereof, using readily available starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following schemes.

Many intermediates of the present invention may be prepared according to Scheme 1, in which an alkoxide, obtained by treating an alcohol with a strong base such as sodium hydride or potassium tert-butoxide in a polar aprotic solvent like DMF or THF, reacted with 2-fluoropyridine analogue 1.1 to give the corresponding ether 1.2.

SCHEME 1

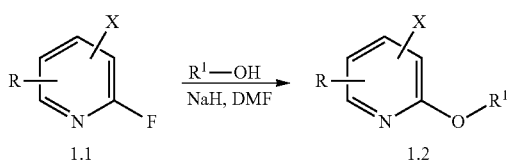

Other interesting intermediates may be prepared according to Scheme 2, in which an amine is treated with a strong base such as sodium hydride or potassium tert-butoxide in a polar aprotic solvent like DMF or THF to form the anion which then reacted with 2-fluoropyridine analogue 1.1 to give the corresponding amine 2.1.

SCHEME 2

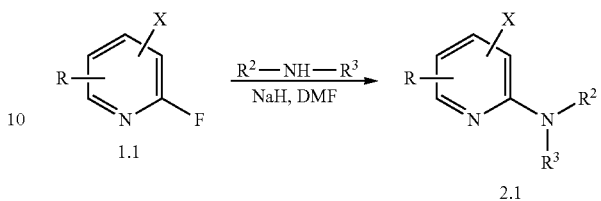

Spirocyclopropyl methylalcohol intermediates like 3.4 may be prepared according to Scheme 3. A Wittig-Homer reaction can be performed on N-protected piperidin-4-one 3.1 to generate piperidylidene acetate 3.2. Cyclopropanation may be carried out using trimethylsulfoxonium iodide in the presence of a base such as potassium tert-butoxide to provide compounds like 3.3 as a racemic mixture of isomers, or potentially as diastereoisomers (when Y is not H). Reduction of the ester group with reductants like DIBAL-H or lithium aluminum hydride gives the corresponding alcohol 3.4. The enantiomers or diastereoisomers may be separated by chiral chromatography.

SCHEME 3

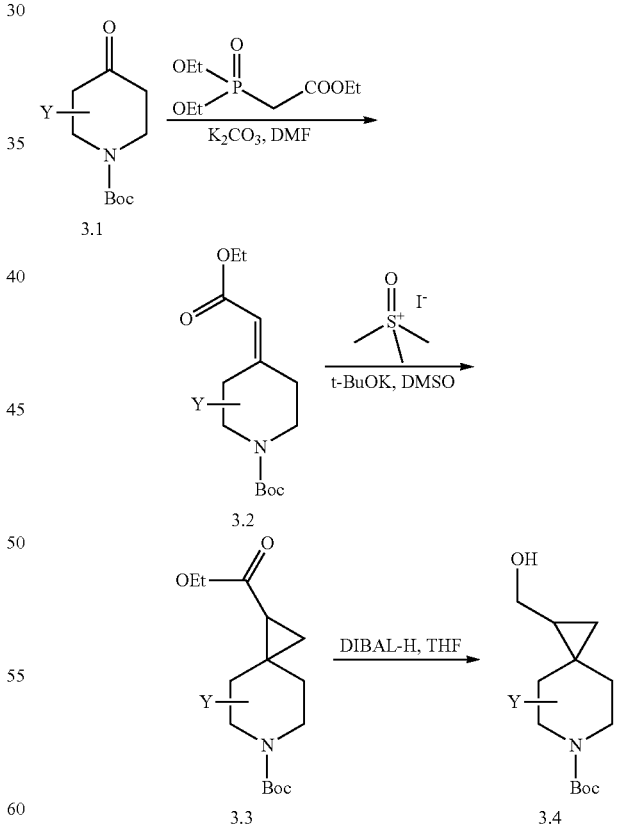

Difluorocyclopropyl alcohol intermediates may be prepared according to Scheme 4. The piperidylidene acetate 3.2 is reduced to piperidylidene methyl alcohol 4.1 using DIBAL-H and the alcohol may be acetylated to obtain the di-protected compound 4.2. Cyclopropanation is realized using Ruppert's reagent (TMS-CF$_3$) to afford 4.3 and deprotection under basic conditions affords compound 4.4. The isomers may be separated by chiral chromatography.

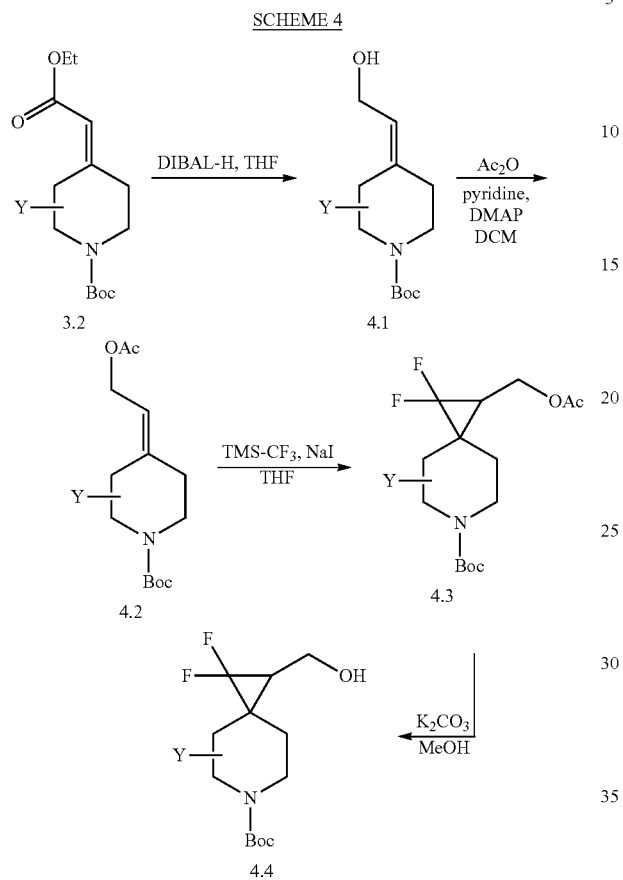

SCHEME 4

Intermediates like 5.2 may be prepared according to Scheme 5. The Mitsunobu coupling reaction between alcohol 5.1 and aryl or heteroaryl alcohols may be carried out in presence of an azodicarboxylate like DIAD, DEAD or ADDP, for example, and triphenylphosphine or polymer-supported triphenylphosphine to give the expected ether 5.2.

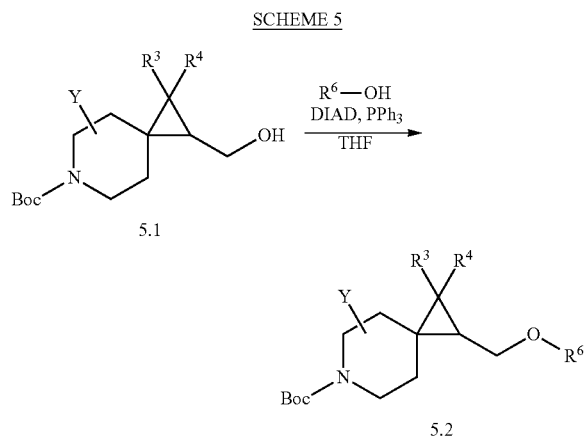

SCHEME 5

Another approach to the formation of key ether intermediates is illustrated in Scheme 6. Reaction of an alkoxide, obtained by treating alcohol 5.1 with a strong base such as sodium hydride or potassium tert-butoxide in a polar aprotic solvent like DMF or THF, with aryl, heteroaryl, or alkyl halide compounds R$^7$—X (wherein X=Cl, Br, or I) can be used to provide ether 6.1.

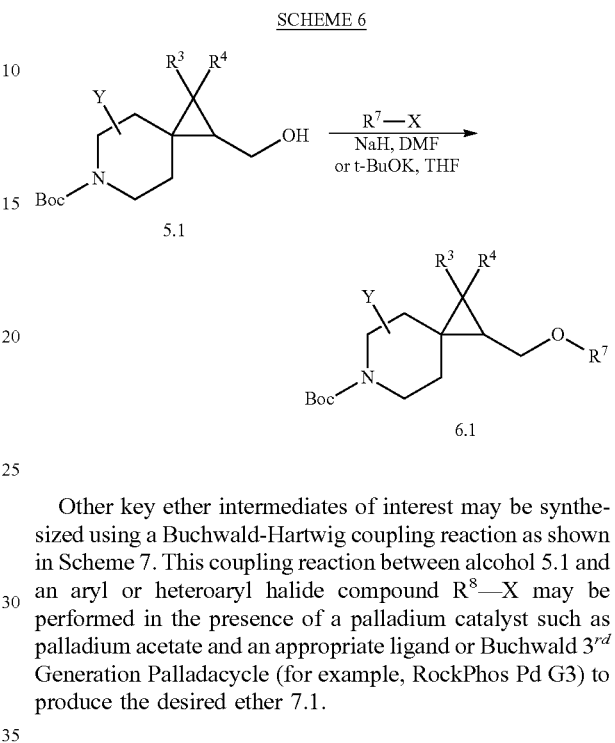

SCHEME 6

Other key ether intermediates of interest may be synthesized using a Buchwald-Hartwig coupling reaction as shown in Scheme 7. This coupling reaction between alcohol 5.1 and an aryl or heteroaryl halide compound R$^8$—X may be performed in the presence of a palladium catalyst such as palladium acetate and an appropriate ligand or Buchwald 3$^{rd}$ Generation Palladacycle (for example, RockPhos Pd G3) to produce the desired ether 7.1.

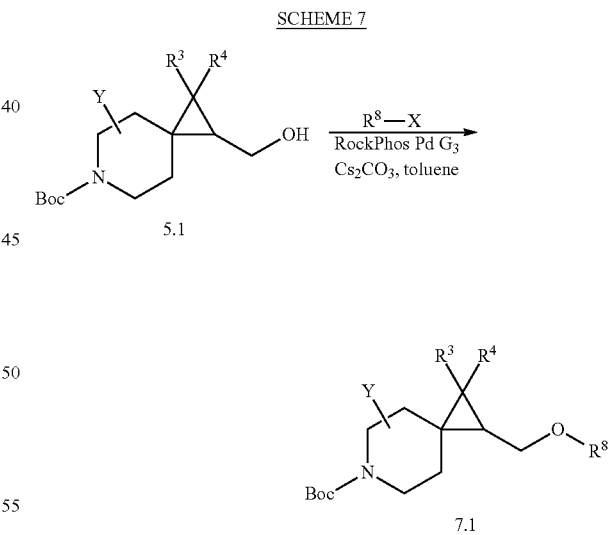

SCHEME 7

Ether intermediates like 5.2, 6.1 or 7.1 may be further elaborated by methodology known to those skilled in the art of organic synthesis. One approach, in which a second ether moiety is introduced, is illustrated in Scheme 8. The reaction of an alkoxide, obtained by treating alcohol R$^9$-OH with a strong base such as sodium hydride or potassium tert-butoxide in a polar aprotic solvent like DMF or THF, on an aryl, heteroaryl, or alkyl halide (X=halogen) like 8.1 can afford compound 8.2.

SCHEME 8

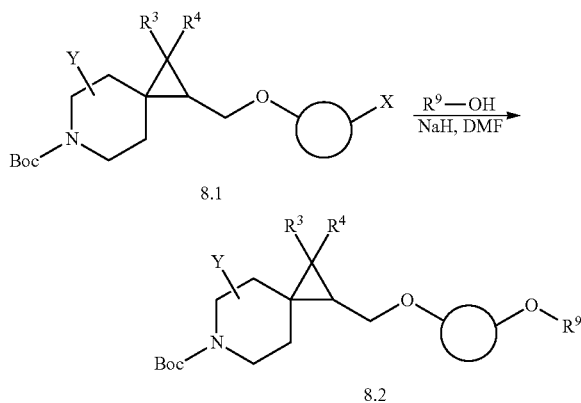

A related approach to the formation of disubstituted aryl or heteroaryl compounds is described in Scheme 9. The introduction of an alkyl, aryl or heteroarylamine is realized using a palladium catalyst like palladium acetate and an appropriate ligand (BINAP, for example) in the presence of a base such as cesium carbonate in a suitable solvent, such as 1,4-dioxane or toluene, to afford the amine-containing product 9.1.

SCHEME 9

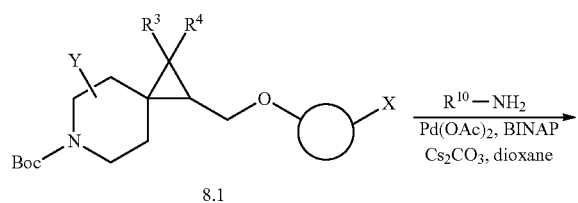

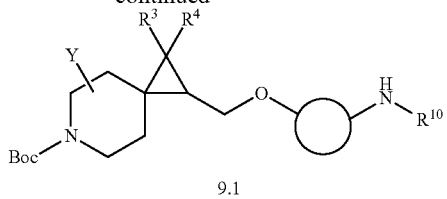

Other intermediates of the present invention may be prepared according to Scheme 10, in which ester 3.3 is reacted with an aluminum amide, formed by treating a suitable amine derivative with trimethylaluminum in dichloromethane, to give amides like 10.2. An alternative method to obtain amide 10.2 is to treat ester 3.3 with lithium hydroxide to afford the acid 10.1 which may be activated as an acid chloride using, for example, oxalyl chloride in the presence of catalytic DMF. Alternatively, activation of the acid can be realized using thionyl chloride, acetic anhydride, pivaloyl chloride or coupling reagents such as HBTU, DCC, EDC, T3P, HATU, HOBt, HOAt and their combinations, in presence of a suitable base. The activated acid can react with a variety of amine derivatives to give the final amide 10.2.

SCHEME 10

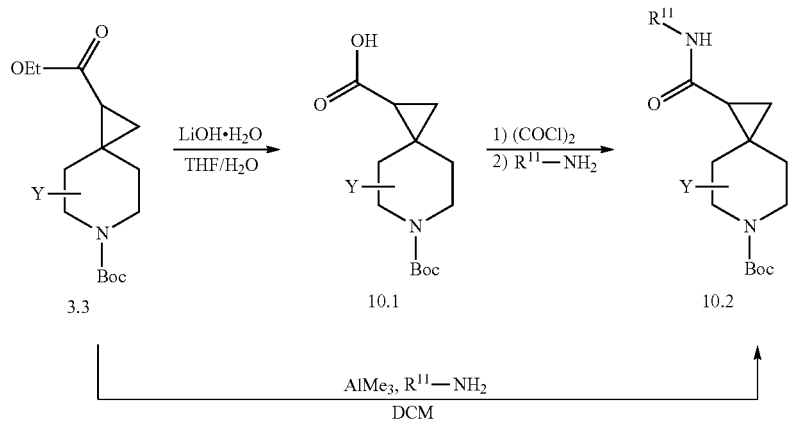

Additional intermediates of interest may be prepared according to Scheme 11 in which iodobenzene 11.1 is reacted with thiobenzoic acid to form the corresponding thioester 11.2. Deprotection of thioester 11.2 affords the corresponding thiol 11.3 which may be dimerized using iodine and the resulting disulfide 11.4 can then be reacted with alcohol 5.1 in the presence of tributylphosphine to provide thioether 11.5. An alternative route would be to use a Mitsunobu coupling reaction between alcohol 5.1 and an arylthiol or heteroarylthiol in the presence of an azodicarboxylate like DIAD, DEAD or ADDP, for example, and triphenylphosphine to give thioether 11.5.

SCHEME 11

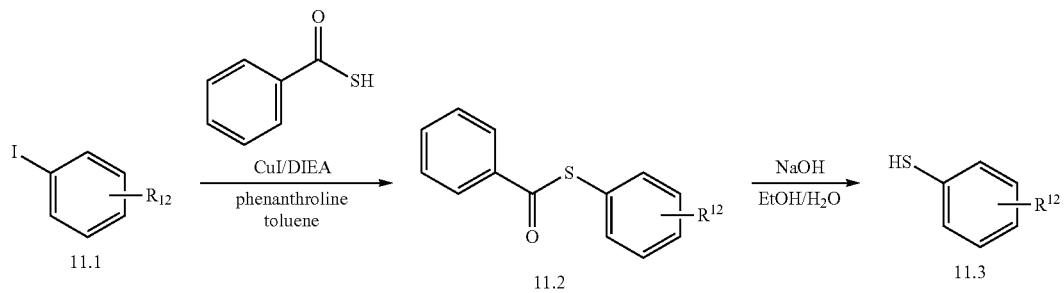

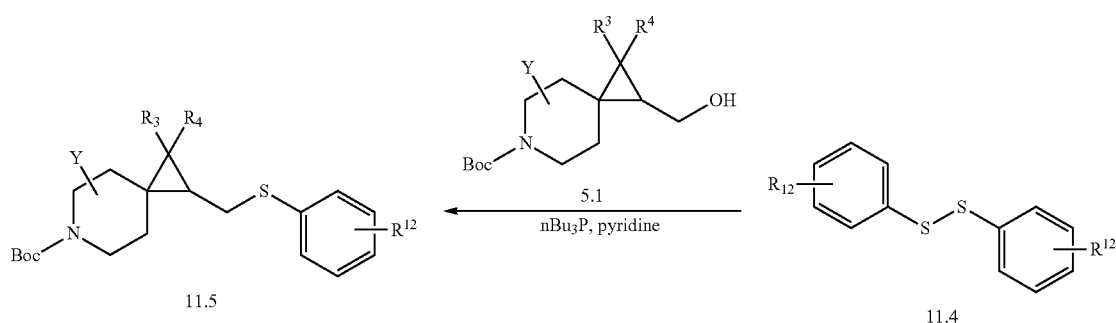

Many compounds of the present invention may be prepared according to Scheme 12, in which the N-tert-butyloxycarbonyl protecting group of spirocyclopropylpiperidine 12.1 is removed under standard conditions, such as the use of acids like HCl (hydrochloric acid) or TFA (trifluoroacetic acid), or other well-known reagents including trimethylsilyl iodide, trimethylsilyl triflate, or zinc bromide, to give the unprotected piperidine 12.2, which may be treated with sulfamide in 1,4-dioxane at elevated temperatures to afford final compound 12.3.

SCHEME 12

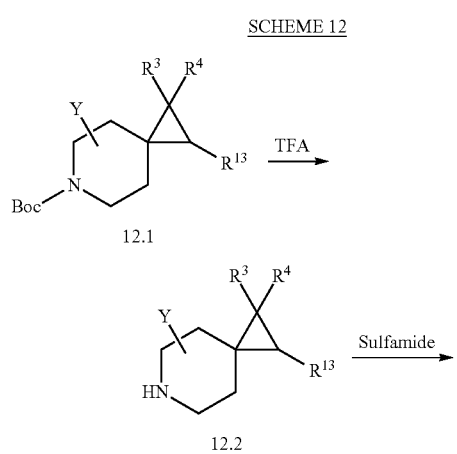

-continued

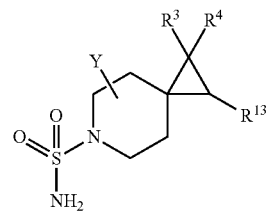

When the linker in $R_{13}$ is an amide, other compounds may be prepared as illustrated in Scheme 13, in which the amide 13.1 is reduced using borane tetrahydrofuran complex to afford amine 13.2.

SCHEME 13

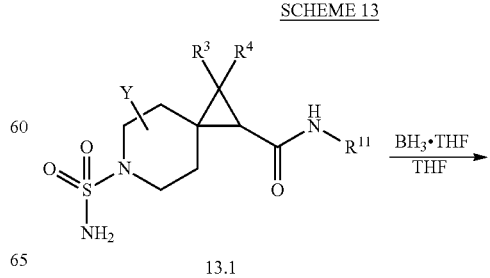

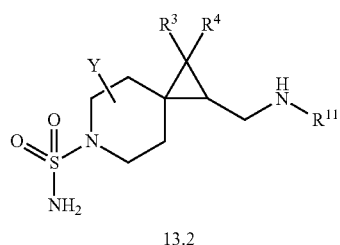

Additional compounds of the present invention may be prepared according to Scheme 14. The thioether 11.5 can be reacted with 3-chloroperbenzoic acid to give the sulfone derivative 14.1 as shown.

SCHEME 14

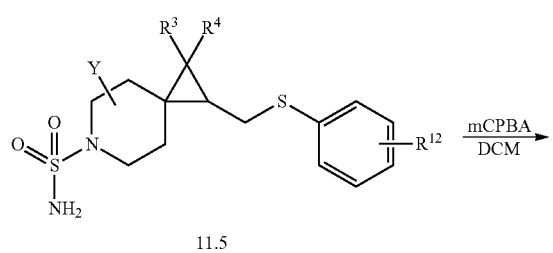

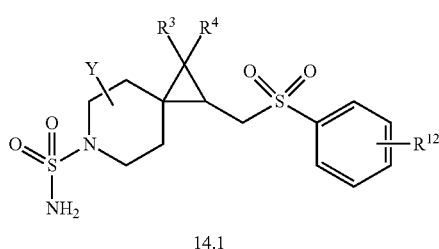

The synthesis of additional intermediates of interest is illustrated in Scheme 15. Oxidation of alcohol 5.1 to the corresponding aldehyde 15.1 may be conducted using Dess-Martin periodinane (DMP; 1,1,1-tris(acetyloxy)-1,1-dihydro-1,2-benziodoxol-3-(1H)-one) as the oxidizing agent. This oxidation may also be performed under a variety of other known conditions, for example using Swern oxidation methodology with oxalyl chloride, dimethyl sulfoxide, and triethylamine (see Mancuso & Swern, *Synthesis* (1981) 165-185). Classical Wittig methodology (see Maercker, *Org. React.* (1965) 14:270-490) may then be employed to react the aldehyde 15.1 with a suitable ylide, such as the triphenylphosphonium bromide shown in the scheme, to provide alkene 15.2. Catalytic hydrogenation of the alkene with a variety of catalysts, such as palladium or platinum on carbon, can be used to afford the corresponding alkane 15.3. Further elaboration of this intermediate may be performed according to the methodology shown in Scheme 12 to provide compounds of the present invention. Similarly, elaboration of alkene 15.2 according to Scheme 12 can provide additional compounds of the present invention.

SCHEME 15

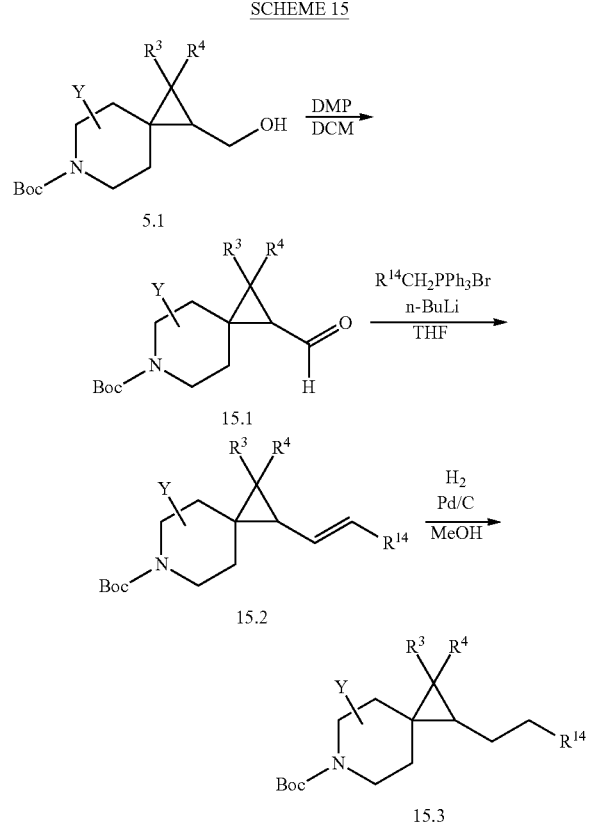

It is understood that the compounds and intermediates in the foregoing reaction schemes may be employed as synthetic intermediates in other schemes that involve similar intermediates to produce alternative compounds of the present invention.

In some cases, the order of carrying out the foregoing reaction schemes may be varied to facilitate the reaction or to avoid unwanted reaction products. Additionally, various protecting group strategies familiar to one skilled in the art of organic synthesis may be employed to facilitate the reaction or to avoid unwanted reaction products.

In some cases, the final product may be further modified, for example, by manipulation of substituents. These manipulations may include, but are not limited to, reduction, oxidation, alkylation, acylation, and hydrolysis reactions which are commonly known to those skilled in the art.

The following examples are provided so that the invention might be more fully understood. These examples are illustrative only and should not be construed as limiting the invention in any way. Wherein a racemic mixture is produced, the enantiomers may be separated using SFC reverse or normal phase chiral resolution conditions either after isolation of the final product or at a suitable Intermediate, followed by processing of the single isomers individually. It is understood that alternative methodologies may also be employed in the synthesis of these key intermediates and examples. Asymmetric methodologies (e.g. chiral catalysis, auxiliaries) may be used where possible and appropriate. The exact choice of reagents, solvents, temperatures, and other reaction conditions, depends upon the nature of the intended product.

Unless otherwise indicated, when ratios of compounds (such as for examples solvents) are given, the ratio is on a volume to volume basis. For example, a 20:80 mixture of ethyl acetate:hexanes means a mixture of 20 parts by volume ethyl acetate to 80 parts by volume of hexanes. Additionally, unless otherwise specifically indicated, all reagents are commercially available, known in the literature, or readily synthesized by one skilled in the art. Straightforward protecting group strategies were applied in some routes.

The following abbreviations are used throughout the text:

| | |
|---|---|
| Ac | Acetyl |
| ADDP | 1,1'-(azodicarbonyl)dipiperidine |
| app | Apparent |
| aq | Aqueous |
| Ar | Aryl |
| BINAP | 2,2'-bis(diphenylphosphino)-1,1'-binaphthalene |
| Bn | Benzyl |
| Boc | tert-butoxycarbonyl |
| br | Broad |
| Bu | Butyl |
| ca | circa (approximately) |
| Cbz | Carboxybenzyl |
| CDI | 1,1'-carbonyldiimidazole |
| d | Doublet |
| DCC | N,N'-dicyclohexylcarbodiimide |
| DCE | 1,2-dichloroethane |
| DCM | Dichloromethane |
| dd | doublet of doublets |
| DEAD | diethyl azodicarboxylate |
| Dess-Martin periodinane (DMP) | 1,1,1-Tris(acetyloxy)-1,1-dihydro-1,2-benziodoxol-3-(1H)-one |
| DIBAL (DIBAL-H) | diisobutylaluminum hydride |
| DIAD | diisopropyl azodicarboxylate |
| DIEA | N,N-diisopropylethylamine |
| DMAP | 4-(dimethylamino)pyridine |
| DMF | N,N-dimethylformamide |
| DMF-DMA | N,N-dimethylformamide dimethylacetal |
| DMSO | dimethylsulfoxide |
| EDC | N-(3-dimethylaminopropyl)-N'-ethylcarbodiimide hydrochloride |
| eq | Equivalents |
| ESI | electrospray ionization |
| Et | Ethyl |
| h | Hours |
| HATU | O-(7-azabenzotriazol-1-yl)-N,N,N'N'-tetramethyluronium hexafluorophosphate |
| HBTU | O-(benzotriazol-1-yl)-N,N,N'N'-tetramethyluronium hexafluorophosphate |
| HMDS | hexamethyldisilazane |
| HOAt | 1-hydroxy-7-azabenzotriazole |
| HOBt | 1-hydroxybenzotriazole |
| HPLC | high performance liquid chromatography |
| Hz | Hertz |
| i-Pr | Isopropyl |
| J | coupling constant |
| LAH | lithium aluminum hydride |
| LCMS | liquid chromatography-mass spectrometry |
| LDA | lithium diisopropylamide |
| m/z | mass to charge ratio |
| m | Multiplet |
| mCPBA | 3-chloroperoxybenzoic acid |
| Me | Methyl |
| min | Minutes |
| Ms | Methanesulfonyl |
| MW | molecular weight |
| n-BuLi | n-butyllithium |
| n-HexLi | n-hexyllithium |
| NMR | nuclear magnetic resonance |
| OAc | Acetate |
| p | Pentet |
| Pd/C | palladium on carbon |
| Ph | Phenyl |
| psi | pounds per square inch |
| p-Ts | 4-toluenesulfonyl |
| PTSA | 4-toluenesulfonic acid |
| Py | Pyridyl |
| q | Quartet |
| RockPhos | [(2-Di-tert-butylphosphino-3-methoxy-6-methyl- |
| Pd G3 | 2',4',6'-triisopropyl-1,1'-biphenyl)-2-(2-aminobiphenyl)]palladium(II) methanesulfonate |
| rt | ambient temperature |
| Ruppert's reagent | trimethyl(drifluoromethyl)silane |
| s | Singlet |
| SM | starting material |
| t | Triplet |
| td | triplet of doublets |
| T3P | propylphosphonic anhydride |
| t-Bu | tert-butyl |
| TCCA | trichloroisocyanuric acid |
| TEA | Triethylamine |
| TFA | trifluoroacetic acid |
| Tf | trifluoromethanesulfonyl |
| THF | Tetrahydrofuran |
| V/V | volume to volume |
| X-Phos | 2-dicyclohexylphosphino-2',4',6'-triisopropylbiphenyl |
| Xantphos | (9,9-dimethyl-9H-xanthene-4,5-diyl)bis(diphenylphosphane) |

INTERMEDIATE 1

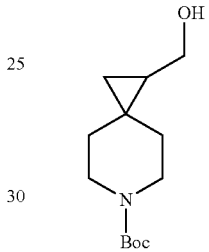

tert-Butyl 1-(hydroxymethyl)-6-azaspiro[2.5]octane-6-carboxylate

Step A: tert-Butyl 4-(2-ethoxy-2-oxoethylidene)piperidine-1-carboxylate

To a solution of tert-butyl 4-oxopiperidine-1-carboxylate (20.0 g, 0.100 mol) in DMF (200 mL) were added potassium carbonate (20.8 g, 0.150 mol) and triethyl phosphonoacetate (26.90 g, 0.120 mol) at ambient temperature. The reaction mixture was heated at 80° C. for 16 h then cooled to ambient temperature and cold water (600 mL) was added. The resulting precipitate was isolated by filtration, washed with water and dried under vacuum to afford the title compound. MS: m/z=170.1 [M-Boc+H].

Step B: 6-(tert-Butyl) 1-ethyl 6-azaspiro[2.5]octane-1,6-dicarboxylate

To a solution of trimethylsulfoxonium iodide (12.26 g, 55.7 mmol) in DMSO (50 mL) was added potassium tert-butoxide (6.25 g, 55.7 mmol). The resulting mixture was stirred at ambient temperature for 1 h then tert-butyl 4-(2-ethoxy-2-oxoethylidene)piperidine-1-carboxylate (5.00 g, 18.6 mmol) was added in several portions. The reaction mixture was stirred at ambient temperature for 18 h then saturated aqueous solution of ammonium chloride (200 mL) was added. The resulting mixture was extracted with ethyl acetate (3×300 mL). The organic layer was washed with a saturated aqueous solution of sodium chloride, dried over anhydrous sodium sulfate, filtered, and the filtrate was concentrated under reduced pressure. The residue was purified by silica gel chromatography, eluting with an isocratic mixture of ethyl acetate:petroleum ether 20:80 to afford the title compound. MS: m/z=184.1 [M-Boc+H].

Step C: tert-Butyl 1-(hydroxymethyl)-6-azaspiro[2.5]octane-6-carboxylate

To a stirred solution of 6-(tert-butyl) 2-ethyl 6-azaspiro[2.5]octane-2,6-dicarboxylate (20 g, 0.071 mol) in toluene (250 mL) at −78° C. was added dropwise a solution of DIBAL-H in toluene (1.0 N, 185 mL, 0.185 mol). The reaction mixture was stirred for 30 min at −78° C. then a saturated aqueous solution of ammonium chloride was added and the resulting mixture was allowed to warm to ambient temperature, and was filtered through a pad of Celite. The organic layer was washed with a saturated aqueous solution of sodium chloride, dried over anhydrous sodium sulfate, filtered, and the filtrate was concentrated under reduced pressure. The residue was purified by silica gel chromatography, eluting with an isocratic mixture of ethyl acetate:petroleum ether 20:80 to afford the title compound. MS: m/z=142.2 [M-Boc+H].

INTERMEDIATE 2

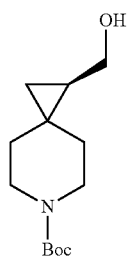

tert-Butyl (1R)-1-(hydroxymethyl)-6-azaspiro[2.5]octane-6-carboxylate

Racemic tert-butyl 1-(hydroxymethyl)-6-azaspiro[2.5]octane-6-carboxylate (Intermediate 1) was resolved by SFC, utilizing a ChiralPak® AD-H column (Chiral Technologies, Inc., West Chester, PA USA) and eluting with methanol:carbon dioxide—10:90. The first major peak to elute was tert-butyl (1R)-1-(hydroxymethyl)-6-azaspiro[2.5]octane-6-carboxylate, the title compound, and the second major peak to elute was tert-butyl (1S)-1-(hydroxymethyl)-6-azaspiro[2.5]octane-6-carboxylate. MS: m/z=142.2 [M-Boc+H].

INTERMEDIATE 3

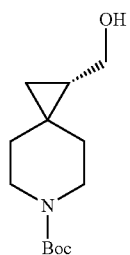

tert-Butyl (1S)-1-(hydroxymethyl)-6-azaspiro[2.5]octane-6-carboxylate

Racemic tert-butyl 1-(hydroxymethyl)-6-azaspiro[2.5]octane-6-carboxylate (Intermediate 1) was resolved by SFC, utilizing a ChiralPak® AD-H column and eluting with methanol:carbon dioxide—10:90. The first major peak to elute was tert-butyl (1R)-1-(hydroxymethyl)-6-azaspiro[2.5]octane-6-carboxylate and the second major peak to elute was tert-butyl (1S)-1-(hydroxymethyl)-6-azaspiro[2.5]octane-6-carboxylate, the title compound. MS: m/z=142.2 [M-Boc+H].

INTERMEDIATE 4

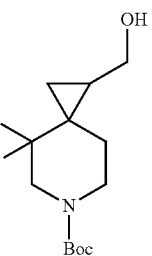

tert-Butyl 4,4-difluoro-1-(hydroxymethyl)-6-azaspiro[2.5]octane-6-carboxylate

Employing analogous procedures as described in Intermediate 1, but using tert-butyl 3,3-difluoro-4-oxopiperidine-1-carboxylate in place of tert-butyl 4-oxopiperidine-1-carboxylate, the title compound was obtained. MS: m/z=300.1 [M+Na].

INTERMEDIATE 5

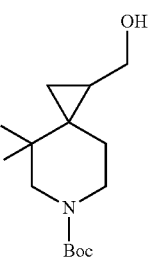

tert-Butyl 4,4-difluoro-1-(hydroxymethyl)-6-azaspiro[2.5]octane-6-carboxylate, enantiomer A Racemic tert-butyl 4,4-difluoro-1-(hydroxymethyl)-6-azaspiro[2.5]octane-6-carboxylate (Intermediate 4) was resolved by SFC, utilizing a ChiralPak® AD-H column and eluting with methanol:carbon dioxide—10:90. The first major peak to elute was tert-butyl 4,4-difluoro-1-(hydroxymethyl)-6-azaspiro[2.5]octane-6-carboxylate, enantiomer A, the title compound, and the second major peak to elute was tert-butyl 4,4-difluoro-1-(hydroxymethyl)-6-azaspiro[2.5]octane-6-carboxylate, enantiomer B. MS: m/z=300.1 [M+Na].

INTERMEDIATE 6

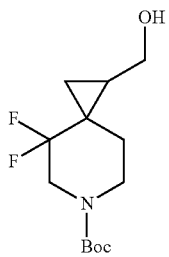

tert-Butyl 4,4-difluoro-1-(hydroxymethyl)-6-azaspiro[2.5]octane-6-carboxylate, Enantiomer B Racemic tert-butyl 4,4-difluoro-1-(hydroxymethyl)-6-azaspiro[2.5]octane-6-carboxylate (Intermediate 4) was resolved by SFC, utilizing a ChiralPak® AD-H column and eluting with methanol:carbon dioxide—10:90. The first major peak to elute was tert-butyl 4,4-difluoro-1-(hydroxymethyl)-6-azaspiro[2.5]octane-6-carboxylate, enantiomer A, and the second major peak to elute was tert-butyl 4,4-difluoro-1-(hydroxymethyl)-6-azaspiro[2.5]octane-6-carboxylate, enantiomer B, the title compound. MS: m/z=300.1 [M+Na].

INTERMEDIATE 7

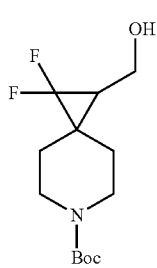

tert-Butyl 1,1-difluoro-2-(hydroxymethyl)-6-azaspiro[2.5]octane-6-carboxylate

Step A: tert-Butyl 4-(2-hydroxyethylidene)piperidine-1-carboxylate

To a solution of tert-butyl 4-(2-ethoxy-2-oxoethylidene)piperidine-1-carboxylate (described in Intermediate 1) (1.0 g, 3.71 mmol) in tetrahydrofuran (20 mL) at −70° C. was added a solution of diisobutylaluminum hydride in toluene (1.0 N, 7.75 mL, 7.75 mmol) over 10 min. The reaction mixture was stirred for 3 h at −70° C. and then a saturated aqueous solution of ammonium chloride (5 mL) was added dropwise and the mixture was stirred for 15 h while gradually warming to ambient temperature. The resulting mixture was poured into water (25 mL) and extracted with ethyl acetate (3×50 mL). The combined organic layers were washed with a saturated aqueous solution of sodium chloride, dried over anhydrous sodium sulfate, filtered, and the filtrate was concentrated under reduced pressure. The residue was purified by silica gel chromatography, eluting with a gradient of ethyl acetate:hexanes ranging from 0:100 to 100:0 to afford the title compound. MS: m/z=128.2 [M-Boc+H].

Step B: tert-Butyl 4-[2-(acetyloxy)ethylidene]piperidine-1-carboxylate

To a solution of tert-butyl 4-(2-hydroxyethylidene)piperidine-1-carboxylate (320 mg, 1.40 mmol) in dichloromethane (5 mL) at ambient temperature were added pyridine (0.227 mL, 2.80 mmol) and DMAP (17 mg, 0.14 mmol). The resulting mixture was then cooled to 0° C. and acetic anhydride (0.26 mL, 2.80 mmol) was added slowly. The reaction mixture was stirred at ambient temperature for 5 h, then diluted with dichloromethane (5 mL) and washed with an aqueous solution of copper(II) sulfate, then water, and then a saturated aqueous solution of sodium chloride. The organic layer was dried over sodium sulfate, filtered, concentrated under reduced pressure and the residue was purified by silica gel chromatography, eluting with a gradient of ethyl acetate:hexanes ranging from 0:100 to 50:50 to afford the title compound. MS: m/z=170.1 [M-Boc+H].

Step C: tert-Butyl 2-[(acetyloxy)methyl]-1,1-difluoro-6-azaspiro[2.5]octane-6-carboxylate To a solution of tert-butyl 4-[2-(acetyloxy)ethylidene]piperidine-1-carboxylate (100 mg, 0.37 mol) in dry tetrahydrofuran (5 mL), in a sealable vessel, was added NaI (28 mg, 0.19 mmol), followed by trimethyl(trifluoromethyl)silane (0.137 mL, 0.93 mmol). The reaction vessel was sealed and heated at 90° C. for 2 h then cooled to ambient temperature and NaI (28 mg, 0.19 mmol) and trimethyl(trifluoromethyl)silane (0.137 ml, 0.93 mmol) were added. The reaction mixture was heated at 90° C. for 2 h, then cooled to ambient temperature, diluted with water (10 mL) and extracted with ethyl acetate (3×10 mL). The combined organic extracts were dried over sodium sulfate, filtered, concentrated under reduced pressure and the residue was purified by silica gel chromatography, eluting with a gradient of ethyl acetate:hexanes ranging from 0:100 to 50:50 to afford the title compound. MS: m/z=220.1 [M-Boc+H].

Step D: tert-Butyl 1,1-difluoro-2-(hydroxymethyl)-6-azaspiro[2.5]octane-6-carboxylate To a solution of tert-butyl 2-[(acetyloxy)methyl]-1,1-difluoro-6-azaspiro[2.5]octane-6-carboxylate (580 mg, 1.73 mmol) in MeOH (100 mL) at ambient temperature was added potassium carbonate (751 mg, 5.19 mmol). The reaction mixture was vigorously stirred at ambient temperature for 16 h then diluted with ethyl acetate (300 mL), washed with water (50 mL), then with a saturated aqueous solution of sodium chloride (50 mL), dried over sodium sulfate, filtered, and the filtrate was concentrated under reduced pressure. The residue was purified by silica gel chromatography, eluting with a gradient of ethyl acetate:hexanes ranging from 0:100 to 50:50 to afford the title compound. MS: m/z=178.2 [M-Boc+H].

INTERMEDIATE 8

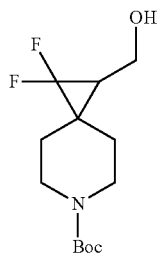

tert-Butyl 1,1-difluoro-2-(hydroxymethyl)-6-azaspiro[2.5]octane-6-carboxylate, Enantiomer A Racemic tert-butyl 1,1-difluoro-2-(hydroxymethyl)-6-azaspiro[2.5]octane-6-carboxylate (Intermediate 7) was resolved by SFC, utilizing a ChiralPak® AD-H column and eluting with methanol:carbon dioxide—10:90. The first major peak to elute was tert-butyl 1,1-difluoro-2-(hydroxymethyl)-6-azaspiro[2.5]octane-6-carboxylate, enantiomer A, the title compound, and the second major peak to elute was tert-butyl 1,1-difluoro-2-(hydroxymethyl)-6-azaspiro[2.5]octane-6-carboxylate, enantiomer B. MS: m/z=300.1 [M+Na].

INTERMEDIATE 9

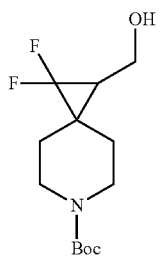

tert-Butyl 1,1-difluoro-2-(hydroxymethyl)-6-azaspiro[2.5]octane-6-carboxylate, Enantiomer B Racemic tert-butyl 1,1-difluoro-2-(hydroxymethyl)-6-azaspiro[2.5]octane-6-carboxylate (Intermediate 7) was resolved by SFC, utilizing a ChiralPak® AD-H column and eluting with methanol:carbon dioxide—10:90. The first major peak to elute was tert-butyl 1,1-difluoro-2-(hydroxymethyl)-6-azaspiro[2.5]octane-6-carboxylate, enantiomer A, and the second major peak to elute was tert-butyl 1,1-difluoro-2-(hydroxymethyl)-6-azaspiro[2.5]octane-6-carboxylate, enantiomer B, the title compound. MS: m/z=300.1 [M+Na].

INTERMEDIATE 10

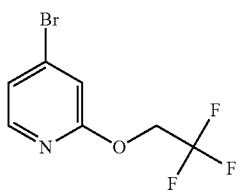

4-Bromo-2-(2,2,2-trifluoroethoxy)pyridine

To a solution of 2,2,2-trifluoroethanol (0.4 mL, 5.7 mmol) in DMF (20 mL) at 0° C. was added sodium hydride 60% oil dispersion (230 mg, 5.7 mmol). The reaction mixture was stirred at 0° C. for 45 min and 4-bromo-2-fluoropyridine (1.0 g, 5.7 mmol) was added. The reaction mixture was warmed to ambient temperature and stirred for 18 h. Water (50 mL) was added and the resulting mixture was extracted with ethyl acetate (3×50 mL). The combined organic extracts were washed with a saturated aqueous solution of sodium chloride, dried over magnesium sulfate, filtered, and the filtrate was concentrated under reduced pressure to afford the title compound in sufficient purity for use in the next step. MS: m/z=256.0/258.0 [M+H].

INTERMEDIATE 11

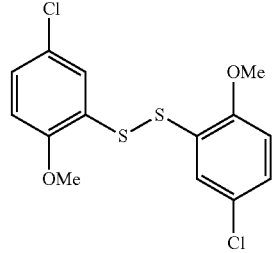

1,1'-Disultanediylbis(5-chloro-2-methoxybenzene)

Step A: S-(5-Chloro-2-methoxyphenyl) benzenecarbothioate

To a mixture of 4-chloro-2-iodoanisole (2.0 g, 7.45 mol), N,N-diisopropylethylamine (2.6 mL, 14.9 mmol), and 1,10-phenanthroline (270 mg, 1.49 mmol), in toluene (40 mL) in a sealable vessel was added CuI (143 mg, 0.75 mmol), followed by thiobenzoic acid (0.88 mL, 7.45 mmol). The reaction vessel was sealed and heated at 110° C. for 18 h. After cooling to ambient temperature, the reaction mixture was diluted in dichloromethane (50 mL), adsorbed on silica gel, and purified by silica gel chromatography, eluting with a gradient of ethyl acetate:hexanes ranging from 0:100 to 20:80 to afford the title compound. $^1$H NMR (300 MHz, CDCl$_3$) δ 8.03 (d, J=9.0 Hz, 2H); 7.61 (t, J=7.3 Hz, 1H); 7.57-7.42 (m, 3H); 7.40 (dd, J=8.8 Hz, 2.6 Hz, 1H); 6.94 (d, J=8.8 Hz, 1H); 3.84 (s, 3H).

Step B: 5-Chloro-2-methoxy-benzenethiol

To a solution of S-(5-chloro-2-methoxyphenyl) benzenecarbothioate (1.94 g, 6.96 mmol) in ethanol (100 mL) at 0° C. was added an aqueous solution of sodium hydroxide (1.0 N, 20.8 mL, 20.8 mmol) dropwise. The reaction mixture was stirred at ambient temperature for 18 h then acidified to pH=4 using an aqueous solution of hydrochloric acid (1.0 N), and most of the organic solvent was removed under reduced pressure. The resulting mixture was extracted with ethyl acetate (3×50 mL) and the combined organic extracts were dried over magnesium sulfate, filtered, concentrated under reduced pressure and the residue was purified by silica gel chromatography, eluting with a gradient of ethyl acetate:hexanes ranging from 0:100 to 10:90 to afford the title compound. $^1$H NMR (300 MHz, CDCl$_3$) δ 7.22 (d, J=2.5 Hz, 1H); 7.06 (dd, J=8.7 Hz, 2.5 Hz, 1H); 6.75 (d, J=8.7 Hz, 1H); 3.87 (s, 3H).

Step C: 1,1'-Disulfanediylbis(5-chloro-2-methoxybenzene)

To a solution of 5-chloro-2-methoxy-benzenethiol (840 mg, 4.8 mmol) in ethanol (20 mL) at ambient temperature was added a solution of iodine (1.7 g, 6.7 mmol) in ethanol (20 mL) dropwise. The reaction mixture was stirred for 10 min and partially concentrated under reduced pressure. The residue was diluted with ethyl acetate (50 mL), washed with a saturated aqueous solution of sodium thiosulfate (2×25 mL), then a saturated aqueous solution of sodium chloride (20 mL), dried over magnesium sulfate, filtered, and the filtrate was concentrated under reduced pressure to afford the title compound in sufficient purity for use in the next step. $^1$H NMR (300 MHz, CDCl$_3$) δ 7.52 (d, J=2.5 Hz, 1H); 7.15 (dd, J=8.7 Hz, 2.5 Hz, 1H); 6.77 (d, J=8.7 Hz, 1H); 3.89 (s, 3H).

INTERMEDIATE 12

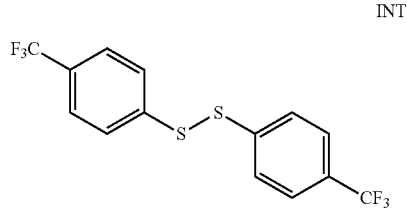

1,1'-Disultanediylbis[4-(trifluoromethyl)benzene]

Following similar procedures to those described in Intermediate 11, but using 4-(trifluoromethyl)iodobenzene in place of 4-chloro-2-iodoanisole, the title compound was obtained. $^1$H NMR (300 MHz, DMSO-d$_6$) δ 7.81-7.65 (m, 8H).

INTERMEDIATE 13

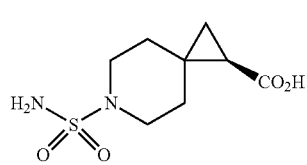

(1R)-6-Sulfamoyl-6-azaspiro[2.5]octane-1-carboxylic Acid

Step A: Ethyl (1R)-6-azaspiro[2.5]octane-1-carboxylate

To a solution of 6-benzyl 1-ethyl (1R)-6-azaspiro[2.5]octane-1,6-dicarboxylate (44.6 g, 141 mmol) (Brown et al. *J. Med. Chem.* (2014) 57:733-758) in methanol (400 mL) was added palladium hydroxide (20 wt. %, on activated carbon, 4.94 g, 7.03 mmol). The reaction vessel was evacuated and backfilled with hydrogen (ca. 1 atm) and the reaction mixture was allowed to stir at ambient temperature for 18 h. The reaction mixture was filtered through a pad of Celite®, washing with methanol, and the filtrate was concentrated under reduced pressure to afford the title compound for use in the next step. MS: m/z=184.3 [M+H].

Step B: Ethyl (1R)-6-sulfamoyl-6-azaspiro[2.5]octane-1-carboxylate

To a solution of ethyl (1R)-6-azaspiro[2.5]octane-1-carboxylate (25.6 g, 140 mmol) in 1,4-dioxane (400 mL) was added sulfamide (40.7 g, 423 mmol) and the reaction mixture warmed to 95° C. and allowed to stir for 18 h. Sulfamide (9.00 g, 93.7 mmol) was added and the reaction mixture was warmed to 100° C. and allowed to stir for 6 h. The reaction mixture was allowed to cool to ambient temperature, poured into a saturated aqueous solution of sodium bicarbonate, and extracted with ethyl acetate (2×). The combined organic extracts were washed with a saturated aqueous solution of sodium chloride, dried (sodium sulfate) and filtered and the filtrate was concentrated under reduced pressure. The crude residue was purified by silica gel chromatography, eluting with a gradient of methanol:dichloromethane ranging from 0:100 to 5:95 to afford the title compound. MS: m/z=263.1 [M+H].

Step C: (1R)-6-Sulfamoyl-6-azaspiro[2.5]octane-1-carboxylic Acid

To a solution of ethyl (1R)-6-sulfamoyl-6-azaspiro[2.5]octane-1-carboxylate (50.0 g, 191 mmol) in tetrahydrofuran (270 mL) and methanol (135 mL) was added an aqueous solution of sodium hydroxide (2 M, 286 mL, 572 mmol) and the reaction mixture was allowed to stir for 2 days at ambient temperature. The reaction mixture was diluted with ice water (200 mL) and the resulting mixture slowly adjusted to pH=5 with an aqueous solution of hydrochloric acid (12 M) and extracted with ethyl acetate (3×). The combined organic extracts were washed with a saturated aqueous solution of sodium chloride, dried (sodium sulfate), and filtered and the filtrate was concentrated under reduced pressure to afford the title compound in sufficient purity for use in the next step. MS: m/z=235.1 [M+H].

INTERMEDIATE 14

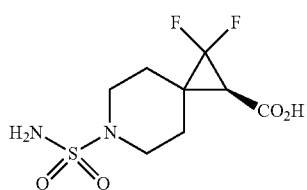

(1R)-2,2-Difluoro-6-sulfamoyl-6-azaspiro[2.5]octane-1-carboxylic Acid

Step A: tert-Butyl 4-(2-methoxy-2-oxoethylidene)piperidine-1-carboxylate

To a solution of tert-butyl 4-oxopiperidine-1-carboxylate (8.40 g, 42.2 mmol) in toluene (100 mL) was added methyl 2-(triphenylphosphoranylidene)acetate (17.6 g, 52.7 mmol) and the reaction mixture was warmed to 110° C. and allowed to stir for 4 h. The reaction mixture was cooled to ambient temperature and concentrated under reduced pressure. Hexanes were added to the residue and the resulting mixture filtered, washing with hexanes, and the filtrate was concentrated under reduced pressure. The residue was purified by silica gel chromatography, eluting with a gradient of hexanes:ethyl acetate ranging from 100:0 to 50:50 to afford the title compound. MS: m/z=200.1 [M-tBu+H].

Step B: tert-Butyl 4-(2-hydroxyethylidene)piperidine-1-carboxylate

To a solution of tert-butyl 4-(2-methoxy-2-oxoethylidene)piperidine-1-carboxylate (7.54 g, 29.5 mmol) in tetrahydrofuran (60 mL) at −78° C. was added a solution of diisobutylammonium hydride in tetrahydrofuran (1 M, 60.0 mL, 60.0 mmol) dropwise and the reaction mixture was allowed to stir for 1 h at −78° C. The reaction mixture was allowed to warm to 0° C. and stir for 1 h. A solution of diisobutylammonium hydride in tetrahydrofuran (1 M, 40.0 mL, 40.0 mmol) was added dropwise and the reaction mixture was allowed to stand at 0° C. for 18 h. An aqueous solution of Rochelle's salt (0.5 M) was added slowly and the resulting mixture was diluted with water and extracted with ethyl acetate (2×). The combined organic extracts were washed with a saturated aqueous solution of sodium chloride, dried (magnesium sulfate) and filtered and the filtrate was concentrated under reduced pressure to afford the title compound in sufficient purity for use in the next step. MS: m/z=195.2 [M+Na-tBu].

Step C: tert-Butyl 4-(2-acetoxyethylidene)piperidine-1-carboxylate

To a solution of tert-butyl 4-(2-hydroxyethylidene)piperidine-1-carboxylate (5.80 g, 25.5 mmol) in dichloromethane (100 mL) were added pyridine (4.13 mL, 51.0 mmol), 4-dimethylaminopyridine (0.312 g, 2.55 mmol), and acetic anhydride (4.82 mL, 51.0 mmol) sequentially and the reaction mixture was allowed to stir for 2 h at ambient temperature. The reaction mixture was concentrated under reduced pressure and the residue was purified by silica gel chromatography, eluting with a gradient of hexanes:ethyl acetate ranging from 100:0 to 25:75 to afford the title compound. MS: m/z=292.2 [M+Na].

Step D: tert-Butyl 2-(acetoxymethyl)-1,1-difluoro-6-azaspiro[2.5]octane-6-carboxylate To a solution of tert-butyl 4-(2-acetoxyethylidene)piperidine-1-carboxylate (3.23 g, 12.0 mmol) in tetrahydrofuran (30 mL) in a sealable vessel under an atmosphere of nitrogen were added sodium iodide (0.899 g, 6.00 mmol) and trimethyl(trifluoromethyl)silane (4.43 mL, 30.0 mmol) sequentially. The vessel was sealed and the reaction mixture was warmed to 90° C. and allowed to stir for 2 h. The reaction mixture was cooled to ambient temperature, sodium iodide (0.899 g, 6.00 mmol) and trimethyl(trifluoromethyl)silane (4.43 mL, 30.0 mmol) were added, and the reaction mixture was warmed to 90° C. and allowed to stir for 2 h. The reaction mixture was allowed to cool to ambient temperature, diluted with water, and the resulting mixture extracted with ethyl acetate. The organic layer was concentrated under reduced pressure and the residue was purified by silica gel chromatography, eluting with a gradient of hexanes:ethyl acetate ranging from 100:0 to 50:50 to afford the title compound. MS: m/z=264.1 [M-tBu+H].

Step E: tert-Butyl 1,1-difluoro-2-(hydroxymethyl)-6-azaspiro[2.5]octane-6-carboxylate To a solution of tert-butyl 2-(acetoxymethyl)-1,1-difluoro-6-azaspiro[2.5]octane-6-carboxylate (5.68 g, 17.8 mmol) in methanol (50 mL) was added potassium carbonate (7.37 g, 53.4 mmol) and the reaction mixture was allowed to stir for 2 h at ambient temperature. The reaction mixture was filtered, washing with methanol, and the filtrate was concentrated under reduced pressure. Ethyl acetate and water were added, the layers separated, and the aqueous layer was adjusted to pH=5 and extracted with ethyl acetate. The organic extract was dried (magnesium sulfate) and filtered and the filtrate was concentrated under reduced pressure to afford the title compound in sufficient purity for use in the next step. MS: m/z=222.1 [M-tBu+H].

Step F: 6-(tert-Butoxycarbonyl)-2,2-difluoro-6-azaspiro[2.5]octane-1-carboxylic Acid To a solution of tert-butyl 1,1-difluoro-2-(hydroxymethyl)-6-azaspiro[2.5]octane-6-carboxylate (4.93 g, 17.9 mmol) in acetonitrile (100 mL) were added 4-methylmorpholine-4-oxide hydrate (24.0 g, 178 mmol) and tetrapropylammonium perruthenate (0.625 g, 1.78 mmol) sequentially and the reaction mixture was allowed to stir for 2 h at ambient temperature. The reaction mixture was diluted with an aqueous solution of hydrochloric acid (1 M) and extracted with ethyl acetate. The aqueous layer was diluted with water and a saturated aqueous solution of sodium chloride, extracted with ethyl acetate, and the combined organic extracts filtered over a pad of Celite® and concentrated under reduced pressure to afford the title compound in sufficient purity for use in the next step. MS: m/z=236.1 [M-tBu+H].

Step G: 1-Benzyl 6-tert-butyl 2,2-difluoro-6-azaspiro[2.5]octane-1,6-dicarboxylate To a solution of 6-(tert-butoxycarbonyl)-2,2-difluoro-6-azaspiro[2.5]octane-1-carboxylic acid (5.18 g, 17.9 mmol) in N,N-dimethylformamide (100 mL) were added HATU (10.1 g, 26.7 mmol), benzyl alcohol (2.77 mL, 26.7 mmol), and diisopropylethylamine (9.32 mL, 53.3 mmol) sequentially and the reaction mixture was allowed to stir for 1 h at ambient temperature. The reaction mixture was diluted with water and extracted with ethyl acetate (2×). The combined organic extracts were dried (magnesium sulfate) and filtered and the filtrate was concentrated under reduced pressure. The residue was purified by silica gel chromatography, eluting with a gradient of hexanes:ethyl acetate ranging from 100:0 to 50:50 to afford the title compound. MS: m/z=326.2 [M-tBu+H].

Step H: Benzyl 2,2-difluoro-6-azaspiro[2.5]octane-1-carboxylate hydrochloride

To a solution of 1-benzyl 6-tert-butyl 2,2-difluoro-6-azaspiro[2.5]octane-1,6-dicarboxylate (4.70 g, 12.3 mmol) in ethyl acetate (25 mL) was added a solution of hydrogen chloride in 1,4-dioxane (4 M, 12.3 mL, 49.3 mmol) and the reaction mixture was allowed to stir for 18 h at ambient temperature. The reaction mixture was concentrated under reduced pressure to afford the title compound in sufficient purity for use in the next step. MS: m/z=282.2 [M+H].

Step I: (1R)-Benzyl 2,2-difluoro-6-sulfamoyl-6-azaspiro[2.5]octane-1-carboxylate To a solution of benzyl 2,2-difluoro-6-azaspiro[2.5]octane-1-carboxylate hydrochloride (3.92 g, 12.3 mmol) in 1,4-dioxane (60 mL) were added triethylamine (2.58 mL, 18.5 mmol) and sulfamide (3.56 g, 37.0 mmol) and the reaction mixture was warmed to 90° C. and allowed to stir for 4 h. The reaction mixture was cooled to ambient temperature and sulfamide (3.56 g, 37.0 mmol) was added. The reaction mixture was warmed to 90° C. and allowed to stir for 4 h. The reaction mixture was concentrated under reduced pressure and ethyl acetate and water were added to the residue. The aqueous layer was extracted with ethyl acetate and the combined organic extracts were dried (magnesium sulfate) and filtered and the filtrate was concentrated under reduced pressure. The residue was purified by silica gel chromatography, eluting with a gradient of hexanes:ethyl acetate:ethanol ranging from 100:0:0 to 52:36:12 to afford the racemic title compound. The racemate was resolved by SFC, utilizing a ChiralPak® AD-H column and eluting with methanol:carbon dioxide—40:60. The first major peak to elute was (1R)-benzyl 2,2-difluoro-6-sulfamoyl-6-azaspiro

[2.5]octane-1-carboxylate, the title compound, and the second major peak to elute was (1S)-benzyl 2,2-difluoro-6-sulfamoyl-6-azaspiro[2.5]octane-1-carboxylate. MS: m/z=361.2 [M+H].

Step J: (1R)-2,2-Difluoro-6-sulfamoyl-6-azaspiro [2.5]octane-1-carboxylic Acid

To a vessel containing (1R)-benzyl 2,2-difluoro-6-sulfamoyl-6-azaspiro[2.5]octane-1-carboxylate (1.20 g, 3.33 mmol) was added palladium on activated carbon (10% w/w, 0.354 g, 0.333 mmol) under an inert atmosphere. Methanol (17 mL) was added and the reaction mixture was placed under an atmosphere of hydrogen (ca. 1 atm) and allowed to stir for 3 h at ambient temperature. The reaction mixture was filtered over a pad of Celite®, washing with methanol, and the filtrate was concentrated under reduced pressure to afford the title compound in sufficient purity for use in the next step. MS: m/z=271.1 [M+H].

INTERMEDIATE 15

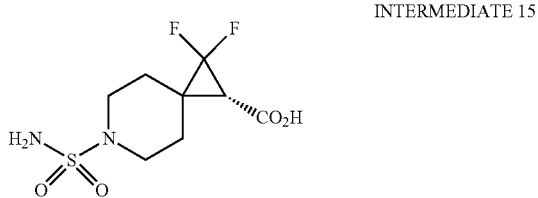 [SMILES: NS(=O)(=O)N1CCC2(CC1)[C@@H](C(=O)O)C2(F)F]

(1S)-2,2-Difluoro-6-sulfamoyl-6-azaspiro[2.5]octane-1-carboxylic Acid

Following analogous procedures as described in Intermediate 14, but using (1S)-benzyl 2,2-difluoro-6-sulfamoyl-6-azaspiro[2.5]octane-1-carboxylate (described in Intermediate 14) in place of (1R)-benzyl 2,2-difluoro-6-sulfamoyl-6-azaspiro[2.5]octane-1-carboxylate, the title compound was obtained. MS: m/z=271.1 [M+H].

INTERMEDIATE 16

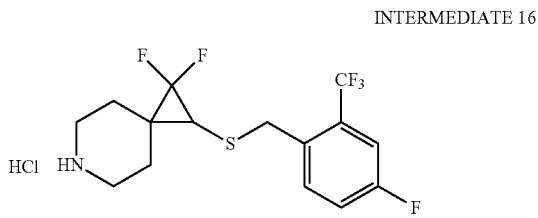 [SMILES: Cl ; Fc1ccc(CCC2C(F)(F)C23CCNCC3)c(C(F)(F)F)c1]

1,1-Difluoro-2-({[4-fluoro-2-(trifluoromethyl)phenyl]sulfanyl}methyl)-6-azaspiro[2.5]octane Hydrochloride Step A: tert-Butyl 1,1-difluoro-2-({[(4-methylphenyl)sulfonyl]oxy}methyl)-6-azaspiro[2.5]octane-6-carboxylate To a solution of tert-butyl 1,1-difluoro-2-(hydroxymethyl)-6-azaspiro[2.5]octane-6-carboxylate (Intermediate 7) (500 mg, 1.80 mmol) in dichloromethane (10 mL) were added triethylamine (0.50 mL, 3.61 mmol), 4-toluenesulfonyl chloride (516 mg, 2.70 mmol), and DMAP (22 mg, 0.18 mmol), and the reaction mixture was stirred at ambient temperature for 4 h then warmed to 35° C. and allowed to stir for 16 h. The resulting mixture was poured into water (20 mL) and extracted with dichloromethane (3×30 mL). The combined organic layers were washed with a saturated aqueous solution of sodium chloride, dried over anhydrous sodium sulfate, filtered, and the filtrate was concentrated under reduced pressure. The residue was purified by silica gel chromatography, eluting with a gradient of ethyl acetate:petroleum ether ranging from 0:100 to 15:85 to afford the title compound. MS: m/z=375.9 [M-tBu+H].

Step B: tert-Butyl 1,1-difluoro-2-({[4-fluoro-2-(trifluoromethyl)phenyl]sulfanyl}methyl)-6-azaspiro [2.5]octane-6-carboxylate To a solution of tert-butyl 1,1-difluoro-2-({[(4-methylphenyl)sulfonyl]oxy}methyl)-6-azaspiro[2.5]octane-6-carboxylate (100 mg, 0.232 mmol) in 1,4-dioxane (10 mL) were added 4-fluoro-2-(trifluoromethyl)benzenethiol (68 mg, 0.35 mmol), and 1,8-diazabicyclo[5.4.0]undec-7-ene (0.050 mL, 0.33 mmol), and the reaction mixture was stirred at ambient temperature for 16 h. The resulting mixture was poured into water (20 mL) and extracted with ethyl acetate (3×30 mL). The combined organic layers were washed with a saturated aqueous solution of sodium chloride, dried over anhydrous sodium sulfate, filtered, and the filtrate was concentrated under reduced pressure. The residue was purified by silica gel chromatography, eluting with a gradient of ethyl acetate:petroleum ether ranging from 0:100 to 10:90 to afford the title compound. MS: m/z=440.9 [M-tBu+CH$_3$CN+H].

Step C: 1,1-Difluoro-2-({[4-fluoro-2-(trifluoromethyl)phenyl]sulfanyl}methyl)-6-azaspiro[2.5]octane Hydrochloride To a solution of 6-tert-butyl 1,1-difluoro-2-({[4-fluoro-2-(trifluoromethyl)phenyl]sulfanyl}methyl)-6-azaspiro[2.5]octane-6-carboxylate (180 mg, 0.40 mmol) in ethyl acetate (10 mL) was added a solution of hydrogen chloride in 1,4-dioxane (4 M, 10 mL, 40 mmol) and the reaction mixture was allowed to stir for 6 h at ambient temperature. The reaction mixture was concentrated under reduced pressure to afford the title compound in sufficient purity for use in the next step. MS: m/z=355.9 [M+H].

INTERMEDIATE 17

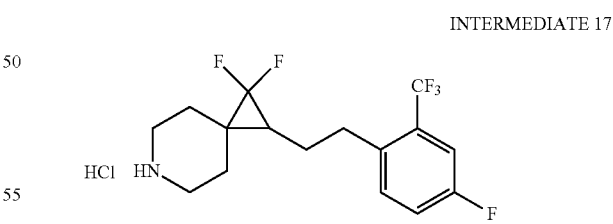

1,1-Difluoro-2-{2-[4-fluoro-2-(trifluoromethyl)phenyl]ethyl}-6-azaspiro[2.5]octane Hydrochloride Step A: tert-Butyl 1,1-difluoro-2-formyl-6-azaspiro [2.5]octane-6-carboxylate To a stirred solution of tert-butyl 1,1-difluoro-2-(hydroxymethyl)-6-azaspiro[2.5]octane-6-carboxylate (Intermediate 7) (760 mg, 2.74 mmol) in dichloromethane (10 mL) was added Dess-Martin periodinane (2.33 g, 5.48 mmol), and the reaction mixture was stirred at ambient temperature for 2 h. A saturated aqueous solution of sodium bicarbonate (20 mL) was added slowly and the resulting mixture was extracted with dichloromethane (3×10 mL). The combined organic layers were dried over anhydrous sodium sulfate, filtered, and the filtrate was concentrated under reduced pressure. The residue was purified by silica gel chromatography, eluting with a gradient of ethyl acetate: petroleum ether ranging from 0:100 to 10:90 to afford the title compound. MS: m/z=220.1 [M+H].

Step B: [4-Fluoro-2-(trifluoromethyl)benzyl](triphenyl)phosphonium Bromide

To a stirred solution of 1-(bromomethyl)-4-fluoro-2-(trifluoromethyl)benzene (500 mg, 1.95 mmol) in toluene (5 mL) was added triphenylphosphine (510 mg, 1.95 mmol), and the reaction mixture was warmed to 110° C. and allowed to stir for 16 h. The mixture was allowed to cool to ambient temperature and the precipitate was isolated by filtration, washing with toluene, and dried under reduced pressure to afford the title compound in sufficient purity for use in the next step. MS: m/z=439.0 [M].

Step C: tert-Butyl 1,1-difluoro-2-{(E)-2-[4-fluoro-2-(trifluoromethyl)phenyl]ethenyl}-6-azaspiro[2.5]octane-6-carboxylate To a stirred solution of [4-fluoro-2-trifluoromethyl)benzyl](triphenyl)phosphonium bromide (100 mg, 0.19 mmol) in tetrahydrofuran (2 mL) at 110° C. was added a solution of n-butyllithium in hexanes (2.5 M, 0.15 mL, 0.38 mmol), dropwise. The reaction mixture was allowed to warm to ambient temperature and was stirred for 30 min. To the resulting mixture was added a solution of tert-butyl 1,1-difluoro-2-formyl-6-azaspiro[2.5]octane-6-carboxylate (106 mg, 0.39 mmol) in tetrahydrofuran (0.5 mL), and the reaction mixture was stirred at ambient temperature for 16 h. The resulting mixture was poured into water (10 mL) and extracted with ethyl acetate (3×20 mL). The combined organic layers were washed with a saturated aqueous solution of sodium chloride, dried over anhydrous sodium sulfate, filtered, and the filtrate was concentrated under reduced pressure. The residue was purified by silica gel chromatography, eluting with a gradient of ethyl acetate:petroleum ether ranging from 0:100 to 15:85 to afford the title compound. MS: m/z=421.1 [M-tBu+CH$_3$CN+H].

Step D: tert-Butyl 1,1-difluoro-2-{2-[4-fluoro-2-(trifluoromethyl)phenyl]ethyl}-6-azaspiro[2.5]octane-6-carboxylate To a vessel containing tert-butyl 1,1-difluoro-2-{(E)-2-[4-fluoro-2-(trifluoromethyl)phenyl]ethenyl}-6-azaspiro [2.5]octane-6-carboxylate (40 mg, 0.092 mmol) was added palladium on activated carbon (5% w/w, wet, 4.89 mg, 0.0046 mmol) under an inert atmosphere. Methanol (10 mL) was added and the reaction mixture was placed under an atmosphere of hydrogen (ca. 1 atm) and allowed to stir at ambient temperature for 30 min. The reaction mixture was filtered over a pad of Celite®, washing with methanol, and the filtrate was concentrated under reduced pressure to afford the title compound in sufficient purity for use in the next step. MS: m/z=423.0 [M-tBu+CH$_3$CN+H].

Step E: 1,1-Difluoro-2-{2-[4-fluoro-2-(trifluoromethyl)phenyl]ethyl}-6-azaspiro[2.5]octane Hydrochloride To a solution of tert-butyl 1,1-difluoro-2-{2-[4-fluoro-2-(trifluoromethyl)phenyl]ethyl}-6-azaspiro[2.5]octane-6-carboxylate (40 mg, 0.092 mmol) in ethyl acetate (2 mL) was added a solution of hydrogen chloride in 1,4-dioxane (4 M, 2 mL, 8 mmol) and the reaction mixture was allowed to stir for 1 h at ambient temperature. The reaction mixture was concentrated under reduced pressure to afford the title compound in sufficient purity for use in the next step. MS: m/z=338.1 [M+H].

INTERMEDIATE 18

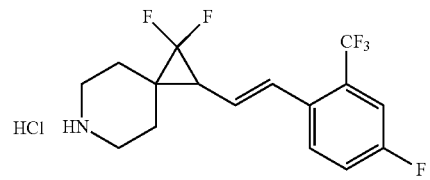

1,1-Difluoro-2-{(E)-2-[4-fluoro-2-(trifluoromethyl) phenyl]ethenyl}-6-azaspiro[2.5]octane Hydrochloride Following analogous procedures to those described in Intermediate 17, but using tert-butyl 1,1-difluoro-2-{(E)-2-[4-fluoro-2-(trifluoromethyl)phenyl]ethenyl}-6-azaspiro [2.5]octane-6-carboxylate in place of tert-butyl 1,1-difluoro-2-{2-[4-fluoro-2-(trifluoromethyl)phenyl]ethyl}-6-azaspiro [2.5]octane-6-carboxylate, the title compound was obtained. MS: m/z=336.0 [M+H].

The intermediates appearing in the following tables were prepared by analogy to the above intermediates, as described or prepared as a result of similar transformations with modifications known to those skilled in the art. The requisite starting materials were described herein, commercially available, known in the literature, or readily synthesized by one skilled in the art. Straightforward protecting group strategies were applied in some routes.

TABLE INT-A

| Intermediate | Structure | MS [M + H] |
|---|---|---|
| A1 | (OMe-substituted pyridine with F and OCH$_2$CF$_3$) | 226.0 |
| A2 | (pyridine with F and OCH$_2$-cyclopropyl) | 168.0 |
| A3 | (pyridine with F and 3,5-dimethylpyrazole) | 192.0 |

Example 1

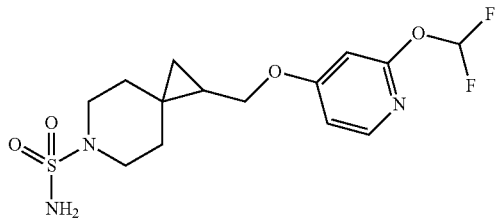 [SMILES: NS(=O)(=O)N1CCC2(CC1)CC2COc1ccnc(OC(F)F)c1]

1-({[2-(Difluoromethoxy)pyridin-4-yl]oxy}methyl)-6-azaspiro[2.5]octane-6-sulfonamide

Step A: tert-Butyl 1-({[2-(difluoromethoxy)pyridin-4-yl]oxy}methyl)-6-azaspiro[2.5]octane-6-carboxylate To a solution of tert-butyl 1-(hydroxymethyl)-6-azaspiro[2.5]octane-6-carboxylate (Intermediate 1) (120 mg, 0.50 mmol) and 2-(difluoromethoxy)-pyridin-4-ol (94 mg, 0.64 mmol) in tetrahydrofuran (10 mL), at ambient temperature, was added triphenylphosphine (396 mg, 1.50 mmol) followed by DIAD (130 mg, 0.64 mmol) and the reaction mixture was stirred for 18 h. Water (25 mL) was added and the resulting mixture was extracted with ethyl acetate (3×25 mL). The combined organic extracts were washed with a saturated aqueous solution of sodium chloride, dried over anhydrous magnesium sulfate, filtered, and the filtrate was concentrated under reduced pressure. The residue was purified by silica gel chromatography, eluting with a gradient of ethyl acetate:hexanes ranging from 0:100 to 50:50, to afford the title compound. $^1$H NMR (300 MHz, CDCl$_3$) δ 7.96 (d, J=5.9 Hz, 1H); 7.44 (t, J=73.1 Hz, 1H); 6.62 (m, 1H); 6.32 (d, J=2.1 Hz, 1H); 4.20 (m, 1H); 3.80 (m, 1H); 3.55-3.35 (m, 4H); 1.51 (m, 1H); 1.45 (s, 9H); 1.39-1.14 (m, 4H); 0.71 (m, 1H); 0.37 (m, 1H).

Step B: 1-({[2-(Difluoromethoxy)pyridin-4-yl]oxy}methyl)-6-azaspiro[2.5]octane To a solution of tert-butyl 1-({[2-(difluoromethoxy)pyridin-4-yl]oxy}methyl)-6-azaspiro[2.5]octane-6-carboxylate (120 mg, 0.31 mmol) in anhydrous DCM (5 mL) at 0° C. was added TFA (0.12 mL, 1.56 mmol) and reaction mixture was allowed to stir at ambient temperature for 18 h. The resulting mixture was poured into a saturated aqueous solution of sodium bicarbonate (10 mL) and extracted with DCM (3×20 mL). The combined organic extracts were dried over anhydrous magnesium sulfate, filtered, and the filtrate was concentrated under reduced pressure to afford the title compound in sufficient purity for use in the next step. MS: m/z=285.1 [M+H].

Step C: 1-({[2-(Difluoromethoxy)pyridin-4-yl]oxy}methyl)-6-azaspiro[2.5]octane-6-sulfonamide To a solution of 1-({[2-(difluoromethoxy)pyridin-4-yl]oxy}methyl)-6-azaspiro[2.5]octane (90 mg, 0.31 mmol) in anhydrous 1,4-dioxane (5 mL) in a sealable vessel at ambient temperature was added sulfamide (170 mg, 1.75 mmol). The vessel was sealed and the mixture was heated at 105° C. for 18 h. The reaction mixture was allowed to cool and was concentrated to dryness under reduced pressure. To the residue was added chloroform, the resulting mixture was filtered, and the filtrate was concentrated under reduced pressure. The residue was purified by preparative reversed-phase HPLC, eluting with a gradient of acetonitrile:water:formic acid ranging from 5:95:0.1 to 95:5:0.1 to give the title compound. MS: m/z=364.1 [M+H]. $^1$H NMR (300 MHz, DMSO-d$_6$) δ 8.02 (d, J=5.9 Hz, 1H); 7.66 (t, J=73.0 Hz, 1H); 6.85 (dd, J=5.9 Hz, 2.2 Hz, 1H); 6.70 (bs, 2H); 6.63 (d, J=2.2 Hz, 1H); 4.26 (m, 1H); 3.97 (m, 1H); 3.10-2.90 (m, 4H); 1.61-1.56 (m, 2H); 1.46-1.39 (m, 2H); 1.14 (m, 1H); 0.63 (m, 1H); 0.39 (m, 1H).

Example 2

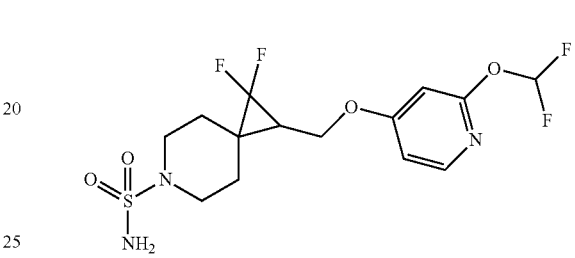

2-({[2-(Difluoromethoxy)pyridin-4-yl]oxy}methyl)-1,1-difluoro-6-azaspiro[2.5]octane-6-sulfonamide, Enantiomer A Following analogous procedures to those described in Example 1, but using tert-butyl 1,1-difluoro-2-(hydroxymethyl)-6-azaspiro[2.5]octane-6-carboxylate, enantiomer A, (Intermediate 8) in place of tert-butyl 1-(hydroxymethyl)-6-azaspiro[2.5]octane-6-carboxylate, the title compound was obtained. MS: m/z=400.1 [M+H]. $^1$H NMR (300 MHz, DMSO-d$_6$) δ 8.04 (d, J=5.8 Hz, 1H); 7.67 (t, J=72.9 Hz, 1H); 6.90 (dd, J=5.8 Hz, 2.2 Hz, 1H); 6.79 (s, 2H); 6.73 (d, J=2.1 Hz, 1H); 4.27 (m, 2H); 3.01 (m, 4H); 2.08 (m, 1H); 1.74 (m, 4H).

Example 3

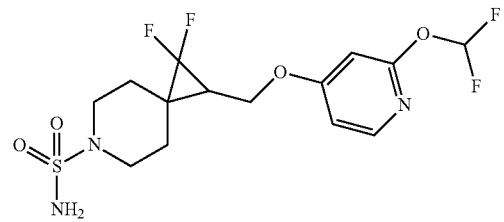 [SMILES: NS(=O)(=O)N1CCC2(CC1)C(COc1ccnc(OC(F)F)c1)C2(F)F]

2-({[2-(Difluoromethoxy)pyridin-4-yl]oxy}methyl)-1,1-difluoro-6-azaspiro[2.5]octane-6-sulfonamide, Enantiomer B Following analogous procedures to those described in Example 1, but using tert-butyl 1,1-difluoro-2-(hydroxymethyl)-6-azaspiro[2.5]octane-6-carboxylate, enantiomer B, (Intermediate 9) in place of tert-butyl 1-(hydroxymethyl)-6-azaspiro[2.5]octane-6-carboxylate, the title compound was obtained. MS: m/z=400.1 [M+H]. $^1$H NMR (300 MHz, DMSO-d$_6$) δ 8.04 (d, J=5.8 Hz, 1H); 7.67 (t, J=72.9 Hz, 1H); 6.90 (dd, J=5.8 Hz, 2.2 Hz, 1H); 6.79 (s, 2H); 6.73 (d, J=2.1 Hz, 1H); 4.27 (m, 2H); 3.01 (m, 4H); 2.08 (m, 1H); 1.74 (m, 4H).

Example 4

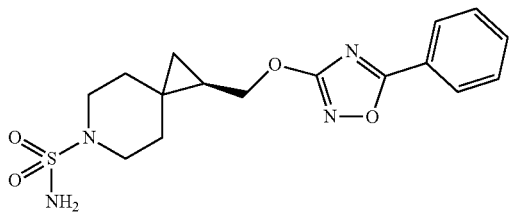 [SMILES: NS(=O)(=O)N1CCC2(CC1)C[C@H]2COc1noc(-c2ccccc2)n1]

(1R)-1-{[(5-Phenyl-1,2,4-oxadiazol-3-yl)oxy]methyl}-6-azaspiro[2.5]octane-6-sulfonamide Step A: tert-Butyl (1R)-1-{[(5-phenyl-1,2,4-oxadiazol-3 yl)oxy]methyl}-6-azaspiro[2.5]octane-6-carboxylate To a suspension of sodium hydride 60% oil dispersion (66 mg, 1.64 mmol) in DMF (5 mL) at 0° C. was added tert-butyl (1R)-1-(hydroxymethyl)-6-azaspiro[2.5]octane-6-carboxylate (Intermediate 2) (200 mg, 0.82 mmol). The resulting mixture was stirred for 1 h at 0° C. and 3-chloro-5-phenyl-1,2,4-oxadiazole (150 mg, 0.82 mmol) was added. The reaction mixture was warmed to ambient temperature and stirred for 20 h. An aqueous solution of 1.0 N hydrochloric acid was added to make the mixture acidic (pH <4), then the mixture was made basic (pH >8) by addition of a saturated aqueous solution of sodium bicarbonate and the resulting mixture was extracted with ethyl acetate (3×25 mL). The combined organic extracts were washed with a saturated aqueous solution of sodium chloride, dried over anhydrous magnesium sulfate, filtered, and the filtrate was concentrated under reduced pressure. The residue was purified by silica gel chromatography, eluting with a gradient of ethyl acetate:hexanes ranging from 0:100 to 40:60 to afford the title compound. MS: m/z=408.2 [M+Na].

Step B: (1R)-1-{[(5-Phenyl-1,2,4-oxadiazol-3-yl)oxy]methyl}-6-azaspiro[2.5]octane-6-sulfonamide Following analogous procedures to those described in Example 1, but using tert-butyl (1R)-1-{[(5-phenyl-1,2,4-oxadiazol-3-yl)oxy]methyl}-6-azaspiro[2.5]octane-6-carboxylate in place of tert-butyl 1-({[2-(difluoromethoxy)pyridin-4-yl]oxy}methyl)-6-azaspiro[2.5]octane-6-carboxylate, the title compound was obtained. MS: m/z=365.1 [M+H]. $^1$H NMR (300 MHz, DMSO-d$_6$) δ 8.04 (m, 2H); 7.69 (m, 1H); 7.60 (m, 2H); 4.44 (m, 1H); 4.28 (m, 1H); 3.11 (m, 2H); 2.90 (m, 2H); 1.70 (m, 1H); 1.59-1.53 (m, 2H); 1.40-1.20 (m, 2H); 0.66 (m, 1H); 0.49 (m, 1H).

Example 5

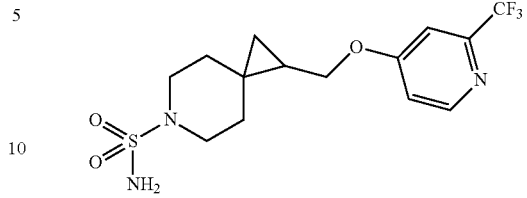

1-({[2-(Trifluoromethyl)pyridin-4-yl]oxy}methyl)-6-azaspiro[2.5]octane-6-sulfonamide Following analogous procedures to those described in Example 4, but using tert-butyl 1-(hydroxymethyl)-6-azaspiro[2.5]octane-6-carboxylate (Intermediate 1) in place of tert-butyl (1R)-1-(hydroxymethyl)-6-azaspiro[2.5]octane-6-carboxylate, and 4-bromo-2-(trifluoromethyl)pyridine in place of 3-chloro-5-phenyl-1,2,4-oxadiazole, the title compound was obtained. MS: m/z=366.1 [M+H]. $^1$H NMR (300 MHz, DMSO-d$_6$) δ 8.52 (d, J=5.7 Hz, 1H); 7.42 (d, J=2.3 Hz, 1H); 7.25 (dd, J=5.7 Hz, 2.3 Hz, 1H); 6.70 (bs, 2H); 4.35 (m, 1H); 4.06 (m, 1H); 3.16-2.92 (m, 4H); 1.64-1.57 (m, 2H); 1.47-1.39 (m, 2H); 1.15 (m, 1H); 0.65 (m, 1H); 0.42 (m, 1H).

Example 6

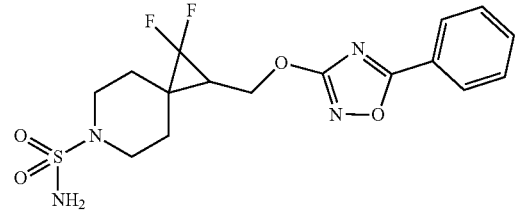 [SMILES: NS(=O)(=O)N1CCC2(CC1)C(COc1noc(-c3ccccc3)n1)C2(F)F]

1,1-Difluoro-2-{[(5-phenyl-1,2,4-oxadiazol-3-yl)oxy]methyl}-6-azaspiro[2.5]octane-6-sulfonamide, Enantiomer A Step A: tert-Butyl 1,1-difluoro-2-{[(5-phenyl-1,2,4-oxadiazol-3-yl)oxy]methyl}-6-azaspiro[2.5]octane-6-carboxylate, enantiomer A To a solution of tert-butyl 1,1-difluoro-2-(hydroxymethyl)-6-azaspiro[2.5]octane-6-carboxylate, enantiomer A, (Intermediate 8) (150 mg, 0.54 mmol) in tetrahydrofuran (10 mL) at ambient temperature was added potassium tert-butoxide (121 mg, 1.08 mmol) and the reaction mixture was stirred at ambient temperature for 5 h. An aqueous solution of 1.0 N hydrochloric acid was added to make the mixture acidic (pH <4), then the mixture was made basic (pH >8) by addition of a saturated aqueous solution of sodium bicarbonate and was extracted with ethyl acetate (3×25 mL). The combined organic extracts were washed with a saturated aqueous solution of sodium chloride, dried over anhydrous magnesium sulfate, filtered, and the filtrate was concentrated under reduced pressure. The residue was purified by silica gel chromatography, eluting with a gradient of ethyl acetate:hexanes ranging from 0:100 to 40:60 to afford the title compound. MS: m/z=447.2 [M+Na].

Step B: 1,1-Difluoro-2-{[(5-phenyl-1,2,4-oxadiazol-3 yl)oxy]methyl}-6-azaspiro[2.5]octane-6-sulfonamide, Enantiomer A Following analogous procedures to those described in Example 1, but using tert-butyl 1,1-difluoro-2-{[(5-phenyl-1,2,4-oxadiazol-3-yl)oxy]methyl}-6-azaspiro[2.5]octane-6-carboxylate, enantiomer A, in place of tert-butyl 1-({[2-(difluoromethoxy)pyridin-4-yl]oxy}methyl)-6-azaspiro[2.5]octane-6-carboxylate, the title compound was obtained. MS: m/z=401.1 [M+H]. $^1$H NMR (300 MHz, DMSO-$d_6$) δ 8.04 (d, J=8.6 Hz, 2H); 7.69 (m, 1H); 7.61 (m, 2H); 6.80 (s, 2H); 4.51 (m, 2H); 3.09 (m, 2H); 2.93-2.88 (m, 2H); 2.25-2.18 (m, 1H); 1.83 (m, 2H); 1.74 (m, 2H).

Example 7

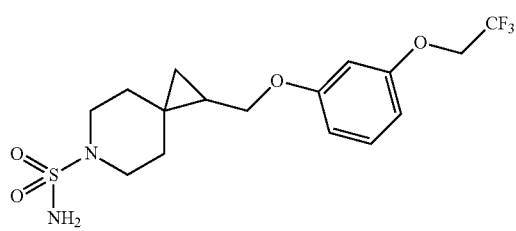 [SMILES: NS(=O)(=O)N1CCC2(CC1)CC2COc1cccc(OCC(F)(F)F)c1]

1-{[3-(2,2,2-Trifuoroethoxy)phenoxy]methyl}-6-azaspiro[2.5]octane-6-sulfonamide

Step A: tert-Butyl 1-{[3-(2,2,2-trifluoroethoxy)phenoxy]methyl}-6-azaspiro[2.5]octane-6-carboxylate To a solution of tert-butyl 1-(hydroxymethyl)-6-azaspiro[2.5]octane-6-carboxylate (Intermediate 1) (100 mg, 0.4 mmol) in toluene (2 mL) in a sealable vessel at ambient temperature were added 1-bromo-3-(2,2,2-trifluoroethoxy)-benzene (88 mg, 0.34 mmol) and cesium carbonate (222 mg, 0.68 mmol). The resulting mixture was stirred and deoxygenated with argon for 10 min then RockPhos Pd G3 catalyst (6 mg, 0.0068 mmol) was added, the vessel was sealed and the reaction mixture was heated at 90° C. for 18 h. The reaction mixture was poured into water (10 mL) and extracted with ethyl acetate (3×10 mL). The combined organic extracts were washed with a saturated aqueous solution of sodium chloride, dried over anhydrous magnesium sulfate, filtered, and the filtrate was concentrated under reduced pressure. The residue was purified by silica gel chromatography, eluting with a gradient of ethyl acetate:hexanes ranging from 0:100 to 50:50 to afford the title compound. MS: m/z=438.2 [M+Na].

Step B: 1-{[3-(2,2,2-Trifluoroethoxy)phenoxy]methyl}-6-azaspiro[2.5]octane-6-sulfonamide Following analogous procedures to those described in Example 1, but using tert-butyl 1-{[3-(2,2,2-trifluoroethoxy)phenoxy]methyl}-6-azaspiro[2.5]octane-6-carboxylate in place of tert-butyl 1-({[2-(difluoromethoxy)pyridin-4-yl]oxy}methyl)-6-azaspiro[2.5]octane-6-carboxylate, the title compound was obtained. MS: m/z=395.1 [M+H]. $^1$H NMR (300 MHz, DMSO-$d_6$) δ 7.18 (m, 1H); 6.70 (bs, 2H); 6.62-6.56 (m, 3H); 4.70 (q, J=8.9 Hz, 2H); 4.12 (m, 1H); 3.82 (m, 1H); 3.12-2.91 (m, 4H); 1.58-1.40 (m, 4H); 1.12 (m, 1H); 0.60 (m, 1H); 0.36 (m, 1H).

Example 8

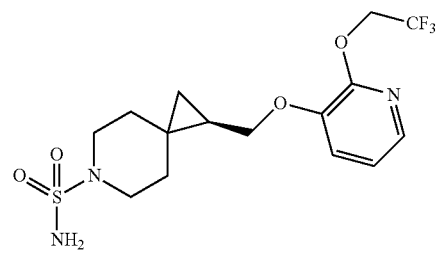 [SMILES: NS(=O)(=O)N1CCC2(CC1)C[C@H]2COc1cccnc1OCC(F)(F)F]

(1R)-1-({[2-(2,2,2-Trifluoroethoxy)pyridin-3-yl]oxy}methyl)-6-azaspiro[2.5]octane-6-sulfonamide Step A: tert-Butyl (1R)-1-[(2-fluoro-3-pyridyl)oxymethyl]-6-azaspiro[2.5]octane-6-carboxylate To a solution of tert-butyl (1R)-1-(hydroxymethyl)-6-azaspiro[2.5]octane-6-carboxylate (Intermediate 2) (300 mg, 1.08 mmol) and 2-fluoro-pyridin-3-ol (124 mg, 1.08 mmol) in tetrahydrofuran (12 mL), at ambient temperature, was added triphenylphosphine (850 mg, 3.24 mmol) followed by DIAD (284 mg, 1.40 mmol) and the reaction mixture was stirred for 18 h. Water (20 mL) was added and the resulting mixture was extracted with ethyl acetate (3×20 mL). The combined organic extracts were washed with a saturated aqueous solution of sodium chloride, dried over anhydrous magnesium sulfate, filtered, and the filtrate was concentrated under reduced pressure. The residue was purified by silica gel chromatography, eluting with a gradient of ethyl acetate:hexanes ranging from 0:100 to 50:50, to afford the title compound. MS: m/z=273.1 [M-Boc+H].

Step B: tert-Butyl (1R)-1-({[2-(2,2,2-trifluoroethoxy)pyridin-3 yl]oxy}methyl)-6-azaspiro[2.5]octane-6-carboxylate To a solution of 2,2,2-trifluoroethanol (0.22 mL, 3.06 mmol) in DMF (10 mL) at 0° C. was added sodium hydride 60% oil dispersion (122 mg, 3.06 mmol). The reaction mixture was stirred at 0° C. for 45 min and tert-butyl (1R)-1-[(2-fluoro-3-pyridyl)oxymethyl]-6-azaspiro[2.5]octane-6-carboxylate (380 mg, 1.02 mmol) was added. The reaction mixture was warmed to ambient temperature and stirred for 18 h. Water (25 mL) was added and the resulting mixture was extracted with ethyl acetate (3×20 mL). The combined organic extracts were washed with a saturated aqueous solution of sodium chloride, dried over magnesium sulfate, filtered, and the filtrate was concentrated under reduced pressure to afford the title compound in sufficient purity for use in the next step. MS: m/z=475.1 [M+Na].

Step C: (1R)-1-({[2-(2,2,2-Trifluoroethoxy)pyridin-3-yl]oxy}methyl)-6-azaspiro[2.5]octane-6-sulfonamide Following analogous procedures to those described in Example 1, but using tert-butyl (1R)-1-({[2-(2,2,2-trifluoroethoxy)pyridin-3-yl]oxy}methyl)-6-azaspiro[2.5]octane-6-carboxylate in place of tert-butyl 1-({[2-(difluoromethoxy)pyridin-4-yl]oxy}methyl)-6-azaspiro[2.5]octane-6-carboxylate, the title compound was obtained. MS: m/z=396.2 [M+H]. $^1$H NMR (300 MHz, CDCl$_3$) δ 7.72 (dd, J=5.0 Hz, 1.2 Hz, 1H); 7.12 (dd, J=7.7 Hz, 1.2 Hz, 1H); 6.90 (dd, J=7.7 Hz, 5.0 Hz, 1H); 4.80 (m, 2H); 4.44 (bs, 2H); 4.25 (m, 1H); 3.76 (m, 1H); 3.35-3.25 (m, 3H); 3.18 (m, 1H); 1.76-1.58 (m, 3H); 1.41 (m, 1H); 1.23 (m, 1H); 0.70 (m, 1H); 0.40 (m, 1H).

Example 9

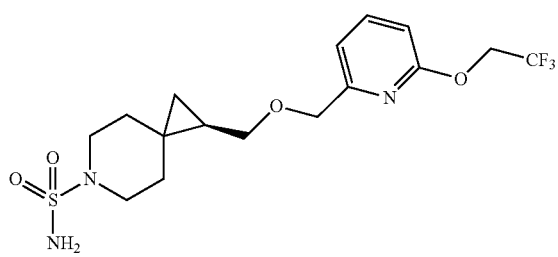 [SMILES: NS(=O)(=O)N1CCC2(CC1)C[C@H]2COCc1cccc(OCC(F)(F)F)n1]

(1R)-1-({[6-(2,2,2-Trifluoroethoxy)pyridin-2-yl]methoxy}methyl)-6-azaspiro[2.5]octane-6-sulfonamide Step A: tert-Butyl (1R)-1-{[(6-bromopyridin-2-yl)methoxy]methyl}-6-azaspiro[2.5]octane-6-carboxylate To a solution of tert-butyl (1R)-1-(hydroxymethyl)-6-azaspiro[2.5]octane-6-carboxylate (Intermediate 2) (300 mg, 1.24 mmol) in tetrahydrofuran (15 mL) at ambient temperature was added potassium tert-butoxide (418 mg, 3.72 mmol). The reaction mixture was stirred at ambient temperature for 1 h, 2-bromo-6-(bromomethyl)pyridine (312 mg, 1.24 mmol) was added, and the reaction mixture was stirred at 50° C. for 2 h. Water (20 mL) was added and the resulting mixture was extracted with ethyl acetate (3×20 mL). The combined organic extracts were washed with a saturated aqueous solution of sodium chloride, dried over anhydrous magnesium sulfate, filtered, and the filtrate was concentrated under reduced pressure. The residue was purified by silica gel chromatography, eluting with a gradient of ethyl acetate:hexanes ranging from 0:100 to 50:50, to afford the title compound. MS: m/z=411.2 [M+H].

Step B: tert-Butyl (1R)-1-({[6-(2,2,2-trifluoroethoxy)pyridin-2 yl]methoxy}methyl)-6-azaspiro[2.5]octane-6-carboxylate To a solution of 2,2,2-trifluoroethanol (0.11 mL, 1.53 mmol) in DMF (5 mL) at 0° C. was added sodium hydride 60% oil dispersion (62 mg, 1.53 mmol). The reaction mixture was stirred at 0° C. for 45 min and tert-butyl (1R)-1-{[(6-bromopyridin-2-yl)methoxy]methyl}-6-azaspiro[2.5]octane-6-carboxylate (210 mg, 0.51 mmol) was added. The reaction mixture was warmed to ambient temperature and stirred for 18 h. Water (10 mL) was added and the resulting mixture was extracted with ethyl acetate (3×10 mL). The combined organic extracts were washed with a saturated aqueous solution of sodium chloride, dried over anhydrous magnesium sulfate, filtered, and the filtrate was concentrated under reduced pressure. The residue was purified by silica gel chromatography, eluting with a gradient of ethyl acetate:hexanes ranging from 0:100 to 50:50, to afford the title compound. MS: m/z=431.2 [M+H].

Step C: (1R)-1-({[6-(2,2,2-Trifluoroethoxy)pyridin-2-yl]methoxy}methyl)-6-azaspiro[2.5]octane-6-sulfonamide Following analogous procedures to those described in Example 1, but using tert-butyl (1R)-1-({[6-(2,2,2-trifluoroethoxy)pyridin-2-yl]methoxy}methyl)-6-azaspiro[2.5]octane-6-carboxylate in place of tert-butyl 1-({[2-(difluoromethoxy)pyridin-4-yl]oxy}methyl)-6-azaspiro[2.5]octane-6-carboxylate, the title compound was obtained. MS: m/z=410.1 [M+H]. $^1$H NMR (300 MHz, DMSO-d$_6$) δ 7.86 (t, J=8.0 Hz, 1H); 7.21 (d, J=7.3 Hz, 1H); 6.93 (d, J=8.2 Hz, 1H); 6.77 (bs, 2H); 5.02 (q, J=9.1 Hz, 2H); 4.54 (m, 2H); 3.69 (dd, J=10.6 Hz, 6.1 Hz, 1H); 3.48 (dd, J=10.5 Hz, 8.6 Hz, 1H); 3.21 (m, 1H); 3.12 (m, 1H); 2.95 (m, 2H); 1.67 (m, 1H); 1.53 (m, 2H); 1.38 (m, 1H); 1.07 (m, 1H); 0.59 (m, 1H); 0.32 (m, 1H).

Example 10

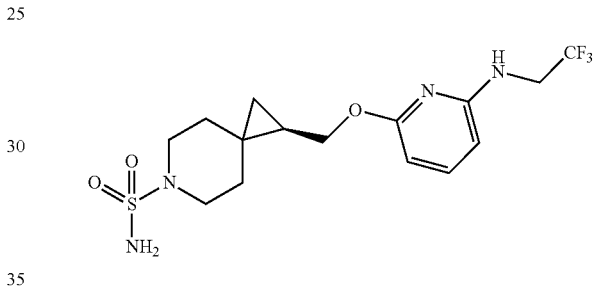

(1R)-1-[({6-[(2,2,2-Trifluoroethyl)amino]pyridin-2-yl}oxy)methyl]-6-azaspiro[2.5]octane-6-sulfonamide Step A: tert-Butyl (1R)-1-{[(6-chloropyridin-2-yl)oxy]methyl}-6-azaspiro[2.5]octane-6-carboxylate To a suspension of sodium hydride 60% oil dispersion (145 mg, 3.72 mmol) in DMF (10 mL) at 0° C. was added tert-butyl (1R)-1-(hydroxymethyl)-6-azaspiro[2.5]octane-6-carboxylate (Intermediate 2) (300 mg, 1.24 mmol). The resulting mixture was stirred for 1 h at 0° C. and 2,6-dichloropyridine (184 mg, 1.24 mmol) was added. The reaction mixture was warmed to ambient temperature and stirred for 20 h. An aqueous solution of 1.0 N hydrochloric acid was added to make the mixture acidic (pH <4), then the mixture was made basic (pH >8) by addition of a saturated aqueous solution of sodium bicarbonate and was extracted with ethyl acetate (3×25 mL). The combined organic extracts were washed with a saturated aqueous solution of sodium chloride, dried over anhydrous magnesium sulfate, filtered, and the filtrate was concentrated under reduced pressure. The residue was purified by silica gel chromatography, eluting with a gradient of ethyl acetate:hexanes ranging from 0:100 to 50:50 to afford the title compound. MS: m/z=353.2 [M+H].

Step B: tert-Butyl (1R)-1-[({6-[(2,2,2-trifluoroethyl)amino]pyridin-2-yl}oxy)methyl]-6-azaspiro[2.5]octane-6-carboxylate To a solution of 2,2,2-trifluoroethylamine (0.026 mL, 0.37 mmol) in 1,4-dioxane (2 mL) in a sealable vessel at ambient temperature were added tert-butyl (1R)-1-{[(6-chloropyridin-2-yl)oxy]methyl}-6-azaspiro[2.5]octane-6-carboxylate (130 mg, 0.37 mmol) and cesium carbonate (300 mg, 0.93 mmol). The resulting mixture was stirred and deoxygenated with argon for 10 min then palladium(II) acetate (2.2 mg, 0.01 mmol) and BINAP (12 mg, 0.02 mmol) were added, the vessel was sealed and the reaction mixture was heated at 100° C. for 16 h. The reaction mixture was poured into water (10 mL) and extracted with ethyl acetate (3×10 mL). The combined organic extracts were washed with a saturated aqueous solution of sodium chloride, dried over anhydrous magnesium sulfate, filtered, and the filtrate was concentrated under reduced pressure. The residue was purified by silica gel chromatography, eluting with a gradient of ethyl acetate:hexanes ranging from 0:100 to 50:50 to afford the title compound. MS: m/z=416.2 [M+H].

Step C: (1R)-1-[({6-[(2,2,2-Trifluoroethyl)amino]pyridin-2-yl}oxy)methyl]-6-azaspiro[2.5]octane-6-sulfonamide Following analogous procedures to those described in Example 1, but using tert-butyl (1R)-1-[({6-[(2,2,2-trifluoroethyl)amino]pyridin-2-yl}oxy)methyl]-6-azaspiro[2.5]octane-6-carboxylate in place of tert-butyl 1-({[2-(difluoromethoxy)pyridin-4-yl]oxy}methyl)-6-azaspiro[2.5]octane-6-carboxylate, the title compound was obtained. MS: m/z=395.1 [M+H]. $^1$H NMR (300 MHz, DMSO-d$_6$) δ 7.33 (t, J=7.7 Hz, 1H); 7.05 (t, J=6.5 Hz, 1H); 6.70 (bs, 2H); 6.11 (d, J=7.7 Hz, 1H); 5.98 (d, J=7.7 Hz, 1H); 4.39 (dd, J=11.6 Hz, 6.5 Hz, 1H); 4.14-3.92 (m, 3H); 3.12 (m, 1H); 3.01 (m, 1H); 2.90 (m, 2H); 1.68-1.38 (m, 3H); 1.35 (m, 1H); 1.13 (m, 1H); 0.55 (dd, J=8.5 Hz, 4.3 Hz, 1H); 0.34 (t, J=4.8 Hz, 1H).

Example 11

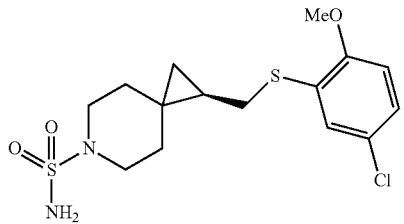 [SMILES: COc1ccc(Cl)cc1SC[C@@H]1CC12CCN(S(N)(=O)=O)CC2]

(1R)-1-{[(5-Chloro-2-methoxyphenyl)sulfanyl]methyl}-6-azaspiro[2.5]octane-6-sulfonamide Step A: tert-Butyl (1R)-1-{[(5-chloro-2-methoxyphenyl)sulfanyl]methyl}-6-azaspiro[2.5]octane-6-carboxylate To a solution of tert-butyl (1R)-1-(hydroxymethyl)-6-azaspiro[2.5]octane-6-carboxylate (Intermediate 2) (200 mg, 0.83 mmol) in pyridine (5 mL) at ambient temperature were added 1,1'-disulfanediylbis(5-chloro-2-methoxybenzene) (Intermediate 11) (850 mg, 2.50 mmol) and tributylphosphine (0.622 mL, 2.50 mmol). The reaction mixture was stirred at ambient temperature for 48 h then diluted with ethyl acetate (20 mL) and an aqueous solution of 1.0 N sodium hydroxide (10 mL) was added. The resulting mixture was washed with an aqueous solution of 1.0 N hydrochloric acid (10 mL), followed by a saturated aqueous solution of sodium bicarbonate (10 mL). The organic layer was dried over anhydrous magnesium sulfate, filtered, and the filtrate was concentrated under reduced pressure. The residue was purified by silica gel chromatography, eluting with a gradient of ethyl acetate:hexanes ranging from 0:100 to 20:80 to afford the title compound. MS: m/z=420.1 [M+Na].

Step B: (1R)-1-{[(5-Chloro-2-methoxyphenyl)sulfanyl]methyl}-6-azaspiro[2.5]octane-6-sulfonamide Following analogous procedures to those described in Example 1, but using tert-butyl (1R)-1-{[(5-chloro-2-methoxyphenyl)sulfanyl]methyl}-6-azaspiro[2.5]octane-6-carboxylate in place of tert-butyl 1-({[2-(difluoromethoxy)pyridin-4-yl]oxy}methyl)-6-azaspiro[2.5]octane-6-carboxylate, the title compound was obtained. MS: m/z=377.1 [M+H]. $^1$H NMR (300 MHz, DMSO-d$_6$) δ 7.18 (m, 3H); 6.95 (d, J=8.5 Hz, 1H); 6.70 (bs, 2H); 3.79 (m, 3H); 3.20 (m, 1H); 3.08 (m, 1H); 2.97 (d, J=7.4 Hz, 2H); 2.84 (m, 2H); 1.68 (m, 1H); 1.51 (m, 2H); 1.25 (m, 1H); 0.86 (m, 1H); 0.58 (dd, J=8.4 Hz, 4.3 Hz, 1H); 0.27 (t, J=4.7 Hz, 1H).

Example 12

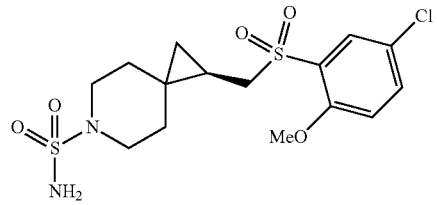 [SMILES: COc1ccc(Cl)cc1S(=O)(=O)C[C@@H]1CC12CCN(S(N)(=O)=O)CC2]

(1R)-1-{[(5-Chloro-2-methoxyphenyl)sulfonyl]methyl}-6-azaspiro[2.5]octane-6-sulfonamide To a solution of (1R)-1-{[(5-chloro-2-methoxyphenyl)sulfanyl]methyl}-6-azaspiro[2.5]octane-6-sulfonamide (Example 11) (78 mg, 0.21 mmol) in dichloromethane (3 mL) at 0° C. was added 3-chloroperbenzoic acid (ca. 70%, 128 mg, 0.52 mmol) and the reaction mixture was allowed to warm to ambient temperature and was stirred for 18 h. A saturated aqueous solution of potassium carbonate (10 mL) was added and the resulting mixture was extracted with dichloromethane (3×10 mL). The combined organic extracts were dried over anhydrous magnesium sulfate, filtered, and the filtrate was concentrated under reduced pressure. The residue was purified by silica gel chromatography, eluting with a gradient of ethyl acetate:hexanes ranging from 0:100 to 100:0 to afford the title compound. MS: m/z=409.2 [M+H]. $^1$H NMR (300 MHz, DMSO-d$_6$) δ 7.78 (dd, J=8.9 Hz, 2.8 Hz, 1H); 7.70 (d, J=2.8 Hz, 1H); 7.33 (d, J=8.9 Hz, 1H); 6.68 (bs, 2H); 3.92 (s, 3H); 3.59 (dd, J=14.5 Hz, 6.5 Hz, 1H); 3.35 (dd, J=14.5 Hz, 7.8 Hz, 1H); 3.20-3.03 (m, 2H); 2.70 (m, 2H); 1.45 (m, 2H); 1.32 (m, 1H); 1.11 (m, 1H); 0.80 (m, 1H); 0.49 (dd, J=8.4 Hz, 4.5 Hz, 1H); 0.13 (t, J=4.7 Hz, 1H).

Example 13

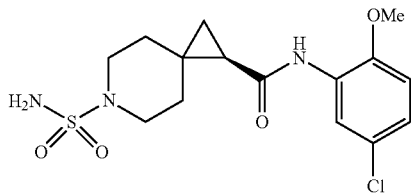 [SMILES: COc1ccc(Cl)cc1NC(=O)[C@@H]1CC12CCN(S(N)(=O)=O)CC2]

(1R)—N-(5-Chloro-2-methoxyphenyl)-6-sulfamoyl-6-azaspiro[2.5]octane-1-carboxamide To a solution of (1R)-6-sulfamoyl-6-azaspiro[2.5]octane-1-carboxylic acid (Intermediate 13) (93 mg, 0.40 mmol) in dichloromethane (3 mL) and dimethylsulfoxide (0.3 mL) were added HATU (181 mg, 0.48 mmol), 5-chloro-2-methoxyaniline (81 mg, 0.52 mmol), and N-methylmorpholine (0.13 mL, 1.18 mmol). The reaction mixture was allowed to stir for 18 h. A saturated aqueous solution of ammonium chloride (30 mL) was added and the resulting mixture extracted with ethyl acetate (70 mL). The organic phase was washed with a saturated aqueous solution of sodium bicarbonate (30 mL) and a saturated aqueous solution of sodium chloride (30 mL), dried (sodium sulfate), filtered, and the filtrate was concentrated under reduced pressure. The residue was purified by silica gel chromatography, eluting with a gradient of dichloromethane:methanol ranging from 100:0 to 95:5 to afford the title compound. MS: m/z=374.1 [M+H]. $^1$H NMR (500 MHz, DMSO-$d_6$) δ 9.53 (s, 1H); 8.08 (s, 1H); 7.10-7.04 (m, 2H); 6.72 (s, 2H); 3.85 (s, 3H); 3.09-2.99 (m, 3H); 2.86-2.80 (m, 1H); 2.14-2.10 (m, 1H); 1.78-1.75 (m, 2H); 1.58-1.44 (m, 2H); 1.03-1.00 (m, 1H); 0.91-0.86 (m, 1H).

Example 14

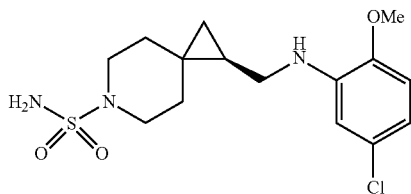 [SMILES: COc1ccc(Cl)cc1NC[C@@H]1CC12CCN(S(N)(=O)=O)CC2]

(1R)-1-{[(5-Chloro-2-methoxyphenyl)amino]methyl}-6-azaspiro[2.5]octane-6-sulfonamide To a solution of (1R)—N-(5-chloro-2-methoxyphenyl)-6-sulfamoyl-6-azaspiro[2.5]octane-1-carboxamide (Example 13) (102 mg, 0.27 mmol) in tetrahydrofuran (3 mL) was added borane tetrahydrofuran complex in tetrahydrofuran (1.0 M, 1.36 mL, 1.36 mmol) and the reaction mixture was allowed to stir at 60° C. for 90 min. The reaction mixture was allowed to cool to ambient temperature and an aqueous solution of hydrochloric acid (1 M) was added dropwise until gas evolution ceased. A saturated aqueous solution of sodium bicarbonate (30 mL) was added and the resulting mixture extracted with ethyl acetate (2×40 mL). The combined organic phases were washed with a saturated aqueous solution of sodium chloride (30 mL), dried (sodium sulfate), filtered, and the filtrate was concentrated under reduced pressure. The residue was partially purified by silica gel chromatography, eluting with a gradient of ethyl acetate:hexanes ranging from 0:100 to 100:0. Further purification was achieved by preparative reversed-phase HPLC, eluting with a gradient of acetonitrile:water:trifluoroacetic acid ranging from 10:90:0.1 to 85:15:0.1 to afford the title compound. MS: m/z=360.1 [M+H]. $^1$H NMR (500 MHz, DMSO-$d_6$) δ 6.77 (d, J=8.3 Hz, 1H); 6.70 (br s, 2H), 6.58-6.49 (m, 2H), 4.90 (t, J=5.4 Hz, 1H); 3.78 (s, 3H), 3.19-3.08 (m, 3H), 3.06-2.97 (m, 1H), 2.92-2.84 (m, 2H), 1.73-1.65 (m, 1H), 1.61-1.47 (m, 2H), 1.29-1.22 (m, 1H), 1.05-0.98 (m, 1H); 0.53 (dd, J=8.5, 4.2 Hz, 1H); 0.27 (t, J=4.7 Hz, 1H).

Example 15

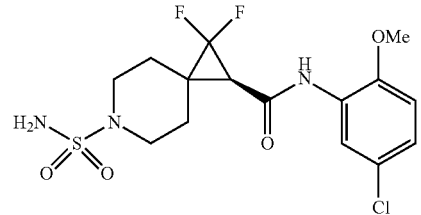 [SMILES: COc1ccc(Cl)cc1NC(=O)[C@@H]1C(F)(F)C12CCN(S(N)(=O)=O)CC2]

(1R)—N-(5-Chloro-2-methoxyphenyl)-2,2-difluoro-6-sulfamoyl-6-azaspiro[2.5]octane-1-carboxamide To a solution of (1R)-2,2-difluoro-6-sulfamoyl-6-azaspiro[2.5]octane-1-carboxylic acid (Intermediate 14) (25 mg, 0.093 mmol) in dichloromethane (2 mL) and dimethylsulfoxide (2 mL) were added HOAt (14.3 mg, 0.093 mmol), 5-chloro-2-methoxyaniline (14.6 mg, 0.093 mmol), and EDC (18 mg, 0.093 mmol). The reaction mixture was allowed to stir for 1 h at ambient temperature. The resulting mixture was concentrated under reduced pressure to remove dichloromethane and the residual mixture was purified by preparative reversed-phase HPLC, eluting with a gradient of acetonitrile:water:trifluoroacetic acid ranging from 37:63:0.1 to 57:43:0.1 to afford the title compound. MS: m/z=410.1 [M+H]. $^1$H NMR (400 MHz, CD$_3$OD): δ 8.11-8.04 (m, 1H); 7.12-7.05 (m, 1H); 6.99 (d, J=8.8 Hz, 1H); 3.90 (s, 3H); 3.23-3.21 (m, 2H); 3.15 (br s, 2H); 2.66 (d, J=13.7 Hz, 1H); 2.30-2.13 (m, 2H); 1.91-1.82 (m, 2H).

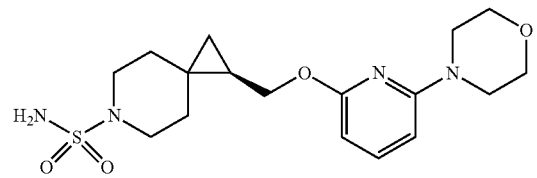 [SMILES: NS(=O)(=O)N1CCC2(CC1)C[C@H]2COc1cccc(N2CCOCC2)n1]

(1R)-1-({[6-(Morpholin-4-yl)pyridin-2-yl]oxy}methyl)-6-azaspiro[2.5]octane-6-sulfonamide Step A: (1R)-1-({[6-(Morpholin-4-yl)pyridin-2-yl]oxy}methyl)-6-azaspiro[2.5]octane To a solution of tert-butyl (1R)-1-(hydroxymethyl)-6-azaspiro[2.5]octane-6-carboxylate (Intermediate 2) (15 mg, 0.062 mmol) in 1,4-dioxane (0.41 mL) at ambient temperature were added 4-(6-bromopyridin-2-yl)morpholine (30 mg, 0.12 mmol), RockPhos Pd G3 (5.2 mg, 0.0062 mmol), and cesium carbonate (60.8 mg, 0.186 mmol). The reaction mixture was heated at 100° C. for 18 h and then filtered. To the filtrate was added an aqueous solution of hydrochloric acid (4 M, 0.31 mL, 1.2 mmol) and the resulting mixture was stirred at ambient temperature for 3 h and then concentrated to dryness. The residue was purified by preparative reversed-phase HPLC, eluting with a gradient of acetonitrile:water: trifluoroacetic acid ranging from 95:5:0.1 to 5:95:0.1 to afford the title compound. MS: m/z=304.2 [M+H].

Step B: (1R)-1-({[6-(Morpholin-4-yl)pyridin-2-yl]oxy}methyl)-6-azaspiro[2.5]octane-6-sulfonamide To (1R)-1-({[6-(morpholin-4-yl)pyridin-2-yl]oxy}methyl)-6-azaspiro[2.5]octane (9 mg, 0.030 mmol) was added a solution of sulfamide (13 mg, 0.14 mmol) and triethylamine (0.029 mL, 0.21 mmol) in N,N-dimethylformamide (0.14 mL) and the reaction mixture was heated at 100° C. and allowed to stir for 6 h. The reaction mixture was filtered and the filtrate was purified by preparative reversed-phase HPLC, eluting with a gradient of acetonitrile:water: trifluoroacetic acid ranging from 95:5:0.1 to 5:95:0.1 to afford the title compound. MS: m/z=383.4 [M+H]. $^1$H NMR (500 MHz, DMSO-$d_6$) δ 7.45 (1, J=10 Hz, 1H); 6.72 (s, 2H); 6.28 (d, J=10 Hz, 1H); 6.09 (d, J=10 Hz, 1H); 4.42-4.38 (m, 1H); 4.01-3.97 (m, 1H); 3.69-3.67 (m, 2H); 3.58 (br s, 3H); 3.37 (br s, 3H); 3.20-3.05 (m, 1H); 3.02-2.99 (m, 1H); 2.99-2.92 (m, 2H); 1.65-1.61 (m, 1H); 1.56-1.53 (m, 1H); 1.48-1.42 (m, 1H); 1.40-1.35 (m, 1H); 1.17-1.09 (m, 1H); 0.60-0.55 (m, 1H); 0.37 (br s, 1H).

Example 17

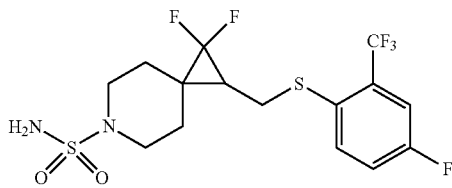 [SMILES: NS(=O)(=O)N1CCC2(CC1)C(CSc1ccc(F)cc1C(F)(F)F)C2(F)F]

1,1-Difluoro-2-({[4-fluoro-2-(trifluoromethyl)phenyl]sulfanyl}methyl)-6-azaspiro[2.5]octane-6-sulfonamide To a stirred mixture of 1,1-difluoro-2-({[4-fluoro-2-(trifluoromethyl)phenyl]sulfanyl}methyl)-6-azaspiro[2.5]octane hydrochloride (Intermediate 16) (155 mg, 0.40 mmol) and triethylamine (0.17 mL, 1.19 mmol) in 1,4-dioxane (8 mL) was added sulfamide (190 mg, 1.98 mmol) and the reaction mixture was warmed to 95° C. and allowed to stir for 16 h. The resulting mixture was cooled to ambient temperature and poured into water (10 mL) and extracted with ethyl acetate (3×20 mL). The combined organic layers were washed with a saturated aqueous solution of sodium chloride, dried over anhydrous sodium sulfate, filtered, and the filtrate was concentrated under reduced pressure. The residual mixture was purified by preparative reversed-phase HPLC, eluting with a gradient of acetonitrile:water:trifluoroacetic acid ranging from 49:51:0.1 to 69:31:0.1 to afford the title compound. MS: m/z=434.9 [M+H]. $^1$H NMR (400 MHz, CD$_3$OD): δ 7.78 (dd, J=8.8, 5.2 Hz, 1H); 7.51 (dd, J=9.0, 2.9 Hz, 1H); 7.39 (dt, J=8.2, 2.4 Hz, 1H); 3.43-3.32 (m, 2H); 3.14-3.09 (m, 2H); 2.94-2.82 (m, 2H); 1.84-1.54 (m, 5H).

Example 18

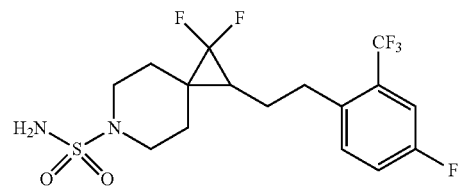 [SMILES: NS(=O)(=O)N1CCC2(CC1)C(CCc1ccc(F)cc1C(F)(F)F)C2(F)F]

1,1-Difluoro-2-{2-[4-fluoro-2-(trifluoromethyl)phenyl]ethyl}-6-azaspiro[2.5]octane-6-sulfonamide To a stirred mixture of 1,1-difluoro-2-{2-[4-fluoro-2-(trifluoromethyl)phenyl]ethyl}-6-azaspiro[2.5]octane hydrochloride (Intermediate 17) (34 mg, 0.091 mmol) and triethylamine (0.04 mL, 0.28 mmol) in 1,4-dioxane (2 mL) was added sulfamide (44 mg, 0.46 mmol) and the reaction mixture was warmed to 100° C. and allowed to stir for 13 h. The resulting mixture was cooled to ambient temperature and poured into water (10 mL) and extracted with ethyl acetate (3×20 mL). The combined organic layers were washed with a saturated aqueous solution of sodium chloride, dried over anhydrous sodium sulfate, filtered, and the filtrate was concentrated under reduced pressure. The residual mixture was purified by preparative reversed-phase HPLC, eluting with a gradient of acetonitrile:water:ammonium hydroxide ranging from 48:52:0.04 to 78:22:0.04 to afford the title compound. MS: m/z=417.1 [M+H]. $^1$H NMR (400 MHz, CDCl$_3$): δ 7.38-7.26 (m, 2H); 7.23-7.16 (m, 1H); 4.42 (s, 2H); 3.55-3.45 (m, 2H); 2.99-2.76 (m, 4H); 1.92-1.73 (m, 3H); 1.71-1.59 (m, 3H); 1.34-1.23 (m, 1H).

Example 19

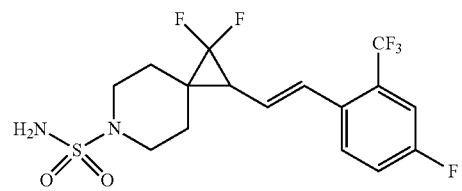 [SMILES: NS(=O)(=O)N1CCC2(CC1)C(/C=C/c1ccc(F)cc1C(F)(F)F)C2(F)F]

1,1-Difluoro-2-{(E)-2-[4-fluoro-2-(trifluoromethyl)phenyl]ethenyl}-6-azaspiro[2.5]octane-6-sulfonamide Following analogous procedures to those described in Example 18, but using 1,1-difluoro-2-{(E)-2-[4-fluoro-2-(trifluoromethyl)phenyl]ethenyl}-6-azaspiro[2.5]octane hydrochloride (Intermediate 18) in place of 1,1-difluoro-2-{2-[4-fluoro-2-(trifluoromethyl)phenyl]ethyl}-6-azaspiro [2.5]octane hydrochloride, the title compound was obtained. MS: m/z=415.1 [M+H]. $^1$H NMR (400 MHz, CDCl$_3$): δ 7.41 (dd, J=9.2, 2.8 Hz, 1H); 7.34-7.31 (m, 1H); 7.29-7.26 (m, 1H); 6.84 (d, J=11.6 Hz, 1H); 5.59 (t, J=10.4 Hz, 1H);

4.38 (br s, 2H); 3.45-3.36 (m, 1H); 3.35-3.28 (m, 1H); 3.10-2.99 (m, 2H); 1.99-1.93 (m, 1H); 1.89-1.86 (m, 2H); 1.86-1.70 (m, 2H).

The examples appearing in the following tables EX-A and EX-B were prepared by analogy to the above examples, as described or prepared as a result of similar transformations with modifications known to those skilled in the art. The requisite starting materials were described herein, commercially available, known in the literature, or readily synthesized by one skilled in the art. Straightforward protecting group strategies were applied in some routes.

TABLE EX-A

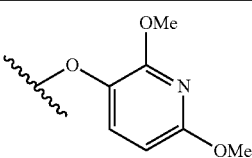

| Example | X | Y | R | Stereochemistry | MS [M + H] |
|---|---|---|---|---|---|
| A1 | H | H | 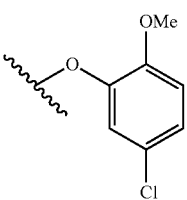 [SMILES: *Oc1cc(Cl)ccc1OC] | R | 358.2 |
| A2 | F | H | 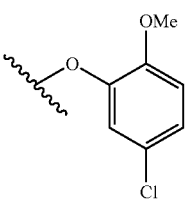 [SMILES: *Oc1cc(Cl)ccc1OC] | Enantiomer A | 397.1 |
| A3 | F | H | 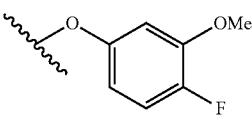 [SMILES: *Oc1ccc(F)c(OC)c1] | Enantiomer B | 397.2 |
| A4 | H | H | 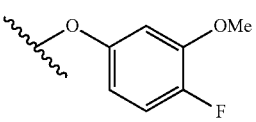 [SMILES: *Oc1ccc(F)c(OC)c1] | R | 345.1 |
| A5 | H | H | 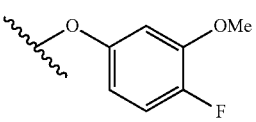 [SMILES: *Oc1ccc(F)c(OC)c1] | S | 345.1 |
| A6 | H | H | 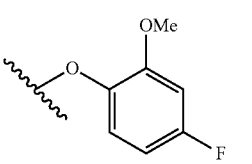 [SMILES: *Oc1ccc(F)cc1OC] | R | 345.1 |
| A7 | H | H | 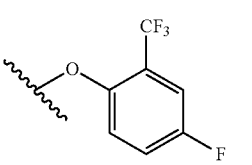 [SMILES: *Oc1ccc(F)cc1C(F)(F)F] | Enantiomer A | 383.1 |

TABLE EX-A-continued
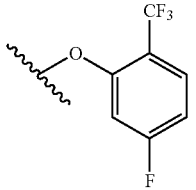 [SMILES: *Oc1cc(F)ccc1C(F)(F)F]
| Example | X | Y | R | Stereochemistry | MS [M + H] |
|---|---|---|---|---|---|
| A8 | F | H | 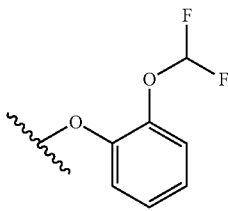 [SMILES: *Oc1ccccc1OC(F)F] | Enantiomer A | 419.1 |
| A9 | H | H | 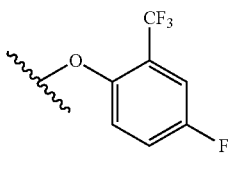 [SMILES: *Oc1ccc(F)cc1C(F)(F)F] | Enantiomer A | 363.1 |
| A10 | F | H | 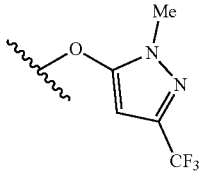 | Enantiomer B | 419.1 |
| A11 | F | H | 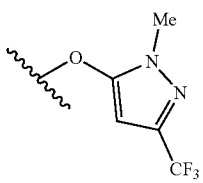 [SMILES: *Oc1cc(C(F)(F)F)nn1C] | Enantiomer A | 405.1 |
| A12 | F | H | 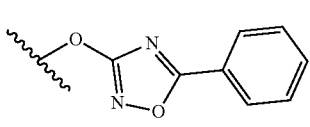 [SMILES: *Oc1noc(-c2ccccc2)n1] | Enantiomer B | 405.1 |
| A13 | H | H | 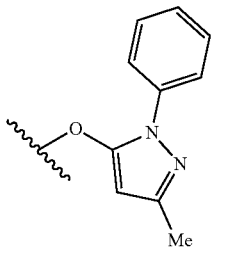 [SMILES: *Oc1cc(C)nn1-c1ccccc1] | S | 365.1 |
| A14 | H | H |  | Racemic | 377.1 |

TABLE EX-A-continued

| Example | X | Y | R | Stereochemistry | MS [M + H] |
|---|---|---|---|---|---|
| A15 | H | H | 2-CF3, 5-F phenyl ether | Enantiomer A | 383.1 |
| A16 | H | H | 4-OMe, 6-(OCH2CF3) pyridin-2-yl ether | S | 426.1 |
| A17 | H | H | 6-(OCH2-cyclopropyl) pyridin-2-yl ether | R | 368.1 |
| A18 | H | H | 6-(OCH2-cyclopropyl) pyridin-2-yl ether | S | 368.1 |
| A19 | H | H | 6-(3,5-dimethylpyrazol-1-yl) pyridin-2-yl ether | R | 392.1 |
| A20 | H | H | 6-(3,5-dimethylpyrazol-1-yl) pyridin-2-yl ether | S | 392.1 |
| A21 | F | H | 5-phenyl-1,2,4-oxadiazol-3-yl ether | Enantiomer B | 401.1 |
| A22 | H | F | 5-phenyl-1,2,4-oxadiazol-3-yl ether | Racemic | 401.1 |
| A23 | H | H | 3-(OCHF2) phenyl ether | Racemic | 363.1 |

TABLE EX-A-continued

| Example | X | Y | R | Stereochemistry | MS [M + H] |
|---|---|---|---|---|---|
| A24 | H | H | -O-C6H4-OCF3 (meta) | R | 381.1 |
| A25 | H | H | -O-C6H4-OCF3 (meta) | S | 381.1 |
| A26 | H | H | -O-C6H3(F)(OMe) | Racemic | 345.1 |
| A27 | H | H | -O-pyridyl-OMe | Racemic | 328.1 |
| A28 | F | H | -O-C6H4-OCHF2 (meta) | Enantiomer A | 399.1 |
| A29 | F | H | -O-C6H4-OCHF2 (meta) | Enantiomer B | 399.1 |
| A30 | F | H | -O-C6H4-OCH2CF3 (meta) | Enantiomer A | 431.1 |
| A31 | F | H | -O-C6H3(F)(OMe) | Enantiomer A | 381.1 |
| A32 | H | H | -O-pyridyl-OCH2CF3 | Racemic | 396.1 |
| A33 | F | H | -O-pyridyl-OCH2CF3 | Enantiomer A | 432.1 |
| A34 | F | H | -O-pyridyl-OCH2CF3 | Enantiomer B | 432.1 |

TABLE EX-A-continued

| Example | X | Y | R | Stereochemistry | MS [M + H] |
|---|---|---|---|---|---|
| A35 | F | H | -O-(3-position of pyridine with 2-OCH$_2$CF$_3$) | Enantiomer A | 432.1 |
| A36 | F | H | -O-(3-position of pyridine with 2-OCH$_2$CF$_3$) | Enantiomer B | 432.1 |
| A37 | H | H | -O-(pyridine-2,6-diyl)-O-CH$_2$CF$_3$ | R | 396.2 |
| A38 | H | H | -O-(pyridine-2,6-diyl)-O-CH$_2$CF$_3$ | S | 396.2 |
| A39 | H | F | -O-(pyridine-2,6-diyl)-O-CH$_2$CF$_3$ | Racemic | 432.2 |
| A40 | F | H | -O-(pyridine-2,6-diyl)-O-CH$_2$CF$_3$ | Enantiomer A | 432.2 |
| A41 | F | H | -O-(pyridine-2,6-diyl)-O-CH$_2$CF$_3$ | Enantiomer B | 432.2 |
| A42 | H | H | -O-(2-OMe-4-Cl-phenyl) | Racemic | 361.1 |
| A43 | H | H | -S-(4-CF$_3$-phenyl) | Racemic | 381.1 |
| A44 | F | H | -S-(4-CF$_3$-phenyl) | Enantiomer A | 417.1 |

TABLE EX-A-continued

| Example | X | Y | R | Stereochemistry | MS [M + H] |
|---|---|---|---|---|---|
| A45 | H | H | *pyridine with O-linker and SO2Me at 6-position* | R | 376.3 |
| A46 | H | H | *pyridine with O-linker and 4-methylpiperazin-1-yl* | R | 396.5 |
| A47 | H | H | *pyridine with O-linker and CN* | R | 323.3 |
| A48 | H | H | *pyridine with O-linker and Me* | R | 312.1 |
| A49 | H | H | *pyridine with O-linker and cyclopropyl* | R | 338.4 |
| A50 | H | H | *pyridine with O-linker and 3-methylpyrazol-1-yl* | R | 378.4 |
| A51 | H | H | *pyridine with O-linker and OMe* | R | 328.3 |
| A52 | H | H | *pyridine with O-linker and C(Me)2OH* | R | 356.4 |
| A53 | H | H | *pyridine with O-linker and CH(Me)2 / 1-methylethyl* | R | 340.4 |

TABLE EX-A-continued

| Example | X | Y | R | Stereochemistry | MS [M + H] |
|---|---|---|---|---|---|
| A54 | H | H | 6-OEt pyridin-2-yl-oxy | R | 342.4 |
| A55 | H | H | 6-(2-methylpropan-2-yl)pyridin-2-yl-oxy | R | 354.4 |
| A56 | H | H | 6-(1,1-difluoroethyl)pyridin-2-yl-oxy | R | 362.4 |
| A57 | H | H | 6-phenylpyridin-2-yl-oxy | R | 374.4 |
| A58 | H | H | 6-(pyridin-4-yl)pyridin-2-yl-oxy | R | 375.4 |
| A59 | F | H | (2-methoxy-5-chlorophenyl)amino | R | 396.2 |
| A60 | F | H | (2,5-dimethylphenyl)amino | R | 360.3 |
| A61 | F | H | (1-phenyl-1H-tetrazol-5-yl)thio | Enantiomer A | 417.1 |

TABLE EX-A-continued

[Structure: piperidine with sulfamoyl group H2N-S(=O)2-N, fused to cyclopropane with X,X substituents and Y,Y, with R group via CH2]

| Example | X | Y | R | Stereochemistry | MS [M + H] |
|---|---|---|---|---|---|
| A62 | F | H | [phenyl-tetrazole-S- group] | Enantiomer B | 417.0 |

TABLE EX-B

[Structure: piperidine with H2N-S(=O)2-N, fused cyclopropane with X,X substituents, with C(=O)R group]

| Example | X | R | Stereochemistry | MS [M + H] |
|---|---|---|---|---|
| B1 | H | NH-(2-OMe-phenyl) | R | 340.1 |
| B2 | H | NH-(3-Cl-phenyl) | R | 344.1 |
| B3 | F | NH-(2-OMe-5-Cl-phenyl) | S | 410.1 |

The utility of the compounds in accordance with the present invention as positive allosteric modulators of α7 nicotinic acetylcholine receptor activity may be demonstrated by methodology known in the art. Direct activation of α7 (agonism), and potentiation of acetylcholine-evoked α7 currents was determined as follows:

Automated Patch-Clamp Electrophysiology Functional Assay (Assay A)

Automated patch-clamp electrophysiology was performed using the IonFlux HT (Fluxion Biosciences Inc., San Francisco, CA) in the whole-cell, population patch configuration. Test compounds were assessed for their ability to modulate the function of the α7 nicotinic acetylcholine receptor both in the presence, and in the absence of the natural α7 agonist acetylcholine. A HEK cell line stably expressing both human RIC-3 and human α7 (PrecisION hnAChR α7/RIC-3, Eurofins Pharma, St. Charles, MO) was cultured in 175 cm$^2$ triple-layer tissue culture flasks to no more than 90% confluency in DMEM/F-12 growth media supplemented with 10% heat-inactivated fetal bovine serum, 1% non-essential amino acids, 0.625 μg/mL Puromycin, and 400 μg/mL Geneticin. Immediately prior to assay, cells were detached by first aspirating growth media, rinsing with Dulbecco's phosphate buffered saline, and then adding 10 mL of Accutase (Innovative Cell Technologies, San Diego, CA) to the flask and then incubating at 37° C. for 5 minutes. Detached cells were then recovered by the addition of 40 mL of CHO-serum-free media supplemented with 25 mM HEPES, and rocked gently in a 50 mL conical tube for 20 minutes prior to patch-clamp assay. After recovery, cells were pelleted by centrifugation at 1,000 RPM for 1 minute in a compact bench top centrifuge; recovery media was aspirated and cells were resuspended in external recording solution (150 mM NaCl, 5 mM KCl, 2 mM CaCl$_2$, 1 mM MgCl$_2$, 10 mM HEPES, 12 mM dextrose) to a density of 5.0×10$^6$ cells/mL. The cell suspension was added to the cell inlet wells on an IonFlux HT population patch plate which had previously been rinsed and primed with deionized H$_2$O. Test compounds were serially diluted in DMSO and then resuspended to the final test concentration in external recording solution, with, or without 40 μM acetylcholine added to the external recording solution; test compounds were then transferred to the IonFlux HT population patch plate. Internal recording solution (110 mM TrisPO$_4$, 28 mM TrisBase, 0.1 mM CaCl$_2$, 2 mM MgCl$_2$, 11 mM EGTA, 4 mM MgATP) was added to the internal recording solution inlet wells on the IonFlux HT patch plate previously loaded with cells and test compounds, and the plate loaded into the IonFlux HT instrument. A protocol was executed on the IonFlux HT to trap the cells, break into the cells, and establish the whole-cell recording configuration; cells were voltage-clamped at a holding potential of −60 mV for the duration of the experiment, all experiments were conducted at room temperature, and the IonFlux HT injection pressure was 8 psi for solution applications. Upon establishing the whole-cell configuration, external recording solution was perfused into the recording chambers for 120 seconds and then 40 μM acetylcholine was applied for 1 second and immediately washed off with external recording solution for 60 seconds. The 40 μM acetylcholine-evoked α7 current served as the current response to which subsequent test compound effects, in the presence, or in the absence of 40 μM acetylcholine would be quantified relative to. Next, test compounds were evaluated at multiple concentrations for their ability to induce, or modulate α7 current responses; three concentrations of test compound were evaluated in ascending dose fashion per recording. To assess test compound agonist activity, test compound diluted in external recording solution was applied starting from the lowest concentration of test compound being tested in the concentration series, for 58 seconds; the first 20 seconds of the 58 second compound application period coincided with a data collection sweep which was 20 seconds in duration, and collected at a rate of 5,000 samples/second. To assess test compound positive allosteric modulator activity, immediately following the 58 second test compound only application period, the same concentration of test compound, diluted in external recording solution containing 40 μM acetylcholine was applied for 1 second; in this way, the test compound and the natural receptor agonist acetylcholine were co-applied, and potentiating effects of test compounds observed. The 1 second application of test compound diluted in external solution containing 40 μM acetylcholine coincided with a data collection sweep which was 20 seconds in duration, and collected at a rate of 5,000 samples/second, after which, external recording solution only was applied for 42 seconds. Following this 42 second wash with external recording solution only, the next highest concentration of the test compound in the concentration series was applied in the absence and then in the presence of acetylcholine as previously described, and data collected as previously described. After test compound agonist, and positive allosteric modulator activity were assessed at three ascending concentrations, the experiment was terminated and leak subtraction performed using the IonFlux HT data analysis software. Peak current amplitudes and the area under the curve (AUC) were both quantified for each current sweep using proprietary software and test compound effects where quantified as follows.

Test compound agonist activity was calculated as:

% Agonism=(Y/X)×100

Test compound potentiator activity was calculated as:

% Potentiation=[(Z/X)×100]−100

X=Peak current amplitude (or AUC) evoked by 40 μM acetylcholine
Y=Peak current amplitude (or AUC) evoked by test compound diluted in external recording solution
Z=Peak current amplitude (or AUC) evoked by test compound diluted in external recording solution containing 40 μM acetylcholine As such, test compounds which evoked the same current amplitude as 40 μM acetylcholine alone would exhibit a calculated % Agonism of 100%. Test compounds co-applied with 40 μM acetylcholine which evoked a current amplitude 2× the current evoked from 40 μM acetylcholine alone would exhibit a calculated % Potentiation of 100%, whereas test compounds co-applied with 40 μM acetylcholine which evoked the same current amplitude as 40 μM acetylcholine alone would be characterized as exhibiting no potentiation.

Agonist and potentiation data, derived by peak current amplitude or area under the curve (AUC) were graphed and fit using a 4-parameter logistic fit based on the Levenberg-Marquardt algorithm where $y=A+((B-A)/(1+((C/x)^{-D})))$ where:
A=Minimum
B=Maximum
C=$EC_{50}$
D=Slope
x=test compound concentration
y=% Agonism or % Potentiation Potency data for selected compounds of the present invention in the automated patch-clamp electrophysiology functional assay (Assay A) are represented in the table below:

| Example | α7 nAChR Potency |
|---|---|
| 1 | C |
| 2 | A |
| 3 | C |
| 4 | C |
| 5 | C |
| 6 | A |
| 7 | B |
| 8 | C |
| 9 | C |
| 10 | A |
| 11 | A |
| 12 | C |
| 13 | B |
| 14 | A |
| 15 | A |
| 16 | B |
| 17 | C |
| 18 | D |
| 19 | C |
| A1 | D |
| A2 | A |
| A3 | C |
| A4 | C |
| A5 | D |
| A6 | C |
| A7 | C |
| A8 | A |
| A9 | C |
| A10 | C |
| A11 | A |
| A12 | C |
| A13 | C |
| A14 | C |
| A15 | B |
| A16 | B |
| A17 | B |
| A18 | B |
| A19 | B |
| A20 | C |
| A21 | C |
| A22 | C |
| A23 | B |
| A24 | B |
| A25 | C |
| A26 | C |
| A27 | C |
| A28 | A |
| A29 | B |
| A30 | A |
| A31 | A |
| A32 | B |
| A33 | A |
| A34 | C |
| A35 | C |
| A36 | C |
| A37 | A |
| A38 | C |
| A39 | B |
| A40 | A |

| Example | α7 nAChR Potency |
|---|---|
| A41 | B |
| A42 | B |
| A43 | C |
| A44 | B |
| A45 | D |
| A46 | C |
| A47 | C |
| A48 | C |
| A49 | B |
| A50 | B |
| A51 | C |
| A52 | B |
| A53 | C |
| A54 | B |
| A55 | C |
| A56 | C |
| A57 | A |
| A58 | C |
| A59 | A |
| A60 | A |
| A61 | C |
| A62 | C |
| B1 | C |
| B2 | C |
| B3 | C |

*Potency defined as A ($EC_{50} \leq 0.1\ \mu M$); B ($0.1\ \mu M < EC_{50} \leq 0.5\ \mu M$); C ($0.5\ \mu M < EC_{50} \leq 5\ \mu M$); D ($5\ \mu M < EC_{50} \leq 50\ \mu M$)

Electrophysiology $EC_{50}$ values for selected compounds of the present invention in the automated patch-clamp electrophysiology functional assay (Assay A) are provided in the table below:

| Example | α7 nAChR $EC_{50}$ (nM) |
|---|---|
| 1 | 730 |
| 2 | 71 |
| 3 | 930 |
| 4 | 580 |
| 5 | 3200 |
| 6 | 49 |
| 7 | 330 |
| 8 | 1200 |
| 9 | 1200 |
| 10 | 74 |
| 11 | 52 |
| 12 | 1600 |
| 13 | 200 |
| 14 | 48 |
| 15 | 63 |
| 16 | 100 |
| 17 | 720 |
| 19 | 1900 |
| A1 | 6200 |
| A2 | 25 |
| A3 | 1300 |
| A5 | 6200 |
| A6 | 940 |
| A7 | 1200 |
| A8 | 89 |
| A9 | 650 |
| A10 | 1500 |
| A11 | 90 |
| A12 | 4200 |
| A13 | 4100 |
| A14 | 700 |
| A15 | 470 |
| A16 | 190 |
| A17 | 130 |
| A18 | 300 |
| A19 | 190 |
| A20 | 1800 |
| A21 | 1100 |
| A22 | 3100 |
| A23 | 150 |
| A24 | 180 |
| A25 | 1900 |
| A26 | 650 |
| A28 | 37 |
| A29 | 310 |
| A30 | 58 |
| A32 | 140 |
| A33 | 20 |
| A34 | 550 |
| A35 | 540 |
| A36 | 1200 |
| A37 | 74 |
| A38 | 720 |
| A39 | 310 |
| A40 | 19 |
| A42 | 120 |
| A43 | 1400 |
| A44 | 150 |
| A47 | 1100 |
| A48 | 1700 |
| A49 | 280 |
| A50 | 250 |
| A51 | 570 |
| A52 | 480 |
| A53 | 640 |
| A54 | 450 |
| A56 | 740 |
| A57 | 69 |
| A59 | 22 |
| A60 | 11 |
| A61 | 1300 |
| A62 | 2000 |
| B1 | 1400 |
| B3 | 1400 |

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A compound which is selected from
   1-({[2-(difluoromethoxy)pyridin-4-yl]oxy}methyl)-6-azaspiro[2.5]octane-6-sulfonamide;
   2-({[2-(difluoromethoxy)pyridin-4-yl]oxy}methyl)-1,1-difluoro-6-azaspiro[2.5]octane-6-sulfonamide;
   (1R)-1-{[(5-phenyl-1,2,4-oxadiazol-3-yl)oxy]methyl}-6-azaspiro[2.5]octane-6-sulfonamide;
   1-({[2-(trifluoromethyl)pyridin-4-yl]oxy}methyl)-6-azaspiro[2.5]octane-6-sulfonamide;
   1,1-difluoro-2-{[(5-phenyl-1,2,4-oxadiazol-3-yl)oxy]methyl}-6-azaspiro[2.5]octane-6-sulfonamide;
   1-{[3-(2,2,2-trifluoroethoxy)phenoxy]methyl}-6-azaspiro[2.5]octane-6-sulfonamide;
   (1R)-1-({[2-(2,2,2-trifluoroethoxy)pyridin-3-yl]oxy}methyl)-6-azaspiro[2.5]octane-6-sulfonamide;
   (1R)-1-({[6-(2,2,2-trifluoroethoxy)pyridin-2-yl]methoxy}methyl)-6-azaspiro[2.5]octane-6-sulfonamide;
   (1R)-1-[({6-[(2,2,2-trifluoroethyl)amino]pyridin-2-yl}oxy)methyl]-6-azaspiro[2.5]octane-6-sulfonamide;
   (1R)-1-{[(5-chloro-2-methoxyphenyl)sulfanyl]methyl}-6-azaspiro[2.5]octane-6-sulfonamide;
   (1R)-1-{[(5-chloro-2-methoxyphenyl)sulfonyl]methyl}-6-azaspiro[2.5]octane-6-sulfonamide;

(1R)—N-(5-chloro-2-methoxyphenyl)-6-sulfamoyl-6-azaspiro[2.5]octane-1-carboxamide;
(1R)-1-{[(5-chloro-2-methoxyphenyl)amino]methyl}-6-azaspiro[2.5]octane-6-sulfonamide;
(1R)—N-(5-chloro-2-methoxyphenyl)-2,2-difluoro-6-sulfamoyl-6-azaspiro[2.5]octane-1-carboxamide;
(1R)-1-({[6-(morpholin-4-yl)pyridin-2-yl]oxy}methyl)-6-azaspiro[2.5]octane-6-sulfonamide;
1,1-difluoro-2-({[4-fluoro-2-(trifluoromethyl)phenyl]sulfanyl}methyl)-6-azaspiro[2.5]octane-6-sulfonamide;
1,1-difluoro-2-{2-[4-fluoro-2-(trifluoromethyl)phenyl]ethyl}-6-azaspiro[2.5]octane-6-sulfonamide;
1,1-difluoro-2-{(E)-2-[4-fluoro-2-(trifluoromethyl)phenyl]ethenyl}-6-azaspiro[2.5]octane-6-sulfonamide;
(1R)-1-{[(2,6-dimethoxypyridin-3-yl)oxy]methyl}-6-azaspiro[2.5]octane-6-sulfonamide;
2-[(5-chloro-2-methoxyphenoxy)methyl]-1,1-difluoro-6-azaspiro[2.5]octane-6-sulfonamide;
(1R)-1-[(4-fluoro-3-methoxyphenoxy)methyl]-6-azaspiro[2.5]octane-6-sulfonamide;
(1S)-1-[(4-fluoro-3-methoxyphenoxy)methyl]-6-azaspiro[2.5]octane-6-sulfonamide;
(1R)-1-[(4-fluoro-2-methoxyphenoxy)methyl]-6-azaspiro[2.5]octane-6-sulfonamide;
1-{[4-fluoro-2-(trifluoromethyl)phenoxy]methyl}-6-azaspiro[2.5]octane-6-sulfonamide;
1,1-difluoro-2-{[5-fluoro-2-(trifluoromethyl)phenoxy]methyl}-6-azaspiro[2.5]octane-6-sulfonamide;
1-{[2-(difluoromethoxy)phenoxy]methyl}-6-azaspiro[2.5]octane-6-sulfonamide;
1,1-difluoro-2-{[4-fluoro-2-(trifluoromethyl)phenoxy]methyl}-6-azaspiro[2.5]octane-6-sulfonamide;
1,1-difluoro-2-({[1-methyl-3-(trifluoromethyl)-1H-pyrazol-5-yl]oxy}methyl)-6-azaspiro[2.5]octane-6-sulfonamide;
(1S)-1-{[(5-phenyl-1,2,4-oxadiazol-3-yl)oxy]methyl}-6-azaspiro[2.5]octane-6-sulfonamide;
1-{[(3-methyl-1-phenyl-1H-pyrazol-5-yl)oxy]methyl}-6-azaspiro[2.5]octane-6-sulfonamide;
1-{[5-fluoro-2-(trifluoromethyl)phenoxy]methyl}-6-azaspiro[2.5]octane-6-sulfonamide;
(1S)-1-({[4-methoxy-6-(2,2,2-trifluoroethoxy)pyridin-2-yl]oxy}methyl)-6-azaspiro[2.5]octane-6-sulfonamide;
(1R)-1-({[6-(cyclopropylmethoxy)pyridin-2-yl]oxy}methyl)-6-azaspiro[2.5]octane-6-sulfonamide;
(1S)-1-({[6-(cyclopropylmethoxy)pyridin-2-yl]oxy}methyl)-6-azaspiro[2.5]octane-6-sulfonamide;
(1R)-1-({[6-(3,5-dimethyl-1H-pyrazol-1-yl)pyridin-2-yl]oxy}methyl)-6-azaspiro[2.5]octane-6-sulfonamide;
(1S)-1-({[6-(3,5-dimethyl-1H-pyrazol-1-yl)pyridin-2-yl]oxy}methyl)-6-azaspiro[2.5]octane-6-sulfonamide;
4,4-difluoro-1-{[(5-phenyl-1,2,4-oxadiazol-3-yl)oxy]methyl}-6-azaspiro[2.5]octane-6-sulfonamide;
1-{[3-(difluoromethoxy)phenoxy]methyl}-6-azaspiro[2.5]octane-6-sulfonamide;
(1R)-1-{[3-(trifluoromethoxy)phenoxy]methyl}-6-azaspiro[2.5]octane-6-sulfonamide;
(1S)-1-{[3-(trifluoromethoxy)phenoxy]methyl}-6-azaspiro[2.5]octane-6-sulfonamide;
1-[(2-fluoro-5-methoxyphenoxy)methyl]-6-azaspiro[2.5]octane-6-sulfonamide;
1-{[(6-methoxypyridin-2-yl)oxy]methyl}-6-azaspiro[2.5]octane-6-sulfonamide;
2-{[3-(difluoromethoxy)phenoxy]methyl}-1,1-difluoro-6-azaspiro[2.5]octane-6-sulfonamide;
1,1-difluoro-2-{[3-(2,2,2-trifluoroethoxy)phenoxy]methyl}-6-azaspiro[2.5]octane-6-sulfonamide;
1,1-difluoro-2-[(2-fluoro-5-methoxyphenoxy)methyl]-6-azaspiro[2.5]octane-6-sulfonamide;
1-({[2-(2,2,2-trifluoroethoxy)pyridin-4-yl]oxy}methyl)-6-azaspiro[2.5]octane-6-sulfonamide;
1,1-difluoro-2-({[2-(2,2,2-trifluoroethoxy)pyridin-4-yl]oxy}methyl)-6-azaspiro[2.5]octane-6-sulfonamide;
1,1-difluoro-2-({[2-(2,2,2-trifluoroethoxy)pyridin-3-yl]oxy}methyl)-6-azaspiro[2.5]octane-6-sulfonamide;
(1R)-1-({[6-(2,2,2-trifluoroethoxy)pyridin-2-yl]oxy}methyl)-6-azaspiro[2.5]octane-6-sulfonamide;
(1S)-1-({[6-(2,2,2-trifluoroethoxy)pyridin-2-yl]oxy}methyl)-6-azaspiro[2.5]octane-6-sulfonamide;
4,4-difluoro-1-({[6-(2,2,2-trifluoroethoxy)pyridin-2-yl]oxy}methyl)-6-azaspiro[2.5]octane-6-sulfonamide;
1,1-difluoro-2-({[6-(2,2,2-trifluoroethoxy)pyridin-2-yl]oxy}methyl)-6-azaspiro[2.5]octane-6-sulfonamide;
1-[(5-chloro-2-methoxyphenoxy)methyl]-6-azaspiro[2.5]octane-6-sulfonamide;
1-({[4-(trifluoromethyl)phenyl]sulfanyl}methyl)-6-azaspiro[2.5]octane-6-sulfonamide;
1,1-difluoro-2-({[4-(trifluoromethyl)phenyl]sulfanyl}methyl)-6-azaspiro[2.5]octane-6-sulfonamide;
(1R)-1-({[6-(methylsulfonyl)pyridin-2-yl]oxy}methyl)-6-azaspiro[2.5]octane-6-sulfonamide;
(1R)-1-({[6-(4-methylpiperazin-1-yl)pyridin-2-yl]oxy}methyl)-6-azaspiro[2.5]octane-6-sulfonamide;
(1R)-1-{[(6-cyanopyridin-2-yl)oxy]methyl}-6-azaspiro[2.5]octane-6-sulfonamide;
(1R)-1-{[(6-methylpyridin-2-yl)oxy]methyl}-6-azaspiro[2.5]octane-6-sulfonamide;
(1R)-1-{[(6-cyclopropylpyridin-2-yl)oxy]methyl}-6-azaspiro[2.5]octane-6-sulfonamide;
(1R)-1-({[6-(3-methyl-1H-pyrazol-1-yl)pyridin-2-yl]oxy}methyl)-6-azaspiro[2.5]octane-6-sulfonamide;
(1R)-1-{[(6-methoxypyridin-2-yl)oxy]methyl}-6-azaspiro[2.5]octane-6-sulfonamide;
(1R)-1-({[6-(2-hydroxypropan-2-yl)pyridin-2-yl]oxy}methyl)-6-azaspiro[2.5]octane-6-sulfonamide;
(1R)-1-({[6-(propan-2-yl)pyridin-2-yl]oxy}methyl)-6-azaspiro[2.5]octane-6-sulfonamide;
(1R)-1-{[(6-ethoxypyridin-2-yl)oxy]methyl}-6-azaspiro[2.5]octane-6-sulfonamide;
(1R)-1-{[(6-tert-butylpyridin-2-yl)oxy]methyl}-6-azaspiro[2.5]octane-6-sulfonamide;
(1R)-1-({[6-(1,1-difluoroethyl)pyridin-2-yl]oxy}methyl)-6-azaspiro[2.5]octane-6-sulfonamide;
(1R)-1-{[(6-phenylpyridin-2-yl)oxy]methyl}-6-azaspiro[2.5]octane-6-sulfonamide;
(1R)-1-[(2,4'-bipyridin-6-yloxy)methyl]-6-azaspiro[2.5]octane-6-sulfonamide;
(2R)-2-{[(5-chloro-2-methoxyphenyl)amino]methyl}-1,1-difluoro-6-azaspiro[2.5]octane-6-sulfonamide;
(2R)-2-{[(2,5-dimethylphenyl)amino]methyl}-1,1-difluoro-6-azaspiro[2.5]octane-6-sulfonamide;
1,1-difluoro-2-{[(1-phenyl-1H-tetrazol-5-yl)sulfanyl]methyl}-6-azaspiro[2.5]octane-6-sulfonamide;
(1R)—N-(2-methoxyphenyl)-6-sulfamoyl-6-azaspiro[2.5]octane-1-carboxamide;
(1R)—N-(3-chlorophenyl)-6-sulfamoyl-6-azaspiro[2.5]octane-1-carboxamide; and
(1S)—N-(5-chloro-2-methoxyphenyl)-2,2-difluoro-6-sulfamoyl-6-azaspiro[2.5]octane-1-carboxamide;

or a pharmaceutically acceptable salt thereof.

2. A pharmaceutical composition comprising (i) a pharmaceutically acceptable carrier and (ii) a compound of claim 1 or a pharmaceutically acceptable salt thereof.

3. The pharmaceutical composition of claim 2, further comprising a second therapeutic agent selected from the group consisting of acetylcholinesterase inhibitors; NMDA receptor antagonists; antipsychotics; MAO-B inhibitors; and levodopa.

4. A method of treating a patient with cognitive impairments associated with Alzheimer's disease, Parkinson's disease, and schizophrenia, the method comprising administering to the patient the compound of claim 1, or a pharmaceutically acceptable salt thereof, in an amount effective to treat the patient.

5. A method of modulating α7 nAChR activity, the method comprising administering an effective amount of a compound of claim 1 to a patient in need thereof.

* * * * *